United States Patent
Kirn

(10) Patent No.: US 9,919,062 B2
(45) Date of Patent: Mar. 20, 2018

(54) ONCOLYTIC VACCINIA VIRUS CANCER THERAPY

(71) Applicant: SILLAJEN BIOTHERAPEUTICS, INC., San Francisco, CA (US)

(72) Inventor: David Kirn, San Francisco, CA (US)

(73) Assignee: SILLAJEN BIOTHERAPEUTICS, INC., San Francisco, CA (US)

( * ) Notice: Subject to any disclaimer, the term of this patent is extended or adjusted under 35 U.S.C. 154(b) by 54 days.

(21) Appl. No.: 14/966,691

(22) Filed: Dec. 11, 2015

(65) Prior Publication Data

US 2016/0129135 A1 May 12, 2016

Related U.S. Application Data

(63) Continuation of application No. 14/656,397, filed on Mar. 12, 2015, now Pat. No. 9,226,977, which is a continuation of application No. 13/535,291, filed on Jun. 27, 2012, now Pat. No. 8,980,246, which is a continuation-in-part of application No. 12/531,353, filed as application No. PCT/US2008/057257 on Mar. 17, 2008, now abandoned, said application No. 13/535,291 is a continuation-in-part of application No. 11/470,951, filed on Sep. 7, 2006, now Pat. No. 9,180,149.

(60) Provisional application No. 60/894,932, filed on Mar. 15, 2007, provisional application No. 60/714,979, filed on Sep. 7, 2005.

(51) Int. Cl.

| | |
|---|---|
| A61K 48/00 | (2006.01) |
| A61K 38/19 | (2006.01) |
| A61K 35/768 | (2015.01) |
| A61K 9/00 | (2006.01) |
| A61K 45/06 | (2006.01) |
| A61K 38/20 | (2006.01) |
| A61N 5/10 | (2006.01) |

(52) U.S. Cl.
CPC ........ *A61K 48/0066* (2013.01); *A61K 9/0019* (2013.01); *A61K 35/768* (2013.01); *A61K 38/191* (2013.01); *A61K 38/193* (2013.01); *A61K 38/208* (2013.01); *A61K 38/2013* (2013.01); *A61K 45/06* (2013.01); *A61K 48/0075* (2013.01); *A61N 5/10* (2013.01); *A61K 48/00* (2013.01); *C12N 2710/24132* (2013.01)

(58) Field of Classification Search
CPC .......................... A61K 48/005; A61K 35/768
See application file for complete search history.

(56) References Cited

U.S. PATENT DOCUMENTS

| | | | |
|---|---|---|---|
| 8,980,246 B2 * | 3/2015 | Kirn | A61K 38/193 424/93.2 |
| 9,226,977 B2 * | 1/2016 | Kirn | A61K 38/193 |
| 2007/0065411 A1 * | 3/2007 | Kirn | A01K 67/0271 424/93.2 |

OTHER PUBLICATIONS

Kim et al. (Molecular Therapy. May 2005; 11(1):S67. Abstract #167: Both Oncolysis and Tumor Immunity Are Involved in an Autitumoral Efficacy by Intratumoral Injection of Recombinant Vaccinia Virus (TK Deleted, hGM-CSF Inserted Wyeth Strain) in a VX2 Rabbit Model).*
Schmitz et al. (Gut 2002; 50: 130-135).*
Mahvi et al. (Human Gene Therapy. 1997; 8:875-891).*
Kim et al. (Molecular Therapy. May 2005; 11(1):S67. Abstract #168: Antitumoral Efficacy of Multiple Injection of JX-594 (Thymidine Kinase (TK) Deleted, Human GM-CSF Inserted Wyeth Strain) Via Tail Vein in NNitrosomorpholine (NNM) Treated Rats).*

* cited by examiner

*Primary Examiner* — Scott Long
(74) *Attorney, Agent, or Firm* — Polsinelli PC; Christopher M. Cabral

(57) ABSTRACT

Embodiments of the invention are directed methods that include a thymidine kinase deficient vaccinia virus. The methods include administering the vaccinia virus at increased viral concentrations. Further aspects of the invention include methods for inducing oncolysis or collapse of tumor vasculature in a subject having a tumor comprising administering to a subject at least $1 \times 10^8$ infectious viral particles of a TK-deficient, GM-CSF-expressing, replication-competent vaccinia virus vector sufficient to induce oncolysis of cells in the tumor.

20 Claims, 39 Drawing Sheets

FIG. 6A
FIG. 6B
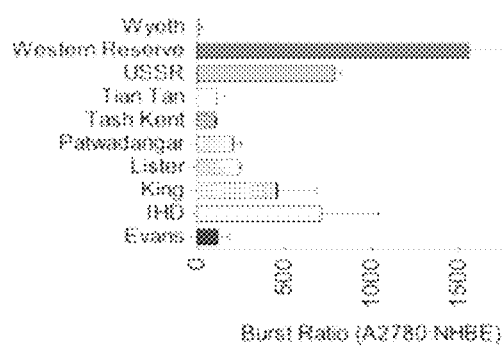
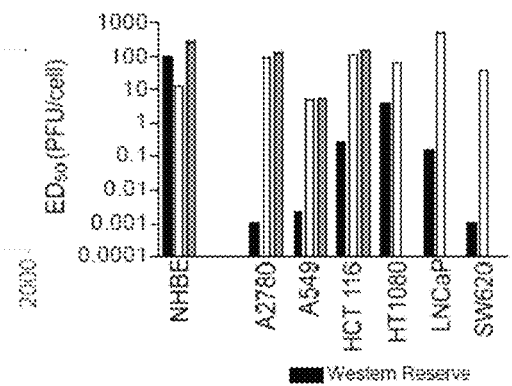
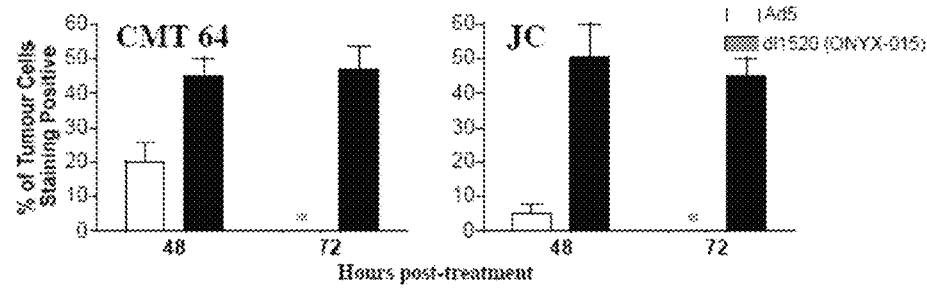
FIG. 6C

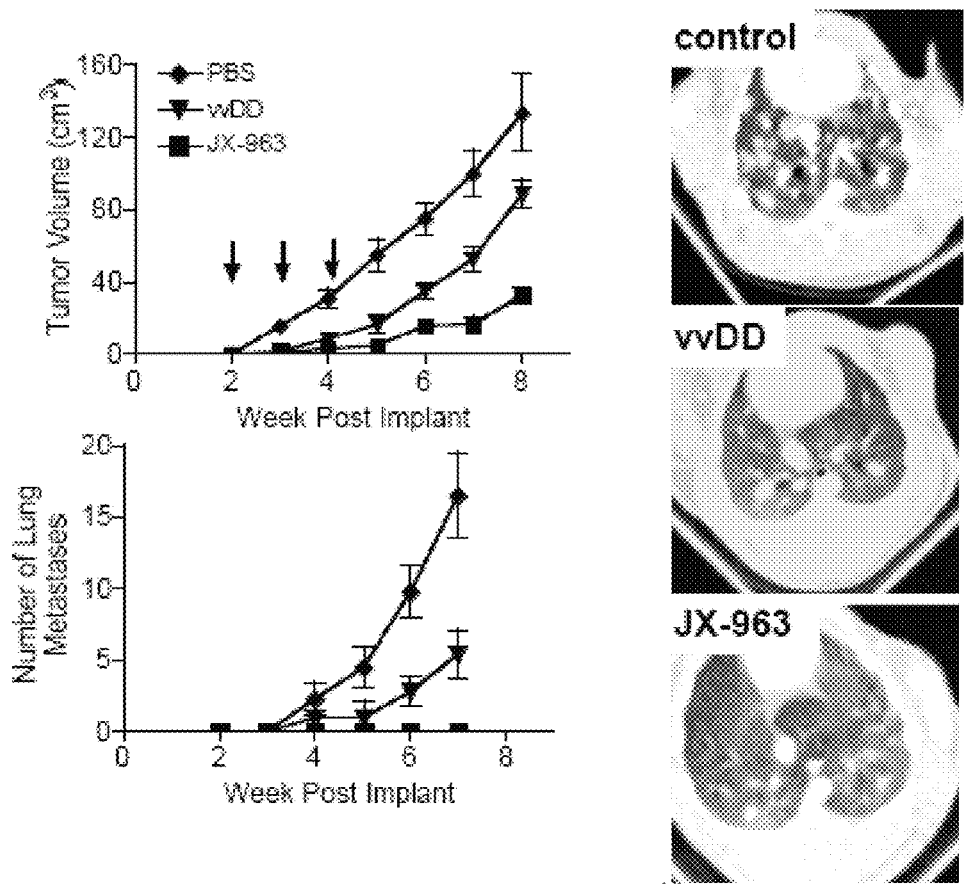
FIG. 9A
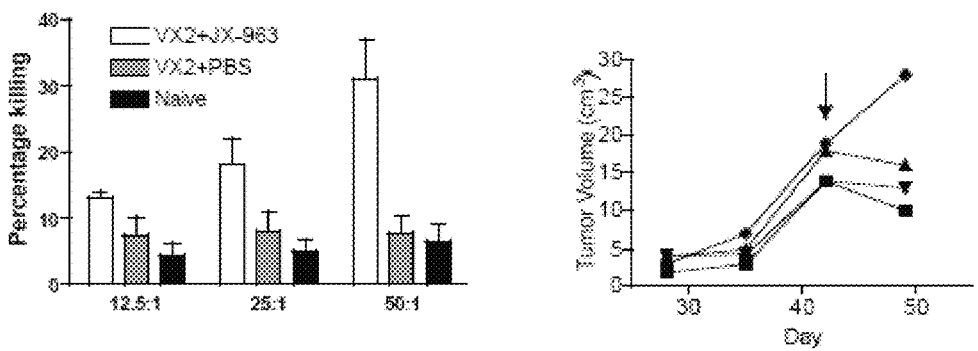
FIG. 9B
FIG. 9C

CLINICAL TRIAL STUDY DESIGN
JX-594 by Intratumoral Injection

Protocol Number: JX594-IT-hep001

A Phase I Clinical Study to Evaluate Safety and Efficacy of JX-594 (Thymidine Kinase Deleted Vaccinia Virus plus GM-CSF) Administered by Intratumoral Injection in Patients with Solid Tumors within the Liver

| Phase | Patients | Sites | Location | IND Holder |
|---|---|---|---|---|
| 1 | ~18 | 1 | Korea | Dr. Hwang TH |

| Eligibility | Primary Objectives (Secondary and Other) | Dose | Treatment |
|---|---|---|---|
| Hepatocellular carcinoma (HCC) or other cancer metastatic to the liver | -MTD (or MFD)<br>-safety<br>-594 replication/PK<br>-immune response to 594<br>-antitumoral efficacy (injected & distant) | 4 Cohorts: Start at $10^8$ pfu/dose; end at $3 \times 10^9$ pfu/dose | -1 cycle = 3 weeks<br>-4 cycles possible<br>-Repeat dosing option<br>-Response eval Q 6 weeks  -Biopsy required (if safe)<br>-PET optional |

FIG. 15

CLINICAL TRIAL STUDY DESIGN
JX – 594 by Intratumoral Injection

Protocol Number: JX594 – IT – MEL005

A Phase II, Open-Label Study of JX-594 (Thymidine Kinase-deleted Vaccinia Virus plus GM-CSF) Administered by Intratumoral Injection in Patients with Unresectable Stage 3 or Stage 4 Malignant Melanoma

| Phase | Patients | Sites | Location | IND Holder |
|---|---|---|---|---|
| 1 / 2 | 15 | 2–3 | United States | Jennerex |

| Eligibility | Primary Objectives (Secondary and Other) | Dose | Treatment |
|---|---|---|---|
| Stage 3 or stage 4 malignant melanoma not surgically resectable for cure | – objective response rate of injected tumors<br>– safety and toxicity<br>– overall response rate<br>– progression-free survival<br>– objective response rate of non-injected tumors<br>– overall survival, clinical benefit, MIA, 594 PK and PD, immune response to 594, histologic endpoints | 1 dose level: 1 x $10^8$ pfu/treatment | – Weekly injections x 6 weeks – Response eval @ 6 weeks and every 3–6 weeks thereafter<br>– Biopsy in subset of up to 10 patients<br>– PK in all patients |

FIG. 16

| Cohort | Patient # | Patient Demog | Tumor Type (Live Target LD) | # of Cycles (Date of 1st treatment) | Status |
|---|---|---|---|---|---|
| 1 | 101 | M 55 | Gastric (8.5 cm) | 1 (09-Jan-2006) | Treatment Completed (died 04-Mar-2006) |
| 1 | 102 | F 56 | Sigmoid colon (4.1 cm) | 3 (06-Feb-2006) | Treatment Completed (died 11-Oct-2006) |
| 1 | 103 | M 53 | Thymic (9.8 cm) | 6 + 2HAI (16-May-2006) | Treatment Completed (alive, in follow-up) |
| 2 | 201 | M 66 | HCC (6.2 cm) | 8 (30-May-2006) | Treatment Completed (alive, in follow-up) |
| 2 | 202 | M 50 | Squam lung* (9.7 cm) | 4 (12-Jun-2006) | Treatment Completed (alive, in follow-up) |
| 2 | 203 | M 56 | HCC (6.1 cm) | 5 (12-Jul-2006) | Treatment Completed (died 23-Nov-2006) |

*presumed

FIG. 20

| Cohort | Patient # | Patient Demog | Tumor Type (Liver Target LD) | # of Cycles (Date of 1st treatment) | Status |
|---|---|---|---|---|---|
| 3 | 301 | M 44 | Renal (5.7 cm) | 4 (02-Oct-2006) | Treatment Completed (alive, in follow-up) |
| 3 | 302 | M 62 | Colon (9.0 cm) | 4 (22-Nov-2006) | Treatment Completed (alive, in follow-up) |
| 3 | 303 | F 37 | Melanoma (10.9 cm) | 1 (28-Nov-2006) | Treatment Completed (died 06-Dec-2006) |
| 3 | 304 | M 65 | Melanoma (1.8 cm) | 3+ (28-Dec-2006) | Active |
| 3 | 305 | F 63 | Colon (7.4 cm) | 1+ (28-Feb-2007) | Active |

FIG. 21

|  | Patient # | Cycle # | | | |
|---|---|---|---|---|---|
|  |  | 1 | 2 | 3 | 4 |
| Cohort 1 | 101 | + |  |  |  |
|  | 102 | − | − | − |  |
|  | 103 | + | − | + | − |
| Cohort 2 | 201 hep | + | + | − | + |
|  | 201 neck | + | − | + | − |
|  | 202 | − | − | − | − |
|  | 203 | + | − | − | − |
| Cohort 3 | 301 | − | − | − | + |
|  | 302 | + | − | p | p |
|  | 303 | + |  |  |  |
|  | 304 | + | − | p | p |

FIG. 23

| Patient ID | # Cycles | Efficacy Data: L (injection site); D (distant) | Days Survival Post-treatment (mo.) |
|---|---|---|---|
| 101 (gastric) | 1 | L – acute vascular shut-down; necrosis (response n.a.) | 54 |
| 102 (CRC) | 3 | L – SD (TTP – 2 mo.) | 247 (8.2) |
| 103 (thymic) | 6 (2 HAI) | L – PR (70% decr. area – 5+ mo.) D – TTP (new tumors) 4 mo. | 280+ (9.5+) |
| 201 (HCC) | 8 | L – neck: PR (70% decr. area – 4+ mo.); PET(–); liver: PET decrease, SD (8+ mo.) D – new neck tumor – PET near CR post-IT AFP decrease 99.9% (>30,000 to 36) | 263+ (8.75+) |
| 202 (squam. lung) | 4 | L – SD (8+ mo.) D – new neck tumor 6 mo. (CR with XRT) | 250+ (8.3+) |
| 203 (HCC) | 5 | L – AFP 40% decrease – SD: TTP 4 mo. D – PET decrease | 134 (4.5) |
| 301 (RCC) | 4 | L – SD – 4+ mo. – D– PD (12 cm tumor) | 138+ (4.6+) |
| 302 (CRC) | 4+ | L – SD 3+ mo. (CEA SD 3+) | 87+ (3+) |
| 304 (melanoma) | 2+ | L – PET decrease D – PET decrease | 51+ (1.7+) |

FIG. 33

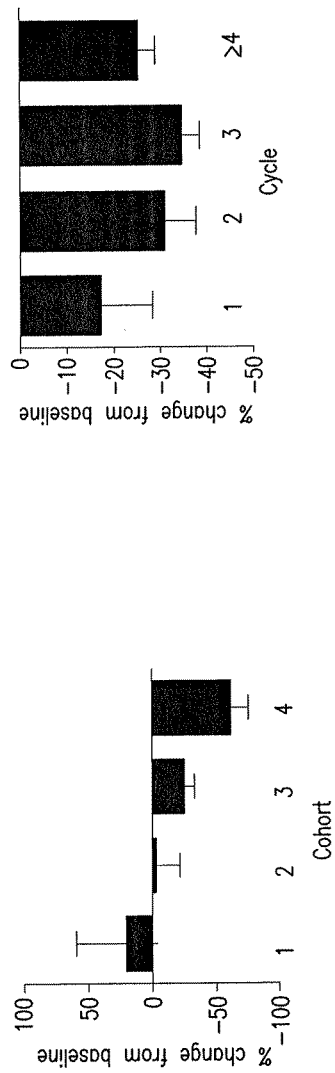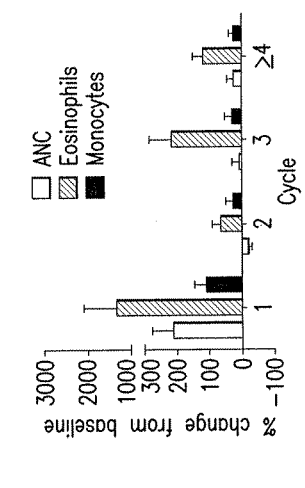
FIG. 36A
FIG. 36B
FIG. 36C

Pleural effusion

US 9,919,062 B2

ONCOLYTIC VACCINIA VIRUS CANCER THERAPY

CROSS-REFERENCE TO RELATED APPLICATIONS

This application is a continuation of U.S. patent application Ser. No. 14/656,397 filed Mar. 12, 2015, which is a continuation of U.S. patent application Ser. No. 13/535,291 filed Jun. 27, 2012 (now U.S. Pat. No. 8,980,246) which is a continuation-in-part of U.S. patent application Ser. No. 12/531,353 filed May 11, 2010, which is the U.S. national stage of International Application PCT/US08/57257 filed Mar. 17, 2008, and which claims the benefit of U.S. Provisional Patent Application No. 60/894,932 filed Mar. 15, 2007, and U.S. patent application Ser. No. 13/535,291 filed Jun. 27, 2012 (now U.S. Pat. No. 8,980,246) is a continuation-in-part of U.S. patent application Ser. No. 11/470,951 filed Sep. 7, 2006 (now U.S. Pat. No. 9,180,149) which claims the benefit of U.S. Provisional Application No. 60/714,979 filed Sep. 7, 2005, the disclosures of which are incorporated herein by reference in their entireties.

FIELD OF THE INVENTION

The present invention relates generally to the fields of oncology and virology. More particularly, it concerns poxviruses, specifically including oncolytic vaccinia viruses suitable for the treatment of cancer.

BACKGROUND OF THE INVENTION

Normal tissue homeostasis is a highly regulated process of cell proliferation and cell death. An imbalance of either cell proliferation or cell death can develop into a cancerous state (Solyanik et al., 1995; Stokke et al., 1997; Mumby and Walter, 1991; Natoli et al., 1998; Magi-Galluzzi et al., 1998). For example, cervical, kidney, lung, pancreatic, colorectal, and brain cancer are just a few examples of the many cancers that can result (Erlandsson, 1998; Kolmel, 1998; Mangray and King, 1998; Mougin et al., 1998). In fact, the occurrence of cancer is so high that over 500,000 deaths per year are attributed to cancer in the United States alone.

The maintenance of cell proliferation and cell death is at least partially regulated by proto-oncogenes and tumor suppressors. A proto-oncogene or tumor suppressor can encode proteins that induce cellular proliferation (e.g., sis, erbB, src, ras and myc), proteins that inhibit cellular proliferation (e.g., Rb, p16, p19, p21, p53, NF1 and WT1) or proteins that regulate programmed cell death (e.g., bcl-2) (Ochi et al., 1998; Johnson and Hamdy, 1998; Liebermann et al., 1998). However, genetic rearrangements or mutations of these proto-oncogenes and tumor suppressors result in the conversion of a proto-oncogene into a potent cancer-causing oncogene or of a tumor suppressor into an inactive polypeptide. Often, a single point mutation is enough to achieve the transformation. For example, a point mutation in the p53 tumor suppressor protein results in the complete loss of wild-type p53 function (Vogelstein and Kinzler, 1992).

Currently, there are few effective options for the treatment of many common cancer types. The course of treatment for a given individual depends on the diagnosis, the stage to which the disease has developed and factors such as age, sex, and general health of the patient. The most conventional options of cancer treatment are surgery, radiation therapy and chemotherapy. Surgery plays a central role in the diagnosis and treatment of cancer. Typically, a surgical approach is required for biopsy and to remove cancerous growth. However, if the cancer has metastasized and is widespread, surgery is unlikely to result in a cure and an alternate approach must be taken.

Radiation therapy and chemotherapy are the most common alternatives to surgical treatment of cancer (Mayer, 1998; Ohara, 1998; Ho et al., 1998). Radiation therapy involves a precise aiming of high energy radiation to destroy cancer cells and much like surgery, is mainly effective in the treatment of non-metastasized, localized cancer cells. Side effects of radiation therapy include skin irritation, difficulty swallowing, dry mouth, nausea, diarrhea, hair loss, and loss of energy (Curran, 1998; Brizel, 1998). Chemotherapy, the treatment of cancer with anti-cancer drugs, is another mode of cancer therapy, and most chemotherapy approaches include the combination of more than one anti-cancer drug, which has proven to increase the response rate of a wide variety of cancers (U.S. Pat. Nos. 5,824,348; 5,633,016 and 5,798,339, incorporated herein by reference). However, a major side effect of chemotherapy drugs is that they also affect normal tissue cells, with the cells most likely to be affected being those that divide rapidly in some cases (e.g., bone marrow, gastrointestinal tract, reproductive system and hair follicles). Other toxic side effects of chemotherapy drugs can include sores in the mouth, difficulty swallowing, dry mouth, nausea, diarrhea, vomiting, fatigue, bleeding, hair loss, and infection.

Immunotherapy, a rapidly evolving area in cancer research, is yet another option for the treatment of certain types of cancers. Theoretically, the immune system may be stimulated to identify tumor cells as being foreign and targets them for destruction. Unfortunately, the response typically is not sufficient to prevent most tumor growth. However, recently there has been a focus in the area of immunotherapy to develop methods that augment or supplement the natural defense mechanism of the immune system. Examples of immunotherapies currently under investigation or in use are immune adjuvants (e.g., *Mycobacterium bovis*, *Plasmodium falciparum*, dinitrochlorobenzene and aromatic compounds) (U.S. Pat. Nos. 5,801,005 and 5,739,169; Hui and Hashimoto, 1998; Christodoulides et al., 1998), cytokine therapy (e.g., interferons (IL-1, GM-CSF and TNF) (Bukowski et al., 1998; Davidson et al., 1998; Hellstrand et al., 1998), and gene therapy (e.g., TNF, IL-1, IL-2, p53) (Qin et al., 1998; Austin-Ward and Villaseca, 1998; U.S. Pat. Nos. 5,830,880 and 5,846,945) and monoclonal antibodies (e.g., anti-ganglioside GM2, anti-HER-2, anti-p185) (Pietras et al., 1998; Hanibuchi et al., 1998; U.S. Pat. No. 5,824,311). Such methods, while showing some promise, have demonstrated limited success.

Replication-selective oncolytic viruses hold promise for the treatment of cancer (Kim et al., 2001). These viruses can cause tumor cell death through direct replication-dependent and/or viral gene expression-dependent oncolytic effects (Kim et al., 2001). In addition, viruses are able to enhance the induction of cell-mediated antitumoral immunity within the host (Todo et al., 2001; Sinkovics et al., 2000). These viruses also can be engineered to expressed therapeutic transgenes within the tumor to enhance antitumoral efficacy (Hermiston, 2000).

However, major limitations exist to this therapeutic approach. Although a degree of natural tumor-selectivity can be demonstrated for some virus species, new approaches are still needed to engineer and/or enhance tumor-selectivity for oncolytic viruses in order to maximize safety. This selectivity will become particularly important when intravenous administration is used, and when potentially toxic therapeutic genes are added to these viruses to enhance antitumoral potency; gene expression will need to be tightly limited in normal tissues. In addition, increased antitumoral potency through additional mechanisms such as induction of antitumoral immunity or targeting of the tumor-associated vasculature is highly desirable Therefore, more effective and less toxic therapies for the treatment of cancer are needed. The use of oncolytic viruses presents a potential area for development, however, the limitations discussed above need to be overcome. The present invention addresses these limitations.

SUMMARY OF THE INVENTION

Embodiments of the invention are directed to methods that include administration of a thymidine kinase deficient vaccinia virus. The methods include administering the vaccinia virus at increased viral concentrations. In certain aspects, the methods include inducing oncolysis or collapse of tumor vasculature in a subject having a tumor comprising administering to said subject at least $1 \times 10^8$ infective viral particles of a TK-deficient, granulocyte-macrophage colony stimulating factor (GM-CSF)-expressing, replication-competent vaccinia virus vector sufficient to induce oncolysis of cells in the tumor. Preferably, the virus vector has an expression region with a promoter directing expression of a nucleic acid encoding human GM-CSF. In a further aspect of the invention, the methods can exclude pre-treatment of a subject with a vaccinia vaccine, e.g., a subject need not be vaccinated 1, 2, 3, 4, 5, or more days, weeks, months, or years before administering the therapy described herein. In some aspects, non-injected tumors or cancer will be infected with the therapeutic virus, thus treating a patient by both local administration and systemic dissemination. In some aspects, the virus vector is administered intravascularly, i.e. intravenously or intraarterially.

In certain aspects, the subject is administered one or more doses of infectious viral particles or plaque forming units (pfu), each dose containing at least $2 \times 10^8$, $5 \times 10^8$, $1 \times 10^9$ $2 \times 10^9$, $5 \times 10^9$, $1 \times 10^{10}$, $5 \times 10^{10}$, $1 \times 10^{11}$, $5 \times 10^{11}$, $1 \times 10^{12}$, $5 \times 10^{12}$, $1 \times 10^{13}$ or more infectious viral particles or plaque forming units (pfu), including the various values and ranges there between. For example, the subject may be administered one or more doses of between about $1 \times 10^8$ and $1 \times 10^{12}$, between about $1 \times 10^8$ and $1 \times 10^{10}$, between about $1 \times 10^9$ and $1 \times 10^{12}$ or between $1 \times 10^9$ and $1 \times 10^{10}$ pfu of virus. In one aspect, a pharmaceutical composition comprising a pharmaceutically acceptable carrier and a single dose of at least $2 \times 10^8$, $5 \times 10^8$, $1 \times 10^9$ $2 \times 10^9$, $5 \times 10^9$, $1 \times 10^{10}$, $5 \times 10^{10}$, $1 \times 10^{11}$, $5 \times 10^{11}$, $1 \times 10^{12}$, $5 \times 10^{12}$, $1 \times 10^{13}$ or more infectious viral particles or plaque forming units (pfu), including the various values and ranges there between is administered one or more times to the subject. The viral dose can be administered in 0.1, 1, 2, 3, 4, 5, 6, 7, 8, 9, 10 or more mL, including all values and ranges there between. In one aspect, the dose is sufficient to generate a detectable level of GM-CSF in serum of the patient, e.g., at least about, at most about or about 5, 10, 40, 50, 100, 200, 500, 1,000, 5,000, 10,000, 15,000 to 20,000 pg/mL, including all values and ranges there between. It is contemplated that a single dose of virus refers to the amount administered to a subject or a tumor over a 1, 2, 5, 10, 15, 20, or 24 hour period. The dose may be spread over time or by separate injection. Typically, multiple doses are administered to the same general target region, such as in the proximity of a tumor or in the case of intravenous administration a particular entry point in the blood stream or lymphatic system of a subject. In certain aspects, the viral dose is delivered by injection apparatus comprising a needle providing multiple ports in a single needle or multiple prongs coupled to a syringe, or a combination thereof. In a further aspect, multiple doses (2, 3, 4, 5, 6 or more doses) of the vaccinia virus are administered to the subject, for example, wherein a second treatment occurs within 1, 2, 3, 4, 5, 6, 7 days or weeks of a first treatment, or wherein the second treatment occurs within 2 weeks of the first treatment. In a related aspect, multiple doses of the vaccinia virus are administered to the subject over a period of 1, 2, 3, 4, 5, 6, 7 or more days or weeks.

In certain embodiments the subject is a human. The subject may be afflicted with cancer and/or a tumor in which case the vaccinia virus vector is administered to treat the cancer and/or tumor. In certain embodiments the tumor may be non-resectable prior to treatment and resectable following treatment. In certain aspects the tumor is located on or in the liver. In other aspects, the tumor can be a brain cancer tumor, a head and neck cancer tumor, an esophageal cancer tumor, a skin cancer tumor, a lung cancer tumor, a thymic cancer tumor, a stomach cancer tumor, a colon cancer tumor, a liver cancer tumor, an ovarian cancer tumor, a uterine cancer tumor, a bladder cancer tumor, a testicular cancer tumor, a rectal cancer tumor, a breast cancer tumor, or a pancreatic cancer tumor. In other embodiments the tumor is a bladder tumor. In still further embodiments the tumor is melanoma. The tumor can be a recurrent, primary, metastatic, and/or multi-drug resistant tumor. In certain embodiments, the tumor is a hepatocellular tumor or a metastasized tumor originating from another tissue or location. In certain aspects the tumor is in the liver.

In certain aspects, the method further comprises administering to the subject a second cancer therapy. The second cancer therapy can be chemotherapy, biological therapy, radiotherapy, immunotherapy, hormone therapy, anti-vascular therapy, cryotherapy, toxin therapy and/or surgery, including combinations thereof. In a further aspect, the chemotherapy can be taxol or sorafenib. In still a further aspect, surgery includes the transarterial chemoembolization (TACE procedure, see Vogl et al., European Radiology 16(6):1393, 2005). The method may further comprise a second administration of the vaccinia virus vector. Methods of the invention can further comprise assessing tumor cell viability before, during, after treatment, or a combination thereof. In certain embodiments the virus is administered intravascularly, intratumorally, or a combination thereof. In a further aspect administration is by injection into a tumor mass. In still a further embodiment, administration is by injection into or in the region of tumor vasculature. In yet a further embodiment, administration is by injection into the lymphatic or vasculature system regional to said tumor. In certain aspects the method includes imaging the tumor prior to or during administration. In certain aspects, a patient is or is not pre-immunized with a vaccinia virus vaccine. In a further aspect, the subject can be immunocompromised, either naturally or clinically.

In certain aspects, the virus is administered in an amount sufficient to induce oncolysis in at least 20% of cells in an injected tumor, in at least 30% of cells in an injected tumor, in at least 30% of cells in an injected tumor, in at least 40% of cells in an injected tumor, in at least 50% of cells in an injected tumor, in at least 60% of cells in an injected tumor, in at least 70% of cells in an injected tumor, in at least 80% of cells in an injected tumor, or in at least 90% of cells in an injected tumor.

In certain embodiments, the vaccinia virus may have a mutation in a gene encoding (a) vaccinia virus growth factor; (b) a functional interferon-modulating polypeptide, wherein the interferon-modulating polypeptide directly binds interferon; (c) a complement control polypeptide, wherein the mutation results in the virus lacking at least one functional complement control polypeptide; (d) a TNF-modulating polypeptide, wherein the mutation results in the virus lacking at least one functional TNF-modulating polypeptide; (e) a serine protease inhibitor, wherein the mutation results in the virus lacking at least one functional serine protease inhibitor; (f) an IL-1β modulator polypeptide, wherein the mutation results in the virus lacking at least one functional IL-1β modulator polypeptide; (g) a functional A41L, B7R, N1L or vCKBP chemokine binding polypeptide or C11R EGF-like polypeptide, wherein the mutation results in the virus lacking at least one function of A41L, B7R, N1L, vCKBP, or C11R; or (h) a polypeptide, wherein the mutation results in an increase in infectious EEV form of vaccinia virus. The vaccinia virus may be the Wyeth or Western Reserve (WR) strain. The promoter may be a vaccinia virus promoter, a synthetic promoter, a promoter that directs transcription during at least the early phase of infection, or a promoter that directs transcription during at least the late phase of infection In related embodiments, the vaccinia virus comprises one or more modified viral genes. The one or more modified viral genes may comprise one or more of (a) an interferon-modulating polypeptide; (b) a complement control polypeptide; (c) a TNF or chemokine-modulating polypeptide; (d) a serine protease inhibitor; (e) a IL-1β modulating polypeptide; (f) a non-infectious EEV form polypeptide; (g) a viral polypeptide that act to inhibit release of infectious virus from cells (anti-infectious virus form polypeptide) or combinations thereof.

In another embodiment, there is provided a method for treating cancer in a subject or treating one or more metastases in a subject comprising administering to the subject at least $1 \times 10^8$ infective viral particles of a TK-deficient replicative vaccinia virus having an expression region with a promoter directing expression of a nucleic acid encoding granulocyte-macrophage colony stimulating factor (GM-CSF). In related embodiments, the administration is intravascular.

In other embodiments, it is contemplated that methods involving a replication-competent vaccinia virus may contain a nucleic acid encoding a protein or RNA other than GM-CSF. In particular embodiments, the nucleic acid encodes another cytokine. In certain embodiments, the nucleic acid encodes other immunostimulatory cytokines or chemokines, such as IL-12, IL-2 and others. In additional embodiments, the nucleic acid may encode thymidine deaminase or tumor necrosis factor (TNF), such as TNF-α. Moreover, it is contemplated that replicative vaccinia viruses may express more than one heterologous sequence. It may express, for example, GM-CSF protein and another protein or RNA molecule.

Embodiments of the invention target common, critical cancer pathways. Targeting these pathways involves the modulation of various cellular mechanisms (e.g., cellular thymidine kinase levels: E2F-responsive; EGF-R pathway activation; immune sanctuary: anti-viral IFN response (ras, p53); VEGF-induced vascular pore size: deposition IV) leading to multiple efficacy mechanisms, such as oncolysis: necrosis, vascular shut-down, CTL attack induction, systemic: IT, IV; tumor-specific CTLs.

Embodiments of the invention build on phase I clinical trials demonstrating safety and efficacy of vaccinia virus as a cancer treatment. A metastatic melanoma clinical trial with seven patients with a median life expectancy <6 months enrolled were conducted using intratumoral injections in a bi-weekly dose escalation study. The trial indicated that vaccinia virus was safe, well-tolerated and resulted in tumor responses in 5 patients (71%) with two long-term survivors disease-free.

Initial results from phase I/II trials have also demonstrated continued safety of JX-594. Flu-like symptoms were observed for 5-8 days. A transient decrease platelets (plt), lymph, absolute neutrophil count (ANC) (typically Gr1-2) was also observed. There was one death on study Day 8, but was determined not to be related to treatment. Overall, JX-594 viremia was well-tolerated with an immediate post-injection (15-30 min.): max $3 \times 10^8$ total genomes in blood and a replication peak (Day 5-8): max $10^{10}$ total genomes in blood.

Other embodiments of the invention are discussed throughout this application. Any embodiment discussed with respect to one aspect of the invention applies to other aspects of the invention as well and vice versa. The embodiments in the Example section are understood to be embodiments of the invention that are applicable to all aspects of the invention.

The terms "inhibiting," "reducing," or "prevention," or any variation of these terms, when used in the claims and/or the specification includes any measurable decrease or complete inhibition to achieve a desired result.

The use of the word "a" or "an" when used in conjunction with the term "comprising" in the claims and/or the specification may mean "one," but it is also consistent with the meaning of "one or more," "at least one," and "one or more than one."

It is contemplated that any embodiment discussed herein can be implemented with respect to any method or composition of the invention, and vice versa. Furthermore, compositions and kits of the invention can be used to achieve methods of the invention.

Throughout this application, the term "about" is used to indicate that a value includes the standard deviation of error for the device or method being employed to determine the value.

The use of the term "or" in the claims is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

(FIG. 2A) Subsequent tumor volume in the liver was measured 7 weeks later by CT scan and (FIG. 2B) number of detectable tumor metastases in the lungs were counted following CT scan at weeks 6 and 7.

FIGS. 6A-6C—Burst ratio of vaccinia strains, cytopathic effect, and systemic delivery of viral strains to tumors. (FIG. 6A) Burst ratio of vaccinia strains in tumor to normal cells. Different vaccinia strains were used to infect both primary normal cells (NHBE) and a tumor cell line (A2780) at a Multiplicity of infection (MOI) of 1.0 Plaque Forming Unit (PFU)/cell. Virus collected 48 h later was titered by plaque assay and the ratio of virus produced (per cell) in tumor to normal cells is represented. (FIG. 6B) Cytopathic effect produced by viral infection. Western Reserve, Adenovirus serotype 5 and Adenovirus strain dl 1520 (ONYX-015) (in some assays) were added to cell lines at ranges of MOIs (PFU/cell), and cell viability measured after 72 hours using MTS (Promega). The MOI of virus (PFU/cell) needed to reduce the cell viability to 50% of untreated control wells (ED$_{50}$) is plotted. (FIG. 6C) Systemic delivery of viral strains to tumors. 1×10$^9$ PFU of vaccinia strain Western Reserve or Adenovirus serotype 5 were delivered intravenously to immunocompetent mice bearing subcutaneous CMT 64 or JC tumors. Mice were sacrificed after 48 or 72 hours and immunohistochemistry performed against viral coat proteins on paraffin embedded sections of tumor tissue. Graphs show scoring of positive cells in each tumour (*=none detectable). For each condition results are based on tumours from 3 mice, and for each tumour, ten randomly chosen fields of view were scored.

(FIG. 7A) Effects of overexpression of H-Ras on viral replication. NIH 3T3 cells, and NIH 3T3 cells expressing activated H-Ras, either proliferating or serum starved, were infected with different strains of vaccinia at an MOI of 1.0 PFU/cell. Viral strains were parental Western Reserve (WR), and WR containing deletions or insertions in either the Thymidine Kinase (TK) gene (vJS6), the viral growth factor (VGF) gene (vSC20), or containing deletions in both these genes (vvDD). Infectious virus was titered by plaque assay after 48 h. (FIG. 7B). Biodistribution of WR and vvDD following systemic delivery to tumor bearing mice. Athymic CD1 nu/nu mice bearing subcutaneous human HCT 116 tumors (arrowed) were treated with 1×10$^7$ PFU of vaccinia strains via tail vein injection. Viral strains (WR and vvDD) expressed luciferase, and the subsequent biodistribution of viral gene expression was detected by bioluminescence imaging in an IVIS100 system (Xenogen Corp, Alameda) following addition of the substrate luciferin at the times indicated after treatment. (FIG. 7C) Viral gene expression, as quantified by light production, was plotted over time for the regions of interest covering the whole body (ventral image)(dashed line, open symbols), or from the tumor only (dorsal view)(solid line, filled symbols) for BALB/c mice bearing subcutaneous JC tumors (n=5 mice/group) and treated with 1×10$^7$ PFU of either virus by tail vein injection.

FIGS. 9A-9C—Rabbits bearing VX2 tumors implanted into the liver were followed by CT imaging at times after tumor implantation, CTL assay against VX2 tumor cells, and Rabbits re-treated with JX-963. (FIG. 9A) Rabbits bearing VX2 tumors implanted into the liver were followed by CT imaging at times after tumor implantation. 1×10$^9$ PFU of viruses vvDD and JX-963 were delivered by ear vein injection at 2, 3 and 4 weeks after tumor implantation (arrows), when tumors measured 5 cm3. The number of detectable lung metastases was also measured in these animals (representative CT images of primary liver tumors are shown at 8 weeks) (n=18 for control treated animals; n=6 for vvDD treated; n=6 for JX-963 treated). (FIG. 9B) CTL assay targeting VX2 tumor cells. CTL assay was performed by FACS analysis using pre-labeled VX2 cells mixed with 12.5×; 25× and 50× unlabelled peripheral blood lymphocytes from rabbits bearing VX2 tumors and treated with JX-963; from untreated animals with VX2 tumors; and from naïve animals. Cell death was quantified by the ACT1 assay (Cell Technology, Mountain View). (FIG. 9C) Four Rabbits treated as in (A) with JX-963 were re-treated with 1×10$^9$ PFU of JX-963 at Day 42 after implantation (arrow), subsequent tumor volume was followed by CT scan.

(FIG. 10A) Different cell lines were infected with either Western Reserve or Adenovirus serotype 5 at an MOI of 1.0 PFU/cell. Amounts of virus produced (Infectious Units/cell) 48 h later were titered by plaque assay. (FIG. 10B) Mice treated as in FIG. 1C were sacrificed and tumor sections stained for viral coat proteins. Representative photographs show sections at 72 h and 10 days post-treatment.

(FIG. 13A) Single intravenous injections of $1 \times 10^9$ PFU of viral strain vvDD or vaccinia Wyeth strain bearing a Thymidine Kinase deletion were delivered to immunocompetent mice bearing subcutaneous TIB 75 tumors (50-100 mm$^3$). Tumor volume was measured by calipers, (n=8/group). (FIG. 13B) $1 \times 10^9$ PFU of vvDD was delivered intratumorally (IT) or intraperitoneally (IP) to either SCID mice bearing subcutaneous HT29 tumors or C57B/6 mice bearing subcutaneous MC38 tumors and subsequent tumor volume compared to an uninfected control group (n=8/group).

FIG. 15. Clinical trial study design for hepatic tumors using JX-594 by intratumoral injection.

FIG. 16. Clinical trial study design for melanoma using JX-594 by intratumoral injection.

FIG. 20. JX594-IT-hep001—patient demographics and treatment status—cohort 1 and 2.

FIG. 21. JX594-IT-hep001—patient demographics and treatment status—cohort 3.

FIG. 23. Replication viremia of JX-594 evident in 80% of patients: Secondary wave of JX-594 in blood demonstrated in cycles 1-7. (+) after input dose cleared, (−) Level below limit detection, squares=patient off-study, and (p)=data pending. Limit of detection=700 genomes/ml.

FIG. 33. Treatment, Efficacy and Survival Data: Tumor responses by CT and PET, long-term survivors.

FIGS. 36A-36C. Changes in hematologic tests. (A) Dose-dependent thrombocytopenia. (B) Magnitude of thrombocytopenia is cycle-independent. (C) Magnitude of changes of in ANC, eosinophils, and monocytes were more significant in cycle 1 compared to subsequent cycles. White bars: ANC; grey bars: eosinophils; black bars: monocytes. Error bars represent standard error of the mean.

DETAILED DESCRIPTION OF THE INVENTION

Figure 1:
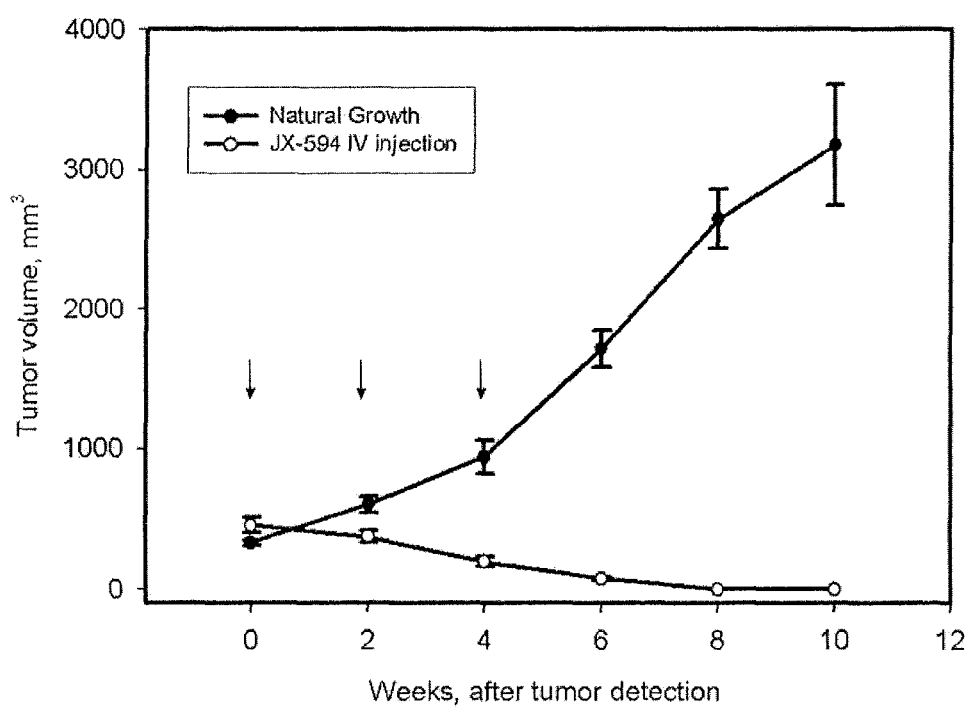
FIG. 1—JX-594 intravenous (IV) treatment of spontaneous rat hepatocellular carcinoma (HCC). Rats received the mutagen N-Nitrosomorpholine (NMM) in their drinking water (175 mg/L) for a period of 8 weeks and were then followed by ultrasound (US) until HCC tumors had formed and were 300-400 mm$^3$ (typically after 16-20 weeks). Animals then received 3 intravenous doses (one every two weeks, arrows) of either PBS (n=17) or 1×10$^8$ PFU of JX-594 virus (n=6). Subsequent tumor volumes were then calculated based on tumor measurements from US imaging.

The present invention concerns the use of oncolytic poxviruses for the treatment of cancer. In particular, the use of a vaccinia virus expressing GM-CSF to achieve a particular degree of oncolysis is described. In another embodiment, a GM-CSF-expressing poxvirus can be engineered to be more effective or more efficient at killing cancer cells and/or be less toxic or damaging to non-cancer cells, by mutation or modification of gene products such that the alterations render the viruses better able to infect the host, less toxic to host cells, and/or better able to infect cancer cells. A particular modification is to render the virus deficient in thymidine kinase (TK) function.

The present invention also concerns the intravenous administration of GM-CSF-expressing poxviruses to treat both primary tumors and distant metastases. The inventors have demonstrated that two different GM-CSF-expressing poxviruses were well-tolerated intravenously and highly effective against disseminated tumors and metastases. In addition, a GM-CSF-expressing poxvirus had significantly better efficacy against both primary tumors and lung metastases than its non-GM-CSF-expressing control after intravenous administration. Also, this virus had significantly better efficacy against both primary tumors and lung metastases than a comparable virus (Wyeth vaccine strain) despite an additional deletion in the vgf gene not present in the other virus. Therefore, intravenous administration with a vaccinia expressing human GM-CSF resulted in significantly better efficacy over the same vaccinia without GM-CSF, and intravascular administration of a WR strain deletion mutant expressing human GM-CSF was significantly better than a standard vaccine strain expressing GM-CSF. These viruses were well-tolerated after intravenous administration to both tumor-bearing (rats and rabbits) and normal animals (rabbits). Treated animals did not lose weigh while tumor-bearing animals that did not receive treatment lost weight. Survival was increased following intravenous treatment. No significant organ toxicity was noted by blood testing or histopathology. The only reproducible histopathological findings were multiple sites of lymphoid hyperplasia that were noted following treatment (consistent with systemic immunostimulation). No significant toxicities were noted on histopathology. Therefore, these GM-CSF expressing poxviruses are well-tolerated at doses that were highly effective against systemic cancer.

I. Poxviruses

Poxviruses have been known for centuries, with the characteristic pock marks produced by variola virus (smallpox) giving this family its name. It appears that smallpox first emerged in China and the Far East over 2000 years ago. Fortunately, this often fatal virus has now been eradicated, with the last natural outbreak occurring in 1977 in Somalia.

The poxvirus viral particle is oval or brick-shaped, measuring some 200-400 nm long. The external surface is ridged in parallel rows, sometimes arranged helically. The particles are extremely complex, containing over 100 distinct proteins. The extracellular forms contain two membranes (EEV—extracellular enveloped virions), whereas intracellular particles only have an inner membrane (IMV—intracellular mature virions). The outer surface is composed of lipid and protein that surrounds the core, which is composed of a tightly compressed nucleoprotein. Antigenically, poxviruses are also very complex, inducing both specific and cross-reacting antibodies. There are at least ten enzymes present in the particle, mostly concerned with nucleic acid metabolism/genome replication.

The genome of the poxvirus is linear double-stranded DNA of 130-300 Kbp. The ends of the genome have a terminal hairpin loop with several tandem repeat sequences. Several poxvirus genomes have been sequenced, with most of the essential genes being located in the central part of the genome, while non-essential genes are located at the ends. There are about 250 genes in the poxvirus genome.

Replication takes place in the cytoplasm, as the virus is sufficiently complex to have acquired all the functions necessary for genome replication. There is some contribution by the cell, but the nature of this contribution is not clear. However, even though poxvirus gene expression and genome replication occur in enucleated cells, maturation is blocked, indicating some role by the cell.

The receptors for poxviruses are not generally known, but probably are multiple in number and on different cell types. For vaccinia, one of the likely receptors is EGF receptor (McFadden, 2005). Penetration may also involve more than one mechanism. Uncoating occurs in two stages: (a) removal of the outer membrane as the particle enters the cell and in the cytoplasm, and (b) the particle is further uncoated and the core passes into the cytoplasm.

Once into the cell cytoplasm, gene expression is carried out by viral enzymes associated with the core. Expression is divided into 2 phases: early genes: which represent about of 50% genome, and are expressed before genome replication, and late genes, which are expressed after genome replication. The temporal control of expression is provided by the late promoters, which are dependent on DNA replication for activity. Genome replication is believed to involve self-priming, leading to the formation of high molecular weight concatemers, which are subsequently cleaved and repaired to make virus genomes. Viral assembly occurs in the cytoskeleton and probably involves interactions with the cytoskeletal proteins (e.g., actin-binding proteins). Inclusions form in the cytoplasm that mature into virus particles. Cell to cell spread may provide an alternative mechanism for spread of infection. Overall, replication of this large, complex virus is rather quick, taking just 12 hours on average.

At least nine different poxviruses cause disease in humans, but variola virus and vaccinia are the best known. Variola strains are divided into variola major (25-30% fatalities) and variola minor (same symptoms but less than 1% death rate). Infection with both viruses occurs naturally by the respiratory route and is systemic, producing a variety of symptoms, but most notably with variola characteristic pustules and scarring of the skin.

A. Vaccinia Virus

Vaccinia virus is a large, complex enveloped virus having a linear double-stranded DNA genome of about 190K http://www.answers.com/topic/base-pair by and encoding for approximately 250 genes. Vaccinia is well-known for its role as a vaccine that eradicated smallpox. Post-eradication of smallpox, scientists have been exploring the use of vaccinia as a tool for delivering genes into biological tissues (gene therapy and genetic engineering). Vaccinia virus is unique among DNA viruses as it replicates only in the cytoplasm of the host cell. Therefore, the large genome is required to code for various enzymes and proteins needed for viral DNA replication. During replication, vaccinia produces several infectious forms which differ in their outer membranes: the intracellular mature virion (IMV), the intracellular enveloped virion (IEV), the cell-associated enveloped virion (CEV) and the extracellular enveloped virion (EEV). IMV is the most abundant infectious form and is thought to be responsible for spread between hosts. On the other hand, the CEV is believed to play a role in cell-to-cell spread and the EEV is thought to be important for long range dissemination within the host organism.

Vaccinia encodes several proteins giving the virus resistance to interferons. K3L is a protein having homology with eIF-2α. K3L protein inhibits the action of PKR, an activator of interferons. E3L is another vaccinia protein that also inhibits PKR activation and is also able to bind double-stranded RNA.

Vaccinia virus is closely related to the virus that causes cowpox. The precise origin of vaccinia is unknown, but the most common view is that vaccinia virus, cowpox virus, and variola virus (the causative agent for smallpox) were all derived from a common ancestral virus. There is also speculation that vaccinia virus was originally isolated from horses. A vaccinia virus infection is mild and typically asymptomatic in healthy individuals, but it may cause a mild rash and fever, with an extremely low rate of fatality. An immune response generated against a vaccinia virus infection protects that person against a lethal smallpox infection. For this reason, vaccinia virus was used as a live-virus vaccine against smallpox. The vaccinia virus vaccine is safe because it does not contain the smallpox virus, but occasionally certain complications and/or vaccine adverse effects may arise, especially if the vaccine is immunocompromised.

As discussed above, vaccinia viruses have been engineered to express a number of foreign proteins. One such protein is granulocyte-macrophage colony stimulating factor, or GM-CSF. GM-CSF is a protein secreted by macrophages that stimulates stem cells to produce granulocytes (neutrophils, eosinophils, and basophils) and macrophages. Human GM-CSF is glycosylated at amino acid residues 23 (leucine), 27 (asparagine), and 39 (glutamic acid) (see U.S. Pat. No. 5,073,627, incorporated by reference). GM-CSF is also known as molgramostim or, when the protein is expressed in yeast cells, sargramostim (trademarked Leukine®), which is used as a medication to stimulate the production of white blood cells, especially granulocytes and macrophages, following chemotherapy. A vaccinia virus expressing GM-CSF has previously been reported. However, it was delivered not as an oncolytic agent, but merely as a delivery vector for GM-CSF. As such, it has been administered to patients at dosage below that which can achieve significant oncolysis. Herein is described the use of a GM-CSF expressing vaccinia virus that, in some embodiments, is administered at concentrations greater than $1 \times 10^8$ pfu or particles.

B. Modified Poxviruses

Viruses are frequently inactivated, inhibited, or cleared by immunomodulatory molecules such as interferons (-α, -β, -γ) and tumor necrosis factor-α (TNFα) (Moss, 1996). Host tissues and inflammatory/immune cells frequently secrete these molecules in response to viral infection. These molecules can have direct antiviral effects and/or indirect effects through recruitment and/or activation of inflammatory cells and lymphocytes. Given the importance of these immunologic clearance mechanisms, viruses have evolved to express gene products that inhibit the induction and/or function of these cytokines/chemokines and interferons. For example, vaccinia virus (VV, and some other poxviruses) encodes the secreted protein vCKBP (B29R) that binds and inhibits the CC chemokines (e.g., RANTES, eotaxin, MIP-1-alpha) (Alcami et al., 1998). Some VV strains also express a secreted viral protein that binds and inactivates TNF (e.g., Lister A53R) (Alcami et al., 1999). Most poxvirus strains have genes encoding secreted proteins that bind and inhibit the function of interferons-α/β (e.g., B18R) or interferon (B8R). vC12L is an IL-18-binding protein that prevents IL-18 from inducing IFN-γ and NK cell/cytotoxic T-cell activation.

Most poxvirus virulence research has been performed in mice. Many, but not all, of these proteins are active in mice (B18R, for example, is not). In situations in which these proteins are active against the mouse versions of the target cytokine, deletion of these genes leads to reduced virulence and increased safety with VV mutants with deletions of or functional mutations in these genes. In addition, the inflammatory/immune response to and viral clearance of these mutants is often increased compared to the parental virus strain that expresses the inhibitory protein. For example, deletion of the T1/35 kDa family of poxvirus-secreted proteins (chemokine-binding/-inhibitory proteins) can lead to a marked increase in leukocyte infiltration into virus-infected tissues (Graham et al., 1997). Deletion of the vC12L gene in VV leads to reduced viral titers/toxicity following intranasal administration in mice; in addition, NK cell and cytotoxic T-lymphocyte activity is increased together with IFN-γ induction (Smith et al., 2000). Deletion of the Myxoma virus T7 gene (able to bind IFN-γ and a broad range of chemokines) results in reduced virulence and significantly increased tissue inflammation/infiltration in a toxicity model (Upton et al., 1992; Mossman et al., 1996). Deletion of the M-T2 gene from myxoma virus also resulted in reduced virulence in a rabbit model (Upton et al. 1991). Deletion of the B18R anti-interferon-α/-β gene product also leads to enhanced viral sensitivity to IFN-mediated clearance, reduced titers in normal tissues and reduced virulence (Symons et al., 1995; Colamonici et al., 1995; Alcami et al., 2000). In summary, these viral gene products function to decrease the antiviral immune response and inflammatory cell infiltration into virus-infected tissues. Loss of protein function through deletion/mutation leads to decreased virulence and/or increased proinflammatory properties of the virus within host tissues.

Cytokines and chemokines can have potent antitumoral effects (Vicari et al., 2002; Homey et al., 2002). These effects can be on tumor cells themselves directly (e.g., TNF) or they can be indirect through effects on non-cancerous cells. An example of the latter is TNF, which can have antitumoral effects by causing toxicity to tumor-associated blood vessels; this leads to a loss of blood flow to the tumor followed by tumor necrosis. In addition, chemokines can act to recruit (and in some cases activate) immune effector cells such as neutrophils, eosinophils, macrophages and/or lymphocytes. These immune effector cells can cause tumor destruction by a number of mechanisms. These mechanisms include the expression of antitumoral cytokines (e.g., TNF), expression of fas-ligand, expression of perforin and granzyme, recruitment of natural killer cells, etc. The inflammatory response can eventually lead to the induction of systemic tumor-specific immunity. Finally, many of these cytokines (e.g., TNF) or chemokines can act synergistically with chemotherapy or radiation therapy to destroy tumors.

Clinically effective systemic administration of recombinant versions of these immunostimulatory proteins is not feasible due to (1) induction of severe toxicity with systemic administration and (2) local expression within tumor tissue is needed to stimulate local infiltration and antitumoral effects. Approaches are needed to achieve high local concentrations of these molecules within tumor masses while minimizing levels in the systemic circulation. Viruses can be engineered to express cytokine or chemokine genes in an attempt to enhance their efficacy. Expression of these genes from replication-selective vectors has potential advantages over expression from non-replicating vectors. Expression from replicating viruses can result in higher local concentrations within tumor masses; in addition, replicating viruses can help to induce antitumoral immunity through tumor cell destruction/oncolysis and release of tumor antigens in a proinflammatory environment. However, there are several limitations to this approach. Serious safety concerns arise from the potential for release into the environment of a replication-competent virus (albeit tumor-selective) with a gene that can be toxic if expressed in high local concentrations. Viruses that express potent pro-inflammatory genes from their genome may therefore pose safety risks to the treated patient and to the general public. Even with tumor-targeting, replication-selective viruses expressing these genes, gene expression can occur in normal tissues resulting in toxicity. In addition, size limitations prevent expression of multiple and/or large genes from viruses such as adenovirus; these molecules will definitely act more efficaciously in combination. Finally, many of the oncolytic viruses in use express anti-inflammatory proteins and therefore these viruses will counteract the induction of a proinflammatory milieu within the infected tumor mass. The result will be to inhibit induction of antitumoral immunity, antivascular effects and chemotherapy-/radiotherapy-sensitization.

C. Modified Vaccinia Virus

1. Interferon-Modulating Polypeptides

Interferon-$\alpha$/-$\beta$ blocks viral replication through several mechanisms. Interferon-$\gamma$ has weaker direct viral inhibitory effects but is a potent inducer of cell-mediated immunity through several mechanisms. Viruses have evolved to express secreted gene products that are able to counteract the antiviral effects of interferons. For example, vaccinia virus (and other poxviruses) encodes the secreted proteins B8R and B18R which bind interferon-$\gamma$ and -$\alpha$/-$\beta$, respectively (Smith et al., 1997; Symons et al., 1995; Alcami et al., 2000). An additional example of a vaccinia gene product that reduces interferon induction is the caspase-1 inhibitor B13R which inhibits activation of the interferon-$\gamma$-inducing factor IL-18. Interferon modulating polypeptides include, but are not limited to, B18R, which may be termed B19R in other viral strains, such as the Copenhagen strain of vaccinia virus; B8R; B13R; vC12L; A53R; E3L and other viral polypeptides with similar activities or properties. IFN modulating polypeptides may be divided into the non-exclusive categories of those that preferentially modulate IFN$\alpha$ and/or $\beta$ pathways (such as B18R, B8R, B13R, or vC12L) and those that modulate IFN$\gamma$ pathways (for example B8R, B13R, or vC12L).

Cancer cells are frequently resistant to the effects of interferons. A number of mechanisms are involved. These include the fact that ras signal transduction pathway activation (e.g., by ras mutation, upstream growth factor receptor overexpression/mutation, etc.), a common feature of cancer cells, leads to PKR inhibition. In addition, lymphocytes are often inhibited in tumor masses by a variety of mechanisms including IL-10 production and fas-L expression by tumor cells. Since lymphocytes are a major source of interferon-$\gamma$ production, lymphocyte inhibition leads to a decrease in interferon-$\gamma$ production in tumors. Therefore, tumor masses tend to be sanctuaries from the effects of interferons. In addition, interferons themselves can have antitumoral effects. For example, IFN-$\gamma$ can increase MHC class-I-associated antigen presentation; this will allow more efficient CTL-mediated killing of tumor cells. IFN-$\alpha$/$\beta$, for example, can block angiogenesis within tumor masses and thereby block tumor growth.

2. Complement Control Polypeptides

A major mechanism for the clearance of viral pathogens is the killing of infected cells within the host or of virions within an organism by complement-dependent mechanisms. As the infected cell dies it is unable to continue to produce infectious virus. In addition, during apoptosis intracellular enzymes are released which degrade DNA. These enzymes can lead to viral DNA degradation and virus inactivation. Apoptosis can be induced by numerous mechanisms including the binding of activated complement and the complement membrane attack complex. Poxviruses such as vaccinia have evolved to express gene products that are able to counteract the complement-mediated clearance of virus and/or virus-infected cells. These genes thereby prevent apoptosis and inhibit viral clearance by complement-dependent mechanisms, thus allowing the viral infection to proceed and viral virulence to be increased. For example, vaccinia virus complement control proteins (VCP; e.g., C21L) have roles in the prevention of complement-mediated cell killing and/or virus inactivation (Isaacs et al., 1992). VCP also has anti-inflammatory effects since its expression decreases leukocyte infiltration into virally-infected tissues. Complement control polypeptides include, but are not limited to, VCP, also known as C3L or C21L.

Cancer cells frequently overexpress cellular anti-complement proteins; this allows cancer cells to survive complement attack. Therefore, agents that preferentially target tumor cells due to their inherent resistance to complement-mediated killing would have selectivity and potential efficacy in a wide range of human cancers (Durrant et al., 2001). In addition, one of the hallmarks of cancer cells is a loss of normal apoptotic mechanisms (Gross et al., 1999). Resistance to apoptosis promotes carcinogenesis as well as resistance to antitumoral agents including immunologic, chemotherapeutic and radiotherapeutic agents (Eliopoulos et al., 1995). Apoptosis inhibition can be mediated by a loss of pro-apoptotic molecule function (e.g., bax), an increase in the levels/function of anti-apoptotic molecules (e.g., bcl-2) and finally a loss of complement sensitivity.

3. TNF-Modulating Polypeptides

One of the various mechanisms for the clearance of viral pathogens is the killing of infected cells within the host by the induction of apoptosis, as described above. Apoptosis can be induced by numerous mechanisms including the binding of TNF and lymphotoxin-alpha (LT$\alpha$) to cellular TNF receptors, which triggers intracellular signaling cascades. Activation of the TNF receptors function in the regulation of immune and inflammatory responses, as well as inducing apoptotic cell death (Wallach et al., 1999)

Various strains of poxviruses, including some vaccinia virus strains, have evolved to express gene products that are able to counteract the TNF-mediated clearance of virus and/or virus-infected cells. The proteins encoded by these genes circumvent the proinflammatory and apoptosis inducing activities of TNF by binding and sequestering extracellular TNF, resulting in the inhibition of viral clearance. Because viruses are not cleared, the viral infection is allowed to proceed, and thus, viral virulence is increased. Various members of the poxvirus family express secreted viral TNF receptors (vTNFR). For example, several poxviruses encode vTNFRs, such as myxoma (T2 protein), cowpox and vaccinia virus strains, such as Lister, may encode one or more of the CrmB, CrmC (A53R), CrmD, CrmE, B28R proteins and/or equivalents thereof. These vTNFRs have roles in the prevention of TNF-mediated cell killing and/or virus inactivation (Saraiva and Alcami, 2001). TNF modulatory polypeptides include, but are not limited to, A53R, B28R (this protein is present, but may be inactive in the Copenhagen strain of vaccinia virus) and other polypeptides with similar activities or properties.

One of the hallmarks of cancer cells is aberrant gene expression, which may lead to a loss of sensitivity to a number of molecular mechanisms for growth modulation, such as sensitivity to the anti-cancer activities of TNF. Thus, viral immunomodulatory mechanisms may not be required for the propagation of a virus within the tumor microenvironment.

4. Serine Protease Inhibitors

A major mechanism for the clearance of viral pathogens is the induction of apoptosis in infected cells within the host. As the infected cell dies it is unable to continue to produce infectious virus. In addition, during apoptosis intracellular enzymes are released which degrade DNA. These enzymes can lead to viral DNA degradation and virus inactivation. Apoptosis can be induced by numerous mechanisms including the binding of cytokines (e.g., tumor necrosis factor), granzyme production by cytotoxic T-lymphocytes or fas-ligand binding; caspase activation is a critical part of the final common apoptosis pathway. Viruses have evolved to express gene products that are able to counteract the intracellular signaling cascade induced by such molecules including fas-ligand or tumor necrosis factor (TNF)/TNF-related molecules (e.g., E3 10.4/14.5, 14.7 genes of adenovirus (Wold et al., 1994); E1B-19kD of adenovirus (Boyd et al., 1994); crmA from cowpoxvirus; B13R from vaccinia virus) (Dobbelstein et al., 1996; Kettle et al., 1997)). These gene products prevent apoptosis by apoptosis-inducing molecules and thus allow viral replication to proceed despite the presence of antiviral apoptosis-inducing cytokines, fas, granzyme or other stimulators of apoptosis.

VV SPI-2/B13R is highly homologous to cowpox CrmA; SPI-1 (VV) is weakly homologous to CrmA (Dobbelstein et al., 1996). These proteins are serpins (serine protease inhibitors) and both CrmA and SPI-2 have roles in the prevention of various forms of apoptosis. Inhibition of interleukin-1β-converting enzyme (ICE) and granzyme, for example, can prevent apoptosis of the infected cell. These gene products also have anti-inflammatory effects. They are able to inhibit the activation of IL-18 which in turn would decrease IL-18-mediated induction of IFN-γ. The immunostimulatory effects of IFN-γ on cell-mediated immunity are thereby inhibited (Kettle et al., 1997). SPIs include, but are not limited to, B13R, B22R, and other polypeptides with similar activities or properties.

One of the hallmarks of cancer cells is a loss of normal apoptotic mechanisms (Gross et al., 1999). Resistance to apoptosis promotes carcinogenesis as well as resistance to antitumoral agents including immunologic, chemotherapeutic and radiotherapeutic agents (Eliopoulos et al., 1995). Apoptosis inhibition can be mediated by a loss of pro-apoptotic molecule function (e.g., bax) or an increase in the levels/function of anti-apoptotic molecules (e.g., bcl-2).

5. IL-1β-Modulating Polypeptides

IL-1β is a biologically active factors that acts locally and also systemically. Only a few functional differences between IL-1β and IL-1α have been described. The numerous biological activities of IL-1β is exemplified by the many different acronyms under which IL-1 has been described. IL-1 does not show species specificity with the exception of human IL-1β that is inactive in porcine cells. Some of the biological activities of IL-1 are mediated indirectly by the induction of the synthesis of other mediators including ACTH (Corticotropin), PGE2 (prostaglandin E2), PF4 (platelet factor4), CSF (colony stimulating factors), IL-6, and IL-8. The synthesis of IL-1 may be induced by other cytokines including TNF-α, IFN-α, IFN-β and IFN-γ and also by bacterial endotoxins, viruses, mitogens, and antigens. The main biological activity of IL-1 is the stimulation of T-helper cells, which are induced to secrete IL-2 and to express IL-2 receptors. Virus-infected macrophages produce large amounts of an IL-1 inhibitor that may support opportunistic infections and transformation of cells in patients with T-cell maturation defects. IL-1 acts directly on B-cells, promoting their proliferation and the synthesis of immunoglobulins. IL-1 also functions as one of the priming factors that makes B-cells responsive to IL-5. IL-1 stimulates the proliferation and activation of NK-cells and fibroblasts, thymocytes, glioblastoma cells.

Blockade of the synthesis of IL-1β by the viral protein is regarded as a viral strategy allowing systemic antiviral reactions elicited by IL-1 to be suppressed or diminished. Binding proteins effectively blocking the functions of IL-1 with similar activity as B1 5R have been found also to be encoded by genes of the cowpox virus. Vaccinia virus also encodes another protein, designated B8R, which behaves like a receptor for cytokines (Alcami and Smith, 1992; Spriggs et al., 1992). IL-1 modulating polypeptides include, but are not limited to, B13R, B15R, and other polypeptides with similar activities or properties.

One of the hallmarks of cancer cells is aberrant gene expression, which may lead to a loss of sensitivity to a number of molecular mechanisms for growth modulation, such as sensitivity to the anti-cancer activities of IL-1. Thus, viral immunomodulatory mechanisms may not be required for the propagation of a virus within the tumor microenvironment.

6. EEV Form

Viral spread to metastatic tumor sites, and even spread within an infected solid tumor mass, is generally inefficient (Heise et al., 1999). Intravenous administration typically results in viral clearance or inactivation by antibodies (e.g., adenovirus) (Kay et al., 1997) and/or the complement system (e.g., HSV) (Ikeda et al., 1999). In addition to these immune-mediated mechanisms, the biodistribution of these viruses results in the vast majority of intravenous virus depositing within normal tissues rather than in tumor masses. Intravenous adenovirus, for example, primarily ends up within the liver and spleen; less than 0.1% of the input virus depositing within tumors, even in immunodeficient mice (Heise et al., 1999). Therefore, although some modest antitumoral efficacy can be demonstrated with extremely high relative doses in immunodeficient mouse tumor models, intravenous delivery is extremely inefficient and significantly limits efficacy.

Vaccinia virus has the ability to replicate within solid tumors and cause necrosis. In addition, thymidine kinase-deletion mutants can infect tumor masses and ovarian tissue and express marker genes preferentially in mouse tumor model systems (Gnant et al., 1999). However, since these studies generally determined tumor targeting based on marker gene expression after 5 days, it is unclear whether the virus preferentially deposits in, expresses genes in or replicates in tumor/ovary tissue (Puhlmann et al., 2000). Regardless of the mechanism, the anti-tumoral efficacy of this virus without additional transgenes was not statistically significant (Gnant et al., 1999). In contrast, intratumoral virus injection had significant anti-tumoral efficacy (McCart et al. 2000). Therefore, i.v. efficacy could be improved if i.v. delivery to the tumor were to be improved.

Vaccinia virus replicates in cells and produces both intracellular virus (IMV, intracellular mature virus; IEV, intracellular enveloped virus) and extracellular virus (REV, extracellular enveloped virus; CEV, cell-associated extracellular virus) (Smith et al., 1998). IMV represents approximately 99% of virus yield following replication by wild-type vaccinia virus strains. This virus form is relatively stable in the environment, and therefore it is primarily responsible for spread between individuals; in contrast, this virus does not spread efficiently within the infected host due to inefficient release from cells and sensitivity to complement and/or antibody neutralization. In contrast, EEV is released into the extracellular milieu and typically represents only approximately 1% of the viral yield (Smith et al., 1998). EEV is responsible for viral spread within the infected host and is relatively easily degraded outside of the host. Importantly, EEV has developed several mechanisms to inhibit its neutralization within the bloodstream. First, EEV is relatively resistant to complement (Vanderplasschen et al., 1998); this feature is due to the incorporation of host cell inhibitors of complement into its outer membrane coat plus secretion of Vaccinia virus complement control protein (VCP) into local extracellular environment. Second, EEV is relatively resistant to neutralizing antibody effects compared to IMV (Smith et al., 1997). EEV is also released at earlier time points following infection (e.g., 4-6 hours) than is IMV (which is only released during/after cell death), and therefore spread of the EEV form is faster (Blasco et al., 1993).

Unfortunately, however, wild-type vaccinia strains make only very small amounts of EEV, relatively. In addition, treatment with vaccinia virus (i.e., the input dose of virus) has been limited to intracellular virus forms to date. Standard vaccinia virus (VV) manufacturing and purification procedures lead to EEV inactivation (Smith et al., 1998), and non-human cell lines are frequently used to manufacture the virus; EEV from non-human cells will not be protected from complement-mediated clearance (complement inhibitory proteins acquired from the cell by EEV have species restricted effects). Vaccinia virus efficacy has therefore been limited by the relative sensitivity of the IMV form to neutralization and by its inefficient spread within solid tumor masses; this spread is typically from cell to adjacent cell. IMV spread to distant tumor masses, either through the bloodstream or lymphatics, is also inefficient.

Therefore, the rare EEV form of vaccinia virus has naturally acquired features that make it superior to the vaccinia virus form used in patients to date (IMV); EEV is optimized for rapid and efficient spread through solid tumors locally and to regional or distant tumor sites. Since EEV is relatively resistant to complement effects, when it is grown in a cell type from the same species, this virus form will have enhanced stability and retain activity longer in the blood following intravascular administration than standard preparations of vaccinia virus (which contain exclusively IMV) (Smith et al., 1998). Since EEV is resistant to antibody-mediated neutralization, this virus form will retain activity longer in the blood following intravascular administration than standard preparations of vaccinia virus (which contain almost exclusively IMV) (Vanderplasschen et al., 1998). This feature will be particularly important for repeat administration once neutralizing antibody levels have increased; all approved anti-cancer therapies require repeat administration. Therefore, the EEV form of vaccinia, and other poxviruses, will result in superior delivery of therapeutic viruses and their genetic payload to tumors through the bloodstream. This will lead to enhanced systemic efficacy compared with standard poxvirus preparations. Finally, the risk of transmission to individuals in the general public should be reduced significantly since EEV is extremely unstable outside of the body. Polypeptides involved in the modulation of the EEV form of a virus include, but are not limited to, A34R, B5R, and various other proteins that influence the production of the EEV form of the poxviruses. A mutation at codon 151 of A34R from a lysine to a aspartic acid (K151D mutation) renders the A34R protein less able to tether the EEV form to the cell membrane. B5R is an EEV-membrane bound polypeptide that may bind complement. The total deletion of A43R may lead to increased EEV release, but markedly reduced infectivity of the viruses, while the K151D mutation increases EEV release while maintaining infectivity of the released viruses. B5R has sequence homology to VCP (anti-complement), but complement inhibition has not yet been proven.

Briefly, one method for identifying a fortified EEV form is as follows. EEV are diluted in ice-cold MEM and mixed (1:1 volume) with active or heat-inactivated (56° C., 30 min, control) serum diluted in ice-cold MEM (final dilution of serum 1/10, 1/20, or 1/30). After incubation or 75 min at 7° C., samples are cooled on ice and mAb 5B4/2F2 is added to fresh EEV samples to neutralize any contaminates (IMV and ruptured EEV). Virions are then bound to RK13 cells for one hour on ice, complement and unbound virions are washed away, and the number of plaques are counted two days later. The higher the plaque number the greater the resistance to complement (Vanderplasschen et al., 1998, herein incorporated by reference). Exemplary methods describing the isolation of EEV forms of vaccinia virus can be found in Blasco et al., 1992 (incorporated herein by reference).

7. Other Polypeptides

Other viral immunomodulatory polypeptides may include polypeptides that bind other mediators of the immune response and/or modulate molecular pathways associated with the immune response. For example, chemokine binding polypeptides such as B29R (this protein is present, but may be inactive in the Copenhagen strain of vaccinia virus), C23L, vCKBP, A41L and polypeptides with similar activities or properties. Other vaccinia virus proteins such as the vaccinia virus growth factor (e.g., C11L), which is a viral EGF-like growth factor, may also be the target for alteration in some embodiments of the invention. Other polypeptides that may be classified as viral immunomodulatory factors include, but are not limited to B7R, N1L, or other polypeptides that whose activities or properties increase the virulence of a poxvirus.

8. Vaccinia Virus-Induced Cell Fusion

In certain embodiments of the invention an alteration, deletion, or mutation of A56R or K2L encoding nucleic genes may lead to cell-cell fusion or syncyia formation induced by VV infection. Vaccinia virus-induced cell fusion will typically increase antitumoral efficacy of VV due to intratumoral viral spread. Intratumoral viral spreading by cell fusion will typically allow the virus to avoid neutralizing antibodies and immune responses. Killing and infection of adjacent uninfected cells (i.e., a "bystander effect") may be more efficient in VV with mutations in one or both of these genes, which may result in improved local antitumoral effects.

D. Other Poxviruses

Vaccinia virus is a member of the family Poxviridae, the subfamily Chordopoxvirinae and the genus Orthopoxvirus. The genus Orthopoxvirus is relatively more homogeneous than other members of the Chordopoxvirinae subfamily and includes 11 distinct but closely related species, which includes vaccinia virus, variola virus (causative agent of smallpox), cowpox virus, buffalopox virus, monkeypox virus, mousepox virus and horsepox virus species as well as others (see Moss, 1996). Certain embodiments of the invention, as described herein, may be extended to other members of Orthopoxvirus genus as well as the Parapoxvirus, Avipoxvirus, Capripoxvirus, Leporipoxvirus, Suipoxvirus, Molluscipoxvirus, and Yatapoxvirus genus. A genus of poxvirus family is generally defined by serological means including neutralization and cross-reactivity in laboratory animals. Various members of the Orthopoxvirus genus, as well as other members of the Chordovirinae subfamily utilize immunomodulatory molecules, examples of which are provided herein, to counteract the immune responses of a host organism. Thus, the invention described herein is not limited to vaccinia virus, but may be applicable to a number of viruses.

E. Virus Propagation

Vaccinia virus may be propagated using the methods described by Earl and Moss in Ausubel et al., 1994, which is incorporated by reference herein.

II. Proteinaceous and Nucleic Acid Compositions

The present invention concerns poxviruses, including those constructed with one or more mutations compared to wild-type such that the virus has desirable properties for use against cancer cells, while being less toxic or non-toxic to non-cancer cells. Such poxviruses are described in U.S. Patent Application Publication Number 2006/0099224, which is incorporated herein by reference. The teachings described below provide various protocols, by way of example, of implementing methods and compositions of the invention, such as methods for generating mutated viruses through the use of recombinant DNA technology.

In certain embodiments, the present invention concerns generating poxviruses that lack one or more functional polypeptides or proteins and/or generating poxviruses that have the ability to release more of a particular form of the virus, such as an infectious EEV form. In other embodiments, the present invention concerns poxviruses and their use in combination with proteinaceous composition as part of a pharmaceutically acceptable formulation.

As used herein, a "protein" or "polypeptide" refers to a molecule comprising at least one amino acid residue. In some embodiments, a wild-type version of a protein or polypeptide are employed, however, in many embodiments of the invention, a viral protein or polypeptide is absent or altered so as to render the virus more useful for the treatment of a cancer cells or cancer in a patient. The terms described above may be used interchangeably herein. A "modified protein" or "modified polypeptide" refers to a protein or polypeptide whose chemical structure is altered with respect to the wild-type protein or polypeptide. In some embodiments, a modified protein or polypeptide has at least one modified activity or function (recognizing that proteins or polypeptides may have multiple activities or functions). The modified activity or function may be reduced, diminished, eliminated, enhanced, improved, or altered in some other way (such as specificity) with respect to that activity or function in a wild-type protein or polypeptide. It is specifically contemplated that a modified protein or polypeptide may be altered with respect to one activity or function yet retain wild-type activity or function in other respects. Alternatively, a modified protein may be completely nonfunctional or its cognate nucleic acid sequence may have been altered so that the polypeptide is no longer expressed at all, is truncated, or expresses a different amino acid sequence as a result of a frameshift.

In certain embodiments the size of a mutated protein or polypeptide may comprise, but is not limited to, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 210, 220, 230, 240, 250, 275, 300, 325, 350, 375, 400, 425, 450, 475, 500, 525, 550, 575, 600, 625, 650, 675, 700, 725, 750, 775, 800, 825, 850, 875, 900, 925, 950, 975, 1000, 1100, 1200, 1300, 1400, 1500, 1750, 2000, 2250, 2500 or greater amino molecule residues, and any range derivable therein. It is contemplated that polypeptides may be mutated by truncation, rendering them shorter than their corresponding wild-type form.

As used herein, an "amino molecule" refers to any amino acid, amino acid derivative or amino acid mimic as would be known to one of ordinary skill in the art. In certain embodiments, the residues of the proteinaceous molecule are sequential, without any non-amino molecule interrupting the sequence of amino molecule residues. In other embodiments, the sequence may comprise one or more non-amino molecule moieties. In particular embodiments, the sequence of residues of the proteinaceous molecule may be interrupted by one or more non-amino molecule moieties.

Accordingly, the term "proteinaceous composition" encompasses amino molecule sequences comprising at least one of the 20 common amino acids in naturally synthesized proteins, or at least one modified or unusual amino acid.

Proteinaceous compositions may be made by any technique known to those of skill in the art, including the expression of proteins, polypeptides or peptides through standard molecular biological techniques, the isolation of proteinaceous compounds from natural sources, or the chemical synthesis of proteinaceous materials. The nucleotide and protein, polypeptide and peptide sequences for various genes have been previously disclosed, and may be found at computerized databases known to those of ordinary skill in the art. One such database is the National Center for Biotechnology Information's Genbank and GenPept databases (www.ncbi.nlm.nih.gov/). The coding regions for these known genes may be amplified and/or expressed using the techniques disclosed herein or as would be know to those of ordinary skill in the art.

A. Functional Aspects

When the present application refers to the function or activity of viral proteins or polypeptides, it is meant to refer to the activity or function of that viral protein or polypeptide under physiological conditions, unless otherwise specified. For example, an interferon-modulating polypeptide refers to a polypeptide that affects at least one interferon and its activity, either directly or indirectly. The polypeptide may induce, enhance, raise, increase, diminish, weaken, reduce, inhibit, or mask the activity of an interferon, directly or indirectly. An example of directly affecting interferon involves, in some embodiments, an interferon-modulating polypeptide that specifically binds to the interferon. Determination of which molecules possess this activity may be achieved using assays familiar to those of skill in the art. For example, transfer of genes encoding products that modulate interferon, or variants thereof, into cells that are induced for interferon activity compared to cells with such transfer of genes may identify, by virtue of different levels of an interferon response, those molecules having a interferon-modulating function.

It is specifically contemplated that a modulator may be a molecule that affects the expression proteinaceous compositions involved in the targeted molecule's pathway, such as by binding an interferon-encoding transcript. Determination of which molecules are suitable modulators of interferon, IL-1β, TNF, or other molecules of therapeutic benefit may be achieved using assays familiar to those of skill in the art—some of which are disclosed herein—and may include, for example, the use of native and/or recombinant viral proteins.

B. Variants of Viral Polypeptides

Amino acid sequence variants of the polypeptides of the present invention can be substitutional, insertional or deletion variants. A mutation in a gene encoding a viral polypeptide may affect 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 210, 220, 230, 240, 250, 275, 300, 325, 350, 375, 400, 425, 450, 475, 500 or more non-contiguous or contiguous amino acids of the polypeptide, as compared to wild-type. Various polypeptides encoded by Vaccinia virus may be identified by reference to Rosel et al., 1986, Goebel et al., 1990 and GenBank Accession Number NC001559, each of which is incorporated herein by reference.

Deletion variants lack one or more residues of the native or wild-type protein. Individual residues can be deleted or all or part of a domain (such as a catalytic or binding domain) can be deleted. A stop codon may be introduced (by substitution or insertion) into an encoding nucleic acid sequence to generate a truncated protein. Insertional mutants typically involve the addition of material at a non-terminal point in the polypeptide. This may include the insertion of an immunoreactive epitope or simply one or more residues. Terminal additions, called fusion proteins, may also be generated.

Substitutional variants typically contain the exchange of one amino acid for another at one or more sites within the protein, and may be designed to modulate one or more properties of the polypeptide, with or without the loss of other functions or properties. Substitutions may be conservative, that is, one amino acid is replaced with one of similar shape and charge. Conservative substitutions are well known in the art and include, for example, the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine; methionine to leucine or isoleucine; phenylalanine to tyrosine, leucine or methionine; serine to threonine; threonine to serine; tryptophan to tyrosine; tyrosine to tryptophan or phenylalanine; and valine to isoleucine or leucine. Alternatively, substitutions may be non-conservative such that a function or activity of the polypeptide is affected. Non-conservative changes typically involve substituting a residue with one that is chemically dissimilar, such as a polar or charged amino acid for a nonpolar or uncharged amino acid, and vice versa.

The term "functionally equivalent codon" is used herein to refer to codons that encode the same amino acid (see Table 1, below).

TABLE 1

Codon Table

| Amino Acids | | | Codons |
|---|---|---|---|
| Alanine | Ala | A | GCA GCC GCG GCU |
| Cysteine | Cys | C | UGC UGU |
| Aspartic acid | Asp | D | GAC GAU |
| Glutamic acid | Glu | E | GAA GAG |
| Phenylalanine | Phe | F | UUC UUU |
| Glycine | Gly | G | GGA GGC GGG GGU |
| Histidine | His | H | CAC CAU |
| Isoleucine | Ile | I | AUA AUC AUU |
| Lysine | Lys | K | AAA AAG |
| Leucine | Leu | L | UUA UUG CUA CUC CUG CUU |
| Methionine | Met | M | AUG |
| Asparagine | Asn | N | AAC AAU |
| Proline | Pro | P | CCA CCC CCG CCU |
| Glutamine | Gln | Q | CAA CAG |
| Arginine | Arg | R | AGA AGG CGA CGC CGG CGU |
| Serine | Ser | S | AGC AGU UCA UCC UCG UCU |
| Threonine | Thr | T | ACA ACC ACG ACU |
| Valine | Val | V | GUA GUC GUG GUU |
| Tryptophan | Trp | W | UGG |
| Tyrosine | Tyr | Y | UAC UAU |

It also will be understood that amino acid and nucleic acid sequences may include additional residues, such as additional N- or C-terminal amino acids or 5' or 3' sequences, and yet still be essentially as set forth in one of the sequences disclosed herein, so long as the sequence meets the criteria set forth above, including the maintenance of biological protein activity where protein expression is concerned. The addition of terminal sequences particularly applies to nucleic acid sequences that may, for example, include various non-coding sequences flanking either of the 5' or 3' portions of the coding region or may include various internal sequences, i.e., introns, which are known to occur within genes.

The following is a discussion based upon changing of the amino acids of a protein to create an equivalent, or even an improved, second-generation molecule. For example, certain amino acids may be substituted for other amino acids in a protein structure without appreciable loss of interactive binding capacity with structures such as, for example, antigen-binding regions of antibodies or binding sites on substrate molecules. Since it is the interactive capacity and nature of a protein that defines that protein's biological functional activity, certain amino acid substitutions can be made in a protein sequence, and in its underlying DNA coding sequence, and nevertheless produce a protein with like properties. It is thus contemplated by the inventors that various changes may be made in the DNA sequences of genes without appreciable loss of their biological utility or activity, as discussed below. Table 1 shows the codons that encode particular amino acids.

In making such changes, the hydropathic index of amino acids may be considered. The importance of the hydropathic amino acid index in conferring interactive biologic function on a protein is generally understood in the art byte and Kyte and Doolittle, 1982). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

It also is understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein. As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine *−0.5); cysteine (−1.0); methionine (−1.3); valine (−1.5); leucine (−1.8); isoleucine (−1.8); tyrosine (−2.3); phenylalanine (−2.5); tryptophan (−3.4).

It is understood that an amino acid can be substituted for another having a similar hydrophilicity value and still produce a biologically equivalent and immunologically equivalent protein. In such changes, the substitution of amino acids whose hydrophilicity values are within ±2 is preferred, those that are within ±1 are particularly preferred, and those within +0.5 are even more particularly preferred.

As outlined above, amino acid substitutions generally are based on the relative similarity of the amino acid side-chain substituents, for example, their hydrophobicity, hydrophilicity, charge, size, and the like. Exemplary substitutions that take into consideration the various foregoing characteristics are well known to those of skill in the art and include: arginine and lysine; glutamate and aspartate; serine and threonine; glutamine and asparagine; and valine, leucine and isoleucine.

III. Nucleic Acid Molecules

A. Polynucleotides Encoding Native Proteins or Modified Proteins

The present invention concerns polynucleotides, isolatable from cells, that are capable of expressing all or part of a protein or polypeptide. In some embodiments of the invention, it concerns a viral genome that has been specifically mutated to generate a virus that lacks certain functional viral polypeptides. The polynucleotides may encode a peptide or polypeptide containing all or part of a viral amino acid sequence or they be engineered so they do not encode such a viral polypeptide or encode a viral polypeptide having at least one function or activity reduced, diminished, or absent. Recombinant proteins can be purified from expressing cells to yield active proteins. The genome, as well as the definition of the coding regions of Vaccinia Virus may be found in Rosel et al., 1986; Goebel et al., 1990; and/or GenBank Accession Number NC_001559, each of which is incorporated herein by reference.

As used herein, the term "DNA segment" refers to a DNA molecule that has been isolated free of total genomic DNA of a particular species. Therefore, a DNA segment encoding a polypeptide refers to a DNA segment that contains wild-type, polymorphic, or mutant polypeptide-coding sequences yet is isolated away from, or purified free from, total mammalian or human genomic DNA. Included within the term "DNA segment" are a polypeptide or polypeptides, DNA segments smaller than a polypeptide, and recombinant vectors, including, for example, plasmids, cosmids, phage, viruses, and the like.

As used in this application, the term "poxvirus polynucleotide" refers to a nucleic acid molecule encoding a poxvirus polypeptide that has been isolated free of total genomic nucleic acid. Similarly, a "vaccinia virus polynucleotide" refers to a nucleic acid molecule encoding a vaccinia virus polypeptide that has been isolated free of total genomic nucleic acid. A "poxvirus genome" or a "vaccinia virus genome" refers to a nucleic acid molecule that can be provided to a host cell to yield a viral particle, in the presence or absence of a helper virus. The genome may or may have not been recombinantly mutated as compared to wild-type virus.

The term "cDNA" is intended to refer to DNA prepared using messenger RNA (mRNA) as template. The advantage of using a cDNA, as opposed to genomic DNA or DNA polymerized from a genomic, non- or partially-processed RNA template, is that the cDNA primarily contains coding sequences of the corresponding protein. There may be times when the full or partial genomic sequence is preferred, such as where the non-coding regions are required for optimal expression or where non-coding regions such as introns are to be targeted in an antisense strategy.

It also is contemplated that a particular polypeptide from a given species may be represented by natural variants that have slightly different nucleic acid sequences but, nonetheless, encode the same protein (see Table 1 above).

Similarly, a polynucleotide comprising an isolated or purified wild-type or mutant polypeptide gene refers to a DNA segment including wild-type or mutant polypeptide coding sequences and, in certain aspects, regulatory sequences, isolated substantially away from other naturally occurring genes or protein encoding sequences. In this respect, the term "gene" is used for simplicity to refer to a functional protein, polypeptide, or peptide-encoding unit (including any sequences required for proper transcription, post-translational modification, or localization). As will be understood by those in the art, this functional term includes genomic sequences, cDNA sequences, and smaller engineered gene segments that express, or may be adapted to express, proteins, polypeptides, domains, peptides, fusion proteins, and mutants. A nucleic acid encoding all or part of a native or modified polypeptide may contain a contiguous nucleic acid sequence encoding all or a portion of such a polypeptide of the following lengths: 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 441, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000, 1010, 1020, 1030, 1040, 1050, 1060, 1070, 1080, 1090, 1095, 1100, 1500, 2000, 2500, 3000, 3500, 4000, 4500, 5000, 5500, 6000, 6500, 7000, 7500, 8000, 9000, 10000, or more nucleotides, nucleosides, or base pairs.

In particular embodiments, the invention concerns isolated DNA segments and recombinant vectors incorporating DNA sequences that encode a wild-type or mutant poxvirus polypeptide or peptide that includes within its amino acid sequence a contiguous amino acid sequence in accordance with, or essentially corresponding to a native polypeptide. Thus, an isolated DNA segment or vector containing a DNA segment may encode, for example, a INF modulator or TNF-modulating polypeptide that can inhibit or reduce INF activity. The term "recombinant" may be used in conjunction with a polypeptide or the name of a specific polypeptide, and this generally refers to a polypeptide produced from a nucleic acid molecule that has been manipulated in vitro or that is the replicated product of such a molecule.

In other embodiments, the invention concerns isolated DNA segments and recombinant vectors incorporating DNA sequences that encode a polypeptide or peptide that includes within its amino acid sequence a contiguous amino acid sequence in accordance with, or essentially corresponding to the polypeptide.

The nucleic acid segments used in the present invention, regardless of the length of the coding sequence itself, may be combined with other nucleic acid sequences, such as promoters, polyadenylation signals, additional restriction enzyme sites, multiple cloning sites, other coding segments, and the like, such that their overall length may vary considerably. It is therefore contemplated that a nucleic acid fragment of almost any length may be employed, with the total length preferably being limited by the ease of preparation and use in the intended recombinant DNA protocol.

It is contemplated that the nucleic acid constructs of the present invention may encode full-length polypeptide from any source or encode a truncated version of the polypeptide, for example a truncated vaccinia virus polypeptide, such that the transcript of the coding region represents the truncated version. The truncated transcript may then be translated into a truncated protein. Alternatively, a nucleic acid sequence may encode a fill-length polypeptide sequence with additional heterologous coding sequences, for example to allow for purification of the polypeptide, transport, secretion, post-translational modification, or for therapeutic benefits such as targeting or efficacy. As discussed above, a tag or other heterologous polypeptide may be added to the modified polypeptide-encoding sequence, wherein "heterologous" refers to a polypeptide that is not the same as the modified polypeptide.

In a non-limiting example, one or more nucleic acid constructs may be prepared that include a contiguous stretch of nucleotides identical to or complementary to the a particular gene, such as the B18R gene. A nucleic acid construct may be at least 20, 30, 40, 50, 60, 70, 80, 90, 100, 110, 120, 130, 140, 150, 160, 170, 180, 190, 200, 250, 300, 400, 500, 600, 700, 800, 900, 1,000, 2,000, 3,000, 4,000, 5,000, 6,000, 7,000, 8,000, 9,000, 10,000, 15,000, 20,000, 30,000, 50,000, 100,000, 250,000, 500,000, 750,000, to at least 1,000,000 nucleotides in length, as well as constructs of greater size, up to and including chromosomal sizes (including all intermediate lengths and intermediate ranges), given the advent of nucleic acids constructs such as a yeast artificial chromosome are known to those of ordinary skill in the art. It will be readily understood that "intermediate lengths" and "intermediate ranges," as used herein, means any length or range including or between the quoted values (i.e., all integers including and between such values).

The DNA segments used in the present invention encompass biologically functional equivalent modified polypeptides and peptides, for example, a modified gelonin toxin. Such sequences may arise as a consequence of codon redundancy and functional equivalency that are known to occur naturally within nucleic acid sequences and the proteins thus encoded. Alternatively, functionally equivalent proteins or peptides may be created via the application of recombinant DNA technology, in which changes in the protein structure may be engineered, based on considerations of the properties of the amino acids being exchanged. Changes designed by human may be introduced through the application of site-directed mutagenesis techniques, e.g., to introduce improvements to the antigenicity of the protein, to reduce toxicity effects of the protein in vivo to a subject given the protein, or to increase the efficacy of any treatment involving the protein.

In certain other embodiments, the invention concerns isolated DNA segments and recombinant vectors that include within their sequence a contiguous nucleic acid sequence from that shown in sequences identified herein (and/or incorporated by reference). Such sequences, however, may be mutated to yield a protein product whose activity is altered with respect to wild-type.

It also will be understood that this invention is not limited to the particular nucleic acid and amino acid sequences of these identified sequences. Recombinant vectors and isolated DNA segments may therefore variously include the poxvirus-coding regions themselves, coding regions bearing selected alterations or modifications in the basic coding region, or they may encode larger polypeptides that nevertheless include poxvirus-coding regions or may encode biologically functional equivalent proteins or peptides that have variant amino acids sequences.

The DNA segments of the present invention encompass biologically functional equivalent poxvirus proteins and peptides. Such sequences may arise as a consequence of codon redundancy and functional equivalency that are known to occur naturally within nucleic acid sequences and the proteins thus encoded. Alternatively, functionally equivalent proteins or peptides may be created via the application of recombinant DNA technology, in which changes in the protein structure may be engineered, based on considerations of the properties of the amino acids being exchanged. Changes designed by man may be introduced through the application of site-directed mutagenesis techniques, e.g., to introduce improvements to the antigenicity of the protein.

B. Mutagenesis of Poxvirus Polynucleotides

In various embodiments, the poxvirus polynucleotide may be altered or mutagenized. Alterations or mutations may include insertions, deletions, point mutations, inversions, and the like and may result in the modulation, activation and/or inactivation of certain pathways or molecular mechanisms, as well as altering the function, location, or expression of a gene product, in particular rendering a gene product non-functional. Where employed, mutagenesis of a polynucleotide encoding all or part of a Poxvirus may be accomplished by a variety of standard, mutagenic procedures (Sambrook et al., 1989). Mutation is the process whereby changes occur in the quantity or structure of an organism. Mutation can involve modification of the nucleotide sequence of a single gene, blocks of genes or whole chromosome. Changes in single genes may be the consequence of point mutations which involve the removal, addition or substitution of a single nucleotide base within a DNA sequence, or they may be the consequence of changes involving the insertion or deletion of large numbers of nucleotides.

Mutations may be induced following exposure to chemical or physical mutagens. Such mutation-inducing agents include ionizing radiation, ultraviolet light and a diverse array of chemical such as alkylating agents and polycyclic aromatic hydrocarbons all of which are capable of interacting either directly or indirectly (generally following some metabolic biotransformations) with nucleic acids. The DNA damage induced by such agents may lead to modifications of base sequence when the affected DNA is replicated or repaired and thus to a mutation. Mutation also can be site-directed through the use of particular targeting methods.

C. Vectors

To generate mutations in the poxvirus genome, native and modified polypeptides may be encoded by a nucleic acid molecule comprised in a vector. The term "vector" is used to refer to a carrier nucleic acid molecule into which an exogenous nucleic acid sequence can be inserted for introduction into a cell where it can be replicated. A nucleic acid sequence can be "exogenous," which means that it is foreign to the cell into which the vector is being introduced or that the sequence is homologous to a sequence in the cell but in a position within the host cell nucleic acid in which the sequence is ordinarily not found. Vectors include plasmids, cosmids, viruses (bacteriophage, animal viruses, and plant viruses), and artificial chromosomes (e.g., YACs). One of skill in the art would be well equipped to construct a vector through standard recombinant techniques, which are described in Sambrook et al., (1989) and Ausubel et al., 1994, both incorporated herein by reference. In addition to encoding a modified polypeptide such as modified gelonin, a vector may encode non-modified polypeptide sequences such as a tag or targeting molecule. Useful vectors encoding such fusion proteins include pIN vectors (Inouye et al., 1985), vectors encoding a stretch of histidines, and pGEX vectors, for use in generating glutathione S-transferase (GST) soluble fusion proteins for later purification and separation or cleavage. A targeting molecule is one that directs the modified polypeptide to a particular organ, tissue, cell, or other location in a subject's body.

The term "expression vector" refers to a vector containing a nucleic acid sequence coding for at least part of a gene product capable of being transcribed. In some cases, RNA molecules are then translated into a protein, polypeptide, or peptide. In other cases, these sequences are not translated, for example, in the production of antisense molecules or ribozymes. Expression vectors can contain a variety of "control sequences," which refer to nucleic acid sequences necessary for the transcription and possibly translation of an operably linked coding sequence in a particular host organism. In addition to control sequences that govern transcription and translation, vectors and expression vectors may contain nucleic acid sequences that serve other functions as well and are described infra.

1. Promoters and Enhancers

A "promoter" is a control sequence that is a region of a nucleic acid sequence at which initiation and rate of transcription are controlled. It may contain genetic elements at which regulatory proteins and molecules may bind such as RNA polymerase and other transcription factors. The phrases "operatively positioned," "operatively linked," "under control," and "under transcriptional control" mean that a promoter is in a correct functional location and/or orientation in relation to a nucleic acid sequence to control transcriptional initiation and/or expression of that sequence. A promoter may or may not be used in conjunction with an "enhancer," which refers to a cis-acting regulatory sequence involved in the transcriptional activation of a nucleic acid sequence.

A promoter may be one naturally associated with a gene or sequence, as may be obtained by isolating the 5' non-coding sequences located upstream of the coding segment and/or exon. Such a promoter can be referred to as "endogenous." Similarly, an enhancer may be one naturally associated with a nucleic acid sequence, located either downstream or upstream of that sequence. Alternatively, certain advantages will be gained by positioning the coding nucleic acid segment under the control of a recombinant or heterologous promoter, which refers to a promoter that is not normally associated with a nucleic acid sequence in its natural environment. A recombinant or heterologous enhancer refers also to an enhancer not normally associated with a nucleic acid sequence in its natural environment. Such promoters or enhancers may include promoters or enhancers of other genes, and promoters or enhancers isolated from any other prokaryotic, viral, or eukaryotic cell, and promoters or enhancers not "naturally occurring," i.e., containing different elements of different transcriptional regulatory regions, and/or mutations that alter expression. In addition to producing nucleic acid sequences of promoters and enhancers synthetically, sequences may be produced using recombinant cloning and/or nucleic acid amplification technology, including PCR™, in connection with the compositions disclosed herein (see U.S. Pat. Nos. 4,683,202, 5,928,906, each incorporated herein by reference). Furthermore, it is contemplated the control sequences that direct transcription and/or expression of sequences within non-nuclear organelles such as mitochondria, chloroplasts, and the like, can be employed as well.

Naturally, it may be important to employ a promoter and/or enhancer that effectively directs the expression of the DNA segment in the cell type, organelle, and organism chosen for expression. Those of skill in the art of molecular biology generally know the use of promoters, enhancers, and cell type combinations for protein expression, for example, see Sambrook et al. (1989), incorporated herein by reference. The promoters employed may be constitutive, tissue-specific, inducible, and/or useful under the appropriate conditions to direct high level expression of the introduced DNA segment, such as is advantageous in the large-scale production of recombinant proteins and/or peptides. The promoter may be heterologous or endogenous.

The identity of tissue-specific promoters or elements, as well as assays to characterize their activity, is well known to those of skill in the art. Examples of such regions include the human LIMK2 gene (Nomoto et al. 1999), the somatostatin receptor 2 gene (Kraus et al., 1998), murine epididymal retinoic acid-binding gene (Lareyre et al., 1999), human CD4 (Zhao-Emonet et al., 1998), mouse α2 (XI) collagen (Tsumaki, et al., 1998), D1A dopamine receptor gene (Lee, et al., 1997), insulin-like growth factor II (Wu et al., 1997), human platelet endothelial cell adhesion molecule-1 (Almendro et al., 1996), and the SM22α promoter.

2. Initiation Signals and Internal Ribosome Binding Sites

A specific initiation signal also may be required for efficient translation of coding sequences. These signals include the ATG initiation codon or adjacent sequences. Exogenous translational control signals, including the ATG initiation codon, may need to be provided. One of ordinary skill in the art would readily be capable of determining this and providing the necessary signals. It is well known that the initiation codon must be "in-frame" with the reading frame of the desired coding sequence to ensure translation of the entire insert. The exogenous translational control signals and initiation codons can be either natural or synthetic. The efficiency of expression may be enhanced by the inclusion of appropriate transcription enhancer elements.

In certain embodiments of the invention, the use of internal ribosome entry sites (IRES) elements are used to create multigene, or polycistronic, messages. IRES elements are able to bypass the ribosome scanning model of 5'-methylated Cap dependent translation and begin translation at internal sites (Pelletier and Sonenberg, 1988). IRES elements from two members of the picornavirus family (polio and encephalomyocarditis) have been described (Pelletier and Sonenberg, 1988), as well an IRES from a mammalian message (Macejak and Sarnow, 1991). IRES elements can be linked to heterologous open reading flames. Multiple open reading frames can be transcribed together, each separated by an IRES, creating polycistronic messages. By virtue of the IRES element, each open reading frame is accessible to ribosomes for efficient translation. Multiple genes can be efficiently expressed using a single promoter/enhancer to transcribe a single message (see U.S. Pat. Nos. 5,925,565 and 5,935,819, herein incorporated by reference).

3. Multiple Cloning Sites

Vectors can include a multiple cloning site (NCS), which is a nucleic acid region that contains multiple restriction enzyme sites, any of which can be used in conjunction with standard recombinant technology to digest the vector. (See Carbonelli et al., 1999, Levenson et al., 1998, and Cocea, 1997, incorporated herein by reference.) "Restriction enzyme digestion" refers to catalytic cleavage of a nucleic acid molecule with an enzyme that functions only at specific locations in a nucleic acid molecule. Many of these restriction enzymes are commercially available. Use of such enzymes is widely understood by those of skill in the art. Frequently, a vector is linearized or fragmented using a restriction enzyme that cuts within the MCS to enable exogenous sequences to be ligated to the vector. "Ligation" refers to the process of forming phosphodiester bonds between two nucleic acid fragments, which may or may not be contiguous with each other. Techniques involving restriction enzymes and ligation reactions are well known to those of skill in the art of recombinant technology.

4. Splicing Sites

Most transcribed eukaryotic RNA molecules will undergo RNA splicing to remove introns from the primary transcripts. Vectors containing genomic eukaryotic sequences may require donor and/or acceptor splicing sites to ensure proper processing of the transcript for protein expression. (See Chandler et al., 1997, incorporated herein by reference.)

5. Termination Signals

The vectors or constructs of the present invention will generally comprise at least one termination signal. A "termination signal" or "terminator" is comprised of the DNA sequences involved in specific termination of an RNA transcript by an RNA polymerase. Thus, in certain embodiments a termination signal that ends the production of an RNA transcript is contemplated. A terminator may be necessary in vivo to achieve desirable message levels.

In eukaryotic systems, the terminator region may also comprise specific DNA sequences that permit site-specific cleavage of the new transcript so as to expose a polyadenylation site. This signals a specialized endogenous polymerase to add a stretch of about 200 A residues (polyA) to the 3' end of the transcript. RNA molecules modified with this polyA tail appear to more stable and are translated more efficiently. Thus, in other embodiments involving eukaryotes, it is preferred that that terminator comprises a signal for the cleavage of the RNA, and it is more preferred that the terminator signal promotes polyadenylation of the message. The terminator and/or polyadenylation site elements can serve to enhance message levels and/or to minimize read through from the cassette into other sequences.

Terminators contemplated for use in the invention include any known terminator of transcription described herein or known to one of ordinary skill in the art, including but not limited to, for example, the termination sequences of genes, such as for example the bovine growth hormone terminator or viral termination sequences, such as for example the SV40 terminator. In certain embodiments, the termination signal may be a lack of transcribable or translatable sequence, such as due to a sequence truncation.

6. Polyadenylation Signals

In expression, particularly eukaryotic expression, one will typically include a polyadenylation signal to effect proper polyadenylation of the transcript. The nature of the polyadenylation signal is not believed to be crucial to the successful practice of the invention, and/or any such sequence may be employed. Preferred embodiments include the SV40 polyadenylation signal and/or the bovine growth hormone polyadenylation signal, convenient and/or known to function well in various target cells. Polyadenylation may increase the stability of the transcript or may facilitate cytoplasmic transport.

7. Origins of Replication

In order to propagate a vector in a host cell, it may contain one or more origins of replication sites (often termed "ori"), which is a specific nucleic acid sequence at which replication is initiated. Alternatively an autonomously replicating sequence (ARS) can be employed if the host cell is yeast.

8. Selectable and Screenable Markers

In certain embodiments of the invention, cells containing a nucleic acid construct of the present invention may be identified in vitro or in vivo by including a marker in the expression vector. Such markers would confer an identifiable change to the cell permitting easy identification of cells containing the expression vector. Generally, a selectable marker is one that confers a property that allows for selection. A positive selectable marker is one in which the presence of the marker allows for its selection, while a negative selectable marker is one in which its presence prevents its selection. An example of a positive selectable marker is a drug resistance marker.

Usually the inclusion of a drug selection marker aids in the cloning and identification of transformants, for example, genes that confer resistance to neomycin, puromycin, hygromycin, DHFR, GPT, zeocin and histidinol are useful selectable markers. In addition to markers conferring a phenotype that allows for the discrimination of transformants based on the implementation of conditions, other types of markers including screenable markers such as GFP, whose basis is colorimetric analysis, are also contemplated. Alternatively, screenable enzymes such as herpes simplex virus thymidine kinase (tk) or chloramphenicol acetyltransferase (CAT) may be utilized. One of skill in the art would also know how to employ immunologic markers, possibly in conjunction with FACS analysis. The marker used is not believed to be important, so long as it is capable of being expressed simultaneously with the nucleic acid encoding a gene product. Further examples of selectable and screenable markers are well known to one of skill in the art.

D. Host Cells

As used herein, the terms "cell," "cell line," and "cell culture" may be used interchangeably. All of these terms also include their progeny, which is any and all subsequent generations. It is understood that all progeny may not be identical due to deliberate or inadvertent mutations. In the context of expressing a heterologous nucleic acid sequence, "host cell" refers to a prokaryotic or eukaryotic cell, and it includes any transformable organisms that is capable of replicating a vector and/or expressing a heterologous gene encoded by a vector. A host cell can, and has been, used as a recipient for vectors or viruses (which does not qualify as a vector if it expresses no exogenous polypeptides). A host cell may be "transfected" or "transformed," which refers to a process by which exogenous nucleic acid, such as a modified protein-encoding sequence, is transferred or introduced into the host cell. A transformed cell includes the primary subject cell and its progeny.

Host cells may be derived from prokaryotes or eukaryotes, including yeast cells, insect cells, and mammalian cells, depending upon whether the desired result is replication of the vector or expression of part or all of the vector-encoded nucleic acid sequences. Numerous cell lines and cultures are available for use as a host cell, and they can be obtained through the American Type Culture Collection (ATCC), which is an organization that serves as an archive for living cultures and genetic materials (www.atcc.org). An appropriate host can be determined by one of skill in the art based on the vector backbone and the desired result. A plasmid or cosmid, for example, can be introduced into a prokaryote host cell for replication of many vectors. Bacterial cells used as host cells for vector replication and/or expression include DH5α, JM109, and KC8, as well as a number of commercially available bacterial hosts such as SURE® Competent Cells and SOLOPACK™ Gold Cells (STRATAGENE®, La Jolla, Calif.). Alternatively, bacterial cells such as *E. coli* LE392 could be used as host cells for phage viruses. Appropriate yeast cells include *Saccharomyces cerevisiae, Saccharomyces pombe*, and *Pichia pastoris*.

Examples of eukaryotic host cells for replication and/or expression of a vector include HeLa, NIH3T3, Jurkat, 293, Cos, CHO, Saos, and PC12. Many host cells from various cell types and organisms are available and would be known to one of skill in the art. Similarly, a viral vector may be used in conjunction with either a eukaryotic or prokaryotic host cell, particularly one that is permissive for replication or expression of the vector.

Some vectors may employ control sequences that allow it to be replicated and/or expressed in both prokaryotic and eukaryotic cells. One of skill in the art would further understand the conditions under which to incubate all of the above described host cells to maintain them and to permit replication of a vector. Also understood and known are techniques and conditions that would allow large-scale production of vectors, as well as production of the nucleic acids encoded by vectors and their cognate polypeptides, proteins, or peptides.

E. Methods of Gene Transfer

Suitable methods for nucleic acid delivery to effect expression of compositions of the present invention are believed to include virtually any method by which a nucleic acid (e.g., DNA, including viral and non-viral vectors) can be introduced into an organelle, a cell, a tissue or an organism, as described herein or as would be known to one of ordinary skill in the art. Such methods include, but are not limited to, direct delivery of DNA such as by injection (U.S. Pat. Nos. 5,994,624, 5,981,274, 5,945,100, 5,780,448, 5,736,524, 5,702,932, 5,656,610, 5,589,466 and 5,580,859, each incorporated herein by reference), including microinjection (Harland and Weintraub, 1985; U.S. Pat. No. 5,789, 215, incorporated herein by reference); by electroporation (U.S. Pat. No. 5,384,253, incorporated herein by reference); by calcium phosphate precipitation (Graham and Van Der Eb, 1973; Chen and Okayama, 1987; Rippe et al., 1990); by using DEAE-dextran followed by polyethylene glycol (Gopal, 1985); by direct sonic loading (Fechheimer et al., 1987); by liposome mediated transfection (Nicolau and Sene, 1982; Fraley et al., 1979; Nicolau et al., 1987; Wong et al., 1980; Kaneda et al., 1989; Kato et al., 1991); by microprojectile bombardment (PCT Application Nos. WO 94/09699 and 95/06128; U.S. Pat. Nos. 5,610,042; 5,322,783, 5,563,055, 5,550,318, 5,538,877 and 5,538,880, and each incorporated herein by reference); by agitation with silicon carbide fibers (Kaeppler et al., 1990; U.S. Pat. Nos. 5,302,523 and 5,464, 765, each incorporated herein by reference); by *Agrobacterium*-mediated transformation (U.S. Pat. Nos. 5,591,616 and 5,563,055, each incorporated herein by reference); or by PEG-mediated transformation of protoplasts (Omirulleh et al., 1993; U.S. Pat. Nos. 4,684,611 and 4,952,500, each incorporated herein by reference); by desiccation/inhibition-mediated DNA uptake (Potrykus et al., 1985). Through the application of techniques such as these, organelle(s), cell(s), tissue(s) or organism(s) may be stably or transiently transformed.

F. Lipid Components and Moieties

In certain embodiments, the present invention concerns compositions comprising one or more lipids associated with a nucleic acid, an amino acid molecule, such as a peptide, or another small molecule compound. In any of the embodiments discussed herein, the molecule may be either a poxvirus polypeptide or a poxvirus polypeptide modulator, for example a nucleic acid encoding all or part of either a poxvirus polypeptide, or alternatively, an amino acid molecule encoding all or part of poxvirus polypeptide modulator. A lipid is a substance that is characteristically insoluble in water and extractable with an organic solvent. Compounds than those specifically described herein are understood by one of skill in the art as lipids, and are encompassed by the compositions and methods of the present invention. A lipid component and a non-lipid may be attached to one another, either covalently or non-covalently.

A lipid may be naturally-occurring or synthetic (i.e., designed or produced by man). However, a lipid is usually a biological substance. Biological lipids are well known in the art, and include for example, neutral fats, phospholipids, phosphoglycerides, steroids, terpenes, lysolipids, glycosphingolipids, glucolipids, sulphatides, lipids with ether and ester-linked fatty acids and polymerizable lipids, and combinations thereof A nucleic acid molecule or amino acid molecule, such as a peptide, associated with a lipid may be dispersed in a solution containing a lipid, dissolved with a lipid, emulsified with a lipid, mixed with a lipid, combined with a lipid, covalently bonded to a lipid, contained as a suspension in a lipid or otherwise associated with a lipid. A lipid or lipid/poxvirus-associated composition of the present invention is not limited to any particular structure. For example, they may also simply be interspersed in a solution, possibly forming aggregates which are not uniform in either size or shape. In another example, they may be present in a bilayer structure, as micelles, or with a "collapsed" structure. In another non-limiting example, a lipofectamine (Gibco BRL)-poxvirus or Superfect (Qiagen)-poxvirus complex is also contemplated.

In certain embodiments, a lipid composition may comprise about 1%, about 2%, about 3%, about 4% about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, about 100%, or any range derivable therein, of a particular lipid, lipid type or non-lipid component such as a drug, protein, sugar, nucleic acids or other material disclosed herein or as would be known to one of skill in the art. In a non-limiting example, a lipid composition may comprise about 10% to about 20% neutral lipids, and about 33% to about 34% of a cerebroside, and about 1% cholesterol. In another non-limiting example, a liposome may comprise about 4% to about 12% terpenes, wherein about 1% of the micelle is specifically lycopene, leaving about 3% to about 11% of the liposome as comprising other terpenes; and about 10% to about 35% phosphatidyl choline, and about 1% of a drug. Thus, it is contemplated that lipid compositions of the present invention may comprise any of the lipids, lipid types or other components in any combination or percentage range.

G. GM-CSF

In a particular aspect of the invention, the vaccinia viruses will carry a gene encoding for GM-CSF. GM-CSF is granulocyte-macrophage colony-stimulating factor, a substance that helps make more white blood cells, especially granulocytes, macrophages, and cells that become platelets. It is a cytokine that belongs to the family of drugs called hematopoietic (blood-forming) agents, and is also known as sargramostim. GM-CSF was first cloned and sequence in 1985 by Cantrell et al. (1985). Human GM-CSF is a 144-amino acid glycoprotein encoded by a single open-reading frame with a predicted molecular mass of 16,293 daltons. It exhibits a 69% nucleotide homology and 54% amino acid homology to mouse GM-CSF and exists as a single-copy gene.

GM-CSF is produced by a number of different cell types (including activated T cells, B cells, macrophages, mast cells, endothelial cells and fibroblasts) in response to cytokine or immune and inflammatory stimuli. Besides granulocyte-macrophage progenitors, GM-CSF is also a growth factor for erythroid, megakaryocyte and eosinophil progenitors. On mature hematopoietic cells, GM-CSF is a survival factor for and activates the effector functions of granulocytes, monocytes/macrophages and eosinophils. GM-CSF has also been reported to have a functional role on non-hematopoietic cells. It can induce human endothelial cells to migrate and proliferate.

GM-CSF is species specific and human GM-CSF has no biological effects on mouse cells. GM-CSF exerts its biological effects through binding to specific cell surface receptors. The high affinity receptors required for human GM-CSF signal transduction have been shown to be heterodimers consisting of a GM-CSF-specific a chain and a common β chain that is shared by the high-affinity receptors for IL-3 and IL-5.

Although GM-CSF can stimulate the proliferation of a number of tumor cell lines, including osteogenic sarcoma, carcinoma and adenocarcinoma cell lines, clinical trials of GM-CSF (alone or with other immunotherapies) are in progress for people with melanoma, leukemia, lymphoma, neuroblastoma, Kaposi sarcoma, mesothelioma, lung cancer, breast cancer, prostate cancer, colorectal cancer, brain tumors, kidney cancer and cervical cancer. Common side effects of GM-CSF include flu-like symptoms (fever, headaches, muscle aches), rashes, facial flushing, and bone pain.

H. Other Heterologous Genes

In some embodiments, the vaccinia virus used in methods of the invention contains a nucleic acid sequence that expresses a heterologous sequence that does not encode GM-CSF but encodes another heterologous sequence. In certain embodiments, the heterologous sequence encodes another cytokine. Alternatively or additionally, the vaccinia virus may contain a nucleic acid that encodes for IL-12, thymidine deaminase, TNF, and the like. In addition, any gene product discussed herein may be encoded by a nucleic acid contained within a vaccinia virus and used in methods of the invention.

IV. Pharmaceutical Formulations, Delivery and Treatment Regimens

In an embodiment of the present invention, a method of treatment for a hyperproliferative disease, such as cancer, by the delivery of an altered poxvirus, such as vaccinia virus, is contemplated. Examples of cancer contemplated for treatment include liver cancer, lung cancer, head and neck cancer, breast cancer, pancreatic cancer, prostate cancer, renal cancer, bone cancer, testicular cancer, cervical cancer, gastrointestinal cancer, lymphomas, pre-neoplastic lesions in the lung, colon cancer, melanoma, bladder cancer and any other cancers or tumors that may be treated.

An effective amount of the pharmaceutical composition is defined herein as that amount sufficient to induce oncolysis, the disruption or lysis of a cancer cell, as well as slowing, inhibition or reduction in the growth or size of a tumor and includes the eradication of the tumor in certain instances. An effective amount can also encompass an amount that results in systemic dissemination of the therapeutic virus to tumors indirectly, e.g., infection of non-injected tumors.

Preferably, patients will have adequate bone marrow function (defined as a peripheral absolute granulocyte count of >2,000/mm$^3$ and a platelet count of 100,000/mm$^3$), adequate liver function (bilirubin <1.5 mg/dl) and adequate renal function (creatinine <1.5 mg/dl).

Cancer cells that may be treated by methods and compositions of the invention include cells from the bladder, blood, bone, bone marrow, brain, breast, colon, esophagus, gastrointestine, gum, head, kidney, liver, lung, nasopharynx, neck, ovary, prostate, skin, stomach, testis, tongue, or uterus. In addition, the cancer may specifically be of the following histological type, though it is not limited to these: neoplasm, malignant; carcinoma; carcinoma, undifferentiated; giant and spindle cell carcinoma; small cell carcinoma; papillary carcinoma; squamous cell carcinoma; lymphoepithelial carcinoma; basal cell carcinoma; pilomatrix carcinoma; transitional cell carcinoma; papillary transitional cell carcinoma; adenocarcinoma; gastrinoma, malignant; cholangiocarcinoma; hepatocellular carcinoma; combined hepatocellular carcinoma and cholangiocarcinoma; trabecular adenocarcinoma; adenoid cystic carcinoma; adenocarcinoma in adenomatous polyp; adenocarcinoma, familial polyposis coli; solid carcinoma; carcinoid tumor, malignant; branchiolo-alveolar adenocarcinoma; papillary adenocarcinoma; chromophobe carcinoma; acidophil carcinoma; oxyphilic adenocarcinoma; basophil carcinoma; clear cell adenocarcinoma; granular cell carcinoma; follicular adenocarcinoma; papillary and follicular adenocarcinoma; nonencapsulating sclerosing carcinoma; adrenal cortical carcinoma; endometroid carcinoma; skin appendage carcinoma; apocrine adenocarcinoma; sebaceous adenocarcinoma; ceruminous adenocarcinoma; mucoepidermoid carcinoma; cystadenocarcinoma; papillary cystadenocarcinoma; papillary serous cystadenocarcinoma; mucinous cystadenocarcinoma; mucinous adenocarcinoma; signet ring cell carcinoma; infiltrating duct carcinoma; medullary carcinoma; lobular carcinoma; inflammatory carcinoma; paget's disease, mammary; acinar cell carcinoma; adenosquamous carcinoma; adenocarcinoma w/squamous metaplasia; thymoma, malignant; ovarian stromal tumor, malignant; thecoma, malignant; granulosa cell tumor, malignant; androblastoma, malignant; sertoli cell carcinoma; leydig cell tumor, malignant; lipid cell tumor, malignant; paraganglioma, malignant; extramammary paraganglioma, malignant; pheochromocytoma; glomangiosarcoma; malignant melanoma; amelanotic melanoma; superficial spreading melanoma; malig melanoma in giant pigmented nevus; epithelioid cell melanoma; blue nevus, malignant; sarcoma; fibrosarcoma; fibrous histiocytoma, malignant; myxosarcoma; liposarcoma; leiomyosarcoma; rhabdomyosarcoma; embryonal rhabdomyosarcoma; alveolar rhabdomyosarcoma; stromal sarcoma; mixed tumor, malignant; mullerian mixed tumor; nephroblastoma; hepatoblastoma; carcinosarcoma; mesenchymoma, malignant; brenner tumor, malignant; phyllodes tumor, malignant; synovial sarcoma; mesothelioma, malignant; dysgerminoma; embryonal carcinoma; teratoma, malignant; struma ovarii, malignant; choriocarcinoma; mesonephroma, malignant; hemangiosarcoma; hemangioendothelioma, malignant; Kaposi's sarcoma; hemangiopericytoma, malignant; lymphangiosarcoma; osteosarcoma; juxtacortical osteosarcoma; chondrosarcoma; chondroblastoma, malignant; mesenchymal chondrosarcoma; giant cell tumor of bone; Ewing's sarcoma; odontogenic tumor, malignant; ameloblastic odontosarcoma; ameloblastoma, malignant; ameloblastic fibrosarcoma; pinealoma, malignant; chordoma; glioma, malignant; ependymoma; astrocytoma; protoplasmic astrocytoma; fibrillary astrocytoma; astroblastoma; glioblastoma; oligodendroglioma; oligodendroblastoma; primitive neuroectodermal; cerebellar sarcoma; ganglioneuroblastoma; neuroblastoma; retinoblastoma; olfactory neurogenic tumor; meningioma, malignant; neurofibrosarcoma; neurilemmoma, malignant; granular cell tumor, malignant; malignant lymphoma; hodgkin's disease; hodgkin's; paragranuloma; malignant lymphoma, small lymphocytic; malignant lymphoma, large cell, diffuse; malignant lymphoma, follicular; mycosis fungoides; other specified non-hodgkin's lymphomas; malignant histiocytosis; multiple myeloma; mast cell sarcoma; immunoproliferative small intestinal disease; leukemia; lymphoid leukemia; plasma cell leukemia; erythroleukemia; lymphosarcoma cell leukemia; myeloid leukemia; basophilic leukemia; eosinophilic leukemia; monocytic leukemia; mast cell leukemia; megakaryoblastic leukemia; myeloid sarcoma; and hairy cell leukemia.

The present invention contemplates methods for inhibiting or preventing local invasiveness and/or metastasis of any type of primary cancer. For example, the primary cancer may be melanoma, non-small cell lung, small-cell lung, lung, hepatocarcinoma, retinoblastoma, astrocytoma, glioblastoma, gum, tongue, leukemia, neuroblastoma, head, neck, breast, pancreatic, prostate, renal, bone, testicular, ovarian, mesothelioma, cervical, gastrointestinal, lymphoma, brain, colon, or bladder. In certain embodiments of the present invention, the primary cancer is lung cancer. For example, the lung cancer may be non-small cell lung carcinoma.

Moreover, the present invention can be used to prevent cancer or to treat precancers or premalignant cells, including metaplasias, dysplasias, and hyperplasias. It may also be used to inhibit undesirable but benign cells, such as squamous metaplasia, dysplasia, benign prostate hyperplasia cells, hyperplastic lesions, and the like. The progression to cancer or to a more severe form of cancer may be halted, disrupted, or delayed by methods of the invention involving GM-CSF polypeptides or other polypeptide(s) encoded by a vaccinia virus, as discussed herein.

A. Administration

To induce oncolysis, kill cells, inhibit growth, inhibit metastases, decrease tumor size and otherwise reverse or reduce the malignant phenotype of tumor cells, using the methods and compositions of the present invention, one would contact a tumor with the poxvirus expressing GM-CSF. The routes of administration will vary, naturally, with the location and nature of the lesion, and include, e.g., intradermal, transdermal, parenteral, intravenous, intramuscular, intranasal, subcutaneous, regional (e.g., in the proximity of a tumor, particularly with the vasculature or adjacent vasculature of a tumor), percutaneous, intratracheal, intraperitoneal, intraarterial, intravesical, intratumoral, inhalation, perfusion, lavage, and oral administration and formulation.

The term "intravascular" is understood to refer to delivery into the vasculature of a patient, meaning into, within, or in a vessel or vessels of the patient. In certain embodiments, the administration is into a vessel considered to be a vein (intravenous), while in others administration is into a vessel considered to be an artery. Veins include, but are not limited to, the internal jugular vein, a peripheral vein, a coronary vein, a hepatic vein, the portal vein, great saphenous vein, the pulmonary vein, superior vena cava, inferior vena cava, a gastric vein, a splenic vein, inferior mesenteric vein, superior mesenteric vein, cephalic vein, and/or femoral vein. Arteries include, but are not limited to, coronary artery, pulmonary artery, brachial artery, internal carotid artery, aortic arch, femoral artery, peripheral artery, and/or ciliary artery. It is contemplated that delivery may be through or to an arteriole or capillary.

Intratumoral injection, or injection directly into the tumor vasculature is specifically contemplated for discrete, solid, accessible tumors. Local, regional or systemic administration also may be appropriate. For tumors of >4 cm, the volume to be administered will be about 4-10 ml (preferably 10 ml), while for tumors of <4 cm, a volume of about 1-3 ml will be used (preferably 3 ml). Multiple injections delivered as single dose comprise about 0.1 to about 0.5 ml volumes. The viral particles may advantageously be contacted by administering multiple injections to the tumor, spaced at approximately 1 cm intervals. In the case of surgical intervention, the present invention may be used preoperatively, to render an inoperable tumor subject to resection. Continuous administration also may be applied where appropriate, for example, by implanting a catheter into a tumor or into tumor vasculature. Such continuous perfusion may take place for a period from about 1-2 hours, to about 2-6 hours, to about 6-12 hours, or about 12-24 hours following the initiation of treatment. Generally, the dose of the therapeutic composition via continuous perfusion will be equivalent to that given by a single or multiple injections, adjusted over a period of time during which the perfusion occurs. It is further contemplated that limb perfusion may be used to administer therapeutic compositions of the present invention, particularly in the treatment of melanomas and sarcomas.

Treatment regimens may vary as well, and often depend on tumor type, tumor location, disease progression, and health and age of the patient. Obviously, certain types of tumor will require more aggressive treatment, while at the same time, certain patients cannot tolerate more taxing protocols. The clinician will be best suited to make such decisions based on the known efficacy and toxicity (if any) of the therapeutic formulations.

In certain embodiments, the tumor being treated may not, at least initially, be resectable. Treatments with therapeutic viral constructs may increase the resectability of the tumor due to shrinkage at the margins or by elimination of certain particularly invasive portions. Following treatments, resection may be possible. Additional treatments subsequent to resection will serve to eliminate microscopic residual disease at the tumor site.

The treatments may include various "unit doses." Unit dose is defined as containing a predetermined-quantity of the therapeutic composition. The quantity to be administered, and the particular route and formulation, are within the skill of those in the clinical arts. A unit dose need not be administered as a single injection but may comprise continuous infusion over a set period of time. Unit dose of the present invention may conveniently be described in terms of plaque forming units (pfu) for a viral construct. Unit doses range from $10^3$, $10^4$, $10^5$, $10^6$, $10^7$, $10^8$, $10^9$, $10^{10}$, $10^{11}$, $10^{12}$, $10^{13}$ pfu and higher. Alternatively, depending on the kind of virus and the titer attainable, one will deliver 1 to 100, 10 to 50, 100-1000, or up to about or at least about $1\times10^4$, $1\times10^5$, $1\times10^6$, $1\times10^7$, $1\times10^8$, $1\times10^9$, $1\times10^{10}$, $1\times10^{11}$, $1\times10^{12}$, $1\times10^{13}$, $1\times10^{14}$, or $1\times10^{15}$ or higher infectious viral particles (vp), including all values and ranges there between, to the tumor or tumor site.

B. Injectable Compositions and Formulations

The preferred method for the delivery of an expression construct or virus encoding all or part of a poxvirus genome to cancer or tumor cells in the present invention is via intratumoral injection. However, the pharmaceutical compositions disclosed herein may alternatively be administered parenterally, intravenously, intradermally, intramuscularly, transdermally or even intraperitoneally as described in U.S. Pat. Nos. 5,543,158; 5,641,515 and 5,399,363 (each specifically incorporated herein by reference in its entirety).

Injection of nucleic acid constructs may be delivered by syringe or any other method used for injection of a solution, as long as the expression construct can pass through the particular gauge of needle required for injection. A novel needleless injection system has recently been described (U.S. Pat. No. 5,846,233) having a nozzle defining an ampule chamber for holding the solution and an energy device for pushing the solution out of the nozzle to the site of delivery. A syringe system has also been described for use in gene therapy that permits multiple injections of predetermined quantities of a solution precisely at any depth (U.S. Pat. No. 5,846,225).

Solutions of the active compounds as free base or pharmacologically acceptable salts may be prepared in water suitably mixed with a surfactant, such as hydroxypropylcellulose. Dispersions may also be prepared in glycerol, liquid polyethylene glycols, and mixtures thereof and in oils. Under ordinary conditions of storage and use, these preparations contain a preservative to prevent the growth of microorganisms. The pharmaceutical forms suitable for injectable use include sterile aqueous solutions or dispersions and sterile powders for the extemporaneous preparation of sterile injectable solutions or dispersions (U.S. Pat. No. 5,466,468, specifically incorporated herein by reference in its entirety). In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous, intratumoral and intraperitoneal administration. In this connection, sterile aqueous media that can be employed will be known to those of skill in the art in light of the present disclosure. For example, one dosage may be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The compositions disclosed herein may be formulated in a neutral or salt form. Pharmaceutically-acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. Upon formulation, solutions will be administered in a manner compatible with the dosage formulation and in such amount as is therapeutically effective. The formulations are easily administered in a variety of dosage forms such as injectable solutions, drug release capsules and the like.

As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

The phrase "pharmaceutically-acceptable" or "pharmacologically-acceptable" refers to molecular entities and compositions that do not produce an allergic or similar untoward reaction when administered to a human. The preparation of an aqueous composition that contains a protein as an active ingredient is well understood in the art. Typically, such compositions are prepared as injectables, either as liquid solutions or suspensions; solid forms suitable for solution in, or suspension in, liquid prior to injection can also be prepared.

C. Combination Treatments

The compounds and methods of the present invention may be used in the context of hyperproliferative diseases/conditions including cancer. In order to increase the effectiveness of a treatment with the compositions of the present invention, such as a GM-CSF-expressing vaccinia virus, it may be desirable to combine these compositions with other agents effective in the treatment of those diseases and conditions. For example, the treatment of a cancer may be implemented with therapeutic compounds of the present invention and other anti-cancer therapies, such as anti-cancer agents or surgery.

Various combinations may be employed; for example, a poxvirus, such as vaccinia virus, is "A" and the secondary anti-cancer therapy is "B":

A/B/A B/A/B B/B/A A/A/B A/B/B B/A/A A/B/B/B B/A/B/B

B/B/B/A B/B/A/B A/A/B/B A/B/A/B A/B/B/A B/B/A/A B/A/B/A B/A/A/B A/A/A/B B/A/A/A A/B/A/A A/A/B/A

Administration of the poxvirus/vaccina vectors of the present invention to a patient will follow general protocols for the administration of that particular secondary therapy, taking into account the toxicity, if any, of the poxvirus treatment. It is expected that the treatment cycles would be repeated as necessary. It also is contemplated that various standard therapies, as well as surgical intervention, may be applied in combination with the described cancer or tumor cell therapy.

An "anti-cancer" agent is capable of negatively affecting cancer in a subject, for example, by killing cancer cells, inducing apoptosis in cancer cells, reducing the growth rate of cancer cells, reducing the incidence or number of metastases, reducing tumor size, inhibiting tumor growth, reducing the blood supply to a tumor or cancer cells, promoting an immune response against cancer cells or a tumor, preventing or inhibiting the progression of cancer, or increasing the lifespan of a subject with cancer. Anti-cancer agents include biological agents (biotherapy), chemotherapy agents, and radiotherapy agents. More generally, these other compositions would be provided in a combined amount effective to kill or inhibit proliferation of the cell. This process may involve contacting the cells with the expression construct and the agent(s) or multiple factor(s) at the same time. This may be achieved by contacting the cell with a single composition or pharmacological formulation that includes both agents, or by contacting the cell with two distinct compositions or formulations, at the same time, wherein one composition includes the expression construct and the other includes the second agent(s).

Tumor cell resistance to chemotherapy and radiotherapy agents represents a major problem in clinical oncology. One goal of current cancer research is to find ways to improve the efficacy of chemo- and radiotherapy by combining it with gene therapy. For example, the herpes simplex-thymidine kinase (HS-tK) gene, when delivered to brain tumors by a retroviral vector system, successfully induced susceptibility to the antiviral agent ganciclovir (Culver et al., 1992). In the context of the present invention, it is contemplated that poxvirus therapy could be used similarly in conjunction with chemotherapeutic, radiotherapeutic, immunotherapeutic or other biological intervention, in addition to other pro-apoptotic or cell cycle regulating agents.

Alternatively, the poxviral therapy may precede or follow the other agent treatment by intervals ranging from minutes to weeks. In embodiments where the other agent and poxvirus are applied separately to the cell, one would generally ensure that a significant period of time did not expire between the time of each delivery, such that the agent and poxvirus would still be able to exert an advantageously combined effect on the cell. In such instances, it is contemplated that one may contact the cell with both modalities within about 12-24 h of each other and, more preferably, within about 6-12 h of each other. In some situations, it may be desirable to extend the time period for treatment significantly, however, where several days (2, 3, 4, 5, 6 or 7) to several weeks (1, 2, 3, 4, 5, 6, 7 or 8) lapse between the respective administrations.

1. Chemotherapy

Cancer therapies also include a variety of combination therapies with both chemical and radiation based treatments. Combination chemotherapies include, for example, cisplatin (CDDP), carboplatin, procarbazine, mechlorethamine, cyclophosphamide, camptothecin, ifosfamide, melphalan, chlorambucil, busulfan, nitrosurea, dactinomycin, daunorubicin, doxorubicin, bleomycin, plicomycin, mitomycin, etoposide (VP16), tamoxifen, raloxifene, estrogen receptor binding agents, taxol, gemcitabien, navelbine, farnesyl-protein transferase inhibitors, transplatinum, 5-fluorouracil, vincristine, vinblastine and methotrexate, Temazolomide (an aqueous form of DTIC), or any analog or derivative variant of the foregoing. The combination of chemotherapy with biological therapy is known as biochemotherapy.

2. Radiotherapy

Other factors that cause DNA damage and have been used extensively include what are commonly known as .gamma.-rays, X-rays, and/or the directed delivery of radioisotopes to tumor cells. Other forms of DNA damaging factors are also contemplated such as microwaves and UV-irradiation. It is most likely that all of these factors effect a broad range of damage on DNA, on the precursors of DNA, on the replication and repair of DNA, and on the assembly and maintenance of chromosomes. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the neoplastic cells.

The terms "contacted" and "exposed," when applied to a cell, are used herein to describe the process by which a therapeutic construct and a chemotherapeutic or radiotherapeutic agent are delivered to a target cell or are placed in direct juxtaposition with the target cell. To achieve cell killing or stasis, both agents are delivered to a cell in a combined amount effective to kill the cell or prevent it from dividing.

3. Immunotherapy

Immunotherapeutics, generally, rely on the use of immune effector cells and molecules to target and destroy cancer cells. The immune effector may be, for example, an antibody specific for some marker on the surface of a tumor cell. The antibody alone may serve as an effector of therapy or it may recruit other cells to actually effect cell killing. The antibody also may be conjugated to a drug or toxin (chemotherapeutic, radionuclide, ricin A chain, cholera toxin, pertussis toxin, etc.) and serve merely as a targeting agent. Alternatively, the effector may be a lymphocyte carrying a surface molecule that interacts, either directly or indirectly, with a tumor cell target. Various effector cells include cytotoxic T cells and NK cells. The combination of therapeutic modalities, i.e., direct cytotoxic activity and inhibition or reduction of certain poxvirus polypeptides would provide therapeutic benefit in the treatment of cancer.

Immunotherapy could also be used as part of a combined therapy. The general approach for combined therapy is discussed below. In one aspect of immunotherapy, the tumor cell must bear some marker that is amenable to targeting, i.e., is not present on the majority of other cells. Many tumor markers exist and any of these may be suitable for targeting in the context of the present invention. Common tumor markers include carcinoembryonic antigen, prostate specific antigen, urinary tumor associated antigen, fetal antigen, tyrosinase (p97), gp68, TAG-72, HMFG, Sialyl Lewis Antigen, MucA, MucB, PLAP, estrogen receptor, laminin receptor, erb B and p155. An alternative aspect of immunotherapy is to anticancer effects with immune stimulatory effects. Immune stimulating molecules also exist including: cytokines such as IL-2, IL4, IL-12, GM-CSF, IFN.gamma., chemokines such as MIP-1, MCP-1, IL-8 and growth factors such as FLT3 ligand. Combining immune stimulating molecules, either as proteins or using gene delivery in combination with a tumor suppressor such as mda-7 has been shown to enhance anti-tumor effects (Ju et al., 2000).

As discussed earlier, examples of immunotherapies currently under investigation or in use are immune adjuvants (e.g., *Mycobacterium bovis, Plasmodium falciparum*, dinitrochlorobenzene and aromatic compounds) (U.S. Pat. Nos. 5,801,005; 5,739,169; Hui and Hashimoto, 1998; Christodoulides et al., 1998), cytokine therapy (e.g. interferons-α, -β and -γ; IL-1, GM-CSF and TNF) (Bukowski et al., 1998; Davidson et al., 1998; Hellstrand et al., 1998) gene therapy (e.g., TNF, IL-1, IL-2, p53) (Qin et al., 1998; Austin-Ward and Villaseca, 1998; U.S. Pat. Nos. 5,830,880 and 5,846,945) and monoclonal antibodies (e.g., anti-ganglioside GM2, anti-HER-2, anti-p185) (Pietras et al., 1998; Hanibuchi et al., 1998; U.S. Pat. No. 5,824,311). Herceptin (trastuzumab) is a chimeric (mouse-human) monoclonal antibody that blocks the HER2-neu receptor. It possesses anti-tumor activity and has been approved for use in the treatment of malignant tumors (Dillman, 1999). Combination therapy of cancer with herceptin and chemotherapy has been shown to be more effective than the individual therapies. Thus, it is contemplated that one or more anti-cancer therapies may be employed with the poxvirus-related therapies described herein.

Passive Immunotherapy. A number of different approaches for passive immunotherapy of cancer exist. They may be broadly categorized into the following: injection of antibodies alone; injection of antibodies coupled to toxins or chemotherapeutic agents; injection of antibodies coupled to radioactive isotopes; injection of anti-idiotype antibodies; and finally, purging of tumor cells in bone marrow.

Preferably, human monoclonal antibodies are employed in passive immunotherapy, as they produce few or no side effects in the patient. Humanized and chimeric monoclonal antibodies are also employed successfully in cancer therapy. Monoclonal antibodies used as cancer therapeutics include edrecolomab, rituximab, trastuzumab, gemtuzumab, alemtuzumab, ibritumomab, tositumomab, cetuximab, bevacizumab, nimotuzumab, and panitumamab.

It may be favorable to administer more than one monoclonal antibody directed against two different antigens or even antibodies with multiple antigen specificity. Treatment protocols also may include administration of lymphokines or other immune enhancers as described by Bajorin et al. (1988). The development of human monoclonal antibodies is described in further detail elsewhere in the specification.

Active Immunotherapy. In active immunotherapy, an antigenic peptide, polypeptide or protein, or an autologous or allogenic tumor cell composition or "vaccine" is administered, generally with a distinct bacterial adjuvant (Ravindranath and Morton, 1991; Morton et al., 1992; Mitchell et al., 1990; Mitchell et al., 1993). In melanoma immunotherapy, those patients who elicit high IgM response often survive better than those who elicit no or low IgM antibodies (Morton et al., 1992). IgM antibodies are often transient antibodies and the exception to the rule appears to be anti-ganglioside or anticarbohydrate antibodies.

Adoptive Immunotherapy. In adoptive immunotherapy, the patient's circulating lymphocytes, or tumor infiltrated lymphocytes, are isolated in vitro, activated by lymphokines such as IL-2 or transduced with genes for tumor necrosis, and readministered (Rosenberg et al., 1988; 1989). To achieve this, one would administer to an animal, or human patient, an immunologically effective amount of activated lymphocytes in combination with an adjuvant-incorporated antigenic peptide composition as described herein. The activated lymphocytes will most preferably be the patient's own cells that were earlier isolated from a blood or tumor sample and activated (or "expanded") in vitro. This form of immunotherapy has produced several cases of regression of melanoma and renal carcinoma, but the percentage of responders were few compared to those who did not respond.

4. Genes

In yet another embodiment, the secondary treatment is a gene therapy in which a therapeutic polynucleotide is administered before, after, or at the same time as an attenuated poxvirus is administered. Delivery of a poxvirus in conjunction with a vector encoding one of the following gene products will have a combined anti-cancer effect on target tissues. Alternatively, the poxvirus may be engineered as a viral vector to include the therapeutic polynucleotide. A variety of proteins are encompassed within the invention, some of which are described below. Table 2 lists various genes that may be targeted for gene therapy of some form in combination with the present invention.

Inducers of Cellular Proliferation. The proteins that induce cellular proliferation further fall into various categories dependent on function. The commonality of all of these proteins is their ability to regulate cellular proliferation. For example, a form of PDGF, the sis oncogene, is a secreted growth factor. Oncogenes rarely arise from genes encoding growth factors, and at the present, sis is the only known naturally-occurring oncogenic growth factor. In one embodiment of the present invention, it is contemplated that antisense mRNA directed to a particular inducer of cellular proliferation is used to prevent expression of the inducer of cellular proliferation.

The proteins FMS, ErbA, ErbB and neu are growth factor receptors. Mutations to these receptors result in loss of regulatable function. For example, a point mutation affecting the transmembrane domain of the Neu receptor protein results in the neu oncogene. The erbA oncogene is derived from the intracellular receptor for thyroid hormone. The modified oncogenic ErbA receptor is believed to compete with the endogenous thyroid hormone receptor, causing uncontrolled growth.

The largest class of oncogenes includes the signal transducing proteins (e.g., Src, Abl and Ras). The protein Src is a cytoplasmic protein-tyrosine kinase, and its transformation from proto-oncogene to oncogene in some cases, results via mutations at tyrosine residue 527. In contrast, transformation of GTPase protein ras from proto-oncogene to oncogene, in one example, results from a valine to glycine mutation at amino acid 12 in the sequence, reducing ras GTPase activity.

The proteins Jun, Fos and Myc are proteins that directly exert their effects on nuclear functions as transcription factors.

Inhibitors of Cellular Proliferation. The tumor suppressor oncogenes function to inhibit excessive cellular proliferation. The inactivation of these genes destroys their inhibitory activity, resulting in unregulated proliferation. The tumor suppressors p53, p16 and C-CAM are described below.

In addition to p53, which has been described above, another inhibitor of cellular proliferation is p16. The major transitions of the eukaryotic cell cycle are triggered by cyclin-dependent kinases, or CDK's. One CDK, cyclin-dependent kinase 4 (CDK4), regulates progression through the $G_1$. The activity of this enzyme may be to phosphorylate Rb at late $G_1$. The activity of CDK4 is controlled by an activating subunit, D-type cyclin, and by an inhibitory subunit, the p16$^{INK4}$ has been biochemically characterized as a protein that specifically binds to and inhibits CDK4, and thus may regulate Rb phosphorylation (Serrano et al., 1993; Serrano et al., 1995). Since the p16$^{INK4}$ protein is a CDK4 inhibitor (Serrano, 1993), deletion of this gene may increase the activity of CDK4, resulting in hyperphosphorylation of the Rb protein. p16 also is known to regulate the function of CDK6.

p16$^{INK4}$ belongs to a newly described class of CDK-inhibitory proteins that also includes p16$_B$, p19, p21, WAF1, and p27$^{KIP1}$. The p16$^{INK4}$ gene maps to 9p21, a chromosome region frequently deleted in many tumor types. Homozygous deletions and mutations of the p16$^{INK4}$ gene are frequent in human tumor cell lines. This evidence suggests that the p16$^{INK4}$ gene is a tumor suppressor gene. This interpretation has been challenged, however, by the observation that the frequency of the p16$^{INK4}$ gene alterations is much lower in primary uncultured tumors than in cultured cell lines (Caldas et al., 1994; Cheng et al., 1994; Hussussian et al., 1994; Kamb et al., 1994; Kamb et al., 1994; Mori et al., 1994; Okamoto et al., 1994; Nobori et al., 1994; Orlow et al., 1994; Arap et al., 1995). Restoration of wild-type p16$^{INK4}$ function by transfection with a plasmid expression vector reduced colony formation by some human cancer cell lines (Okamoto, 1994; Arap, 1995).

Other genes that may be employed according to the present invention include Rb, APC, DCC, NF-1, NF-2, WT-1, MEN-I, MEN-II, zac1, p73, VHL, MMAC1/PTEN, DBCCR-1, FCC, rsk-3, p27, p27/p16 fusions, p21/p27 fusions, anti-thrombotic genes (e.g., COX-1, TFPI), PGS, Dp, E2F, ras, myc, neu, raf erb, fms, trk, ret, gsp, hst, abl, E1A, p300, genes involved in angiogenesis (e.g., VEGF, FGF, thrombospondin, BAI-1, GDAIF, or their receptors) and MCC.

Regulators of Programmed Cell Death. Apoptosis, or programmed cell death, is an essential process for normal embryonic development, maintaining homeostasis in adult tissues, and suppressing carcinogenesis (Kerr et al., 1972). The Bcl-2 family of proteins and ICE-like proteases have been demonstrated to be important regulators and effectors of apoptosis in other systems. The Bcl-2 protein, discovered in association with follicular lymphoma, plays a prominent role in controlling apoptosis and enhancing cell survival in response to diverse apoptotic stimuli (Bakhshi et al., 1985; Cleary and Sklar, 1985; Cleary et al., 1986; Tsujimoto et al., 1985; Tsujimoto and Croce, 1986). The evolutionarily conserved Bcl-2 protein now is recognized to be a member of a family of related proteins, which can be categorized as death agonists or death antagonists.

Subsequent to its discovery, it was shown that Bcl-2 acts to suppress cell death triggered by a variety of stimuli. Also, it now is apparent that there is a family of Bcl-2 cell death regulatory proteins which share in common structural and sequence homologies. These different family members have been shown to either possess similar functions to Bcl-2 (e.g., $BCl_{XL}$, $Bcl_w$, $Bcl_s$, Mcl-1, Al, Bfl-1) or counteract Bcl-2 function and promote cell death (e.g., Bax, Bak, Bik, Bim, Bid, Bad, Haraliri).

5. Surgery

Approximately 60% of persons with cancer will undergo surgery of some type, which includes preventative, diagnostic or staging, curative and palliative surgery. Curative surgery is a cancer treatment that may be used in conjunction with other therapies, such as the treatment of the present invention, chemotherapy, radiotherapy, hormonal therapy, gene therapy, immunotherapy and/or alternative therapies.

Curative surgery includes resection in which all or part of cancerous tissue is physically removed, excised, and/or destroyed. Tumor resection refers to physical removal of at least part of a tumor. In addition to tumor resection, treatment by surgery includes laser surgery, cryosurgery, electrosurgery, and microscopically controlled surgery (Mohs' surgery). It is further contemplated that the present invention may be used in conjunction with removal of superficial cancers, precancers, or incidental amounts of normal tissue.

Upon excision of part of all of cancerous cells, tissue, or tumor, a cavity may be formed in the body. Treatment may be accomplished by perfusion, direct injection or local application of the area with an additional anti-cancer therapy. Such treatment may be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months. These treatments may be of varying dosages as well.

6. Other Agents

It is contemplated that other agents may be used in combination with the present invention to improve the therapeutic efficacy of treatment. These additional agents include immunomodulatory agents, agents that affect the upregulation of cell surface receptors and GAP junctions, cytostatic and differentiation agents, inhibitors of cell adhesion, agents that increase the sensitivity of the hyperproliferative cells to apoptotic inducers, or other biological agents. Immunomodulatory agents include tumor necrosis factor; interferon-α, -β, and -γ; IL-2 and other cytokines; F42K and other cytokine analogs; or MIP-1, MIP-1.beta., MCP-1, RANTES, and other chemolines. It is further contemplated that the upregulation of cell surface receptors or their ligands such as Fas/Fas ligand, DR4 or DR5/TRAIL (Apo-2 ligand) would potentiate the apoptotic inducing abilities of the present invention by establishment of an autocrine or paracrine effect on hyperproliferative cells. Increases intercellular signaling by elevating the number of GAP junctions would increase the anti-hyperproliferative effects on the neighboring hyperproliferative cell population. In other embodiments, cytostatic or differentiation agents can be used in combination with the present invention to improve the anti-hyperproliferative efficacy of the treatment Inhibitors of cell adhesion are contemplated to improve the efficacy of the present invention. Examples of cell adhesion inhibitors are focal adhesion kinase (FAKs) inhibitors and Lovastatin. It is further contemplated that other agents that increase the sensitivity of a hyperproliferative cell to apoptosis, such as the antibody c225, could be used in combination with the present invention to improve the treatment efficacy.

Apo2 ligand (Apo2L, also called TRAIL) is a member of the tumor necrosis factor (TNF) cytokine family. TRAIL activates rapid apoptosis in many types of cancer cells, yet is not toxic to normal cells. TRAIL mRNA occurs in a wide variety of tissues. Most normal cells appear to be resistant to TRAIL's cytotoxic action, suggesting the existence of mechanisms that can protect against apoptosis induction by TRAIL. The first receptor described for TRAIL, called death receptor 4 (DR4), contains a cytoplasmic "death domain"; DR4 transmits the apoptosis signal carried by TRAIL. Additional receptors have been identified that bind to TRAIL. One receptor, called DR5, contains a cytoplasmic death domain and signals apoptosis much like DR4. The DR4 and DR5 mRNAs are expressed in many normal tissues and tumor cell lines. Recently, decoy receptors such as DcR1 and DcR2 have been identified that prevent TRAIL from inducing apoptosis through DR4 and DR5. These decoy receptors thus represent a novel mechanism for regulating sensitivity to a pro-apoptotic cytokine directly at the cell's surface. The preferential expression of these inhibitory receptors in normal tissues suggests that TRAIL may be useful as an anticancer agent that induces apoptosis in cancer cells while sparing normal cells. (Marsters et al., 1999).

There have been many advances in the therapy of cancer following the introduction of cytotoxic chemotherapeutic drugs. However, one of the consequences of chemotherapy is the development/acquisition of drug-resistant phenotypes and the development of multiple drug resistance. The development of drug resistance remains a major obstacle in the treatment of such tumors and therefore, there is an obvious need for alternative approaches such as gene therapy.

Another form of therapy for use in conjunction with chemotherapy, radiation therapy or biological therapy includes hyperthermia, which is a procedure in which a patient's tissue is exposed to high temperatures (up to 106° F.). External or internal heating devices may be involved in the application of local, regional, or whole-body hyperthermia. Local hyperthermia involves the application of heat to a small area, such as a tumor. Heat may be generated externally with high-frequency waves targeting a tumor from a device outside the body. Internal heat may involve a sterile probe, including thin, heated wires or hollow tubes filled with warm water, implanted microwave antennae, or radiofrequency electrodes.

A patient's organ or a limb is heated for regional therapy, which is accomplished using devices that produce high energy, such as magnets. Alternatively, some of the patient's blood may be removed and heated before being perfused into an area that will be internally heated. Whole-body heating may also be implemented in cases where cancer has spread throughout the body. Warm-water blankets, hot wax, inductive coils, and thermal chambers may be used for this purpose.

Hormonal therapy may also be used in conjunction with the present invention or in combination with any other cancer therapy previously described. The use of hormones may be employed in the treatment of certain cancers such as breast, prostate, ovarian, or cervical cancer to lower the level or block the effects of certain hormones such as testosterone or estrogen. This treatment is often used in combination with at least one other cancer therapy as a treatment option or to reduce the risk of metastases.

TABLE 2

| Gene | Source | Human Disease | Function |
|---|---|---|---|
| Oncogenes | | | |
| Growth Factors | | | |
| HST/KS | Transfection | | FGF family member |
| INT-2 | MMTV promoter Insertion | | FGF family member |
| INTI/WNTI | MMTV promoter Insertion | | Factor-like |
| SIS | Simian sarcoma virus | | PDGF B |
| Receptor Tyrosine Kinases | | | |
| ERBB/HER | Avian erythroblastosis virus; ALV promoter insertion; amplified human tumors | Amplified, deleted Squamous cell Cancer; glioblastoma | EGF/TGF-α/ Amphiregulin/ Hetacellulin receptor |
| ERBB-2/NEU/HER-2 | Transfected from rat Glioblastomas | Amplified breast, Ovarian, gastric cancers | Regulated by NDF/ Heregulin and EGF-Related factors |
| FMS | SM feline sarcoma virus | | CSF-1 receptor |
| KIT | HZ feline sarcoma virus | | MGF/Steel receptor Hematopoieis |

TABLE 2-continued

| Oncogenes | | | |
| --- | --- | --- | --- |
| Gene | Source | Human Disease | Function |
| TRK | Transfection from human colon cancer | | NGF (nerve growth Factor) receptor |
| MET | Transfection from human osteosarcoma | | Scatter factor/HGF Receptor |
| RET | Translocations and point mutations | Sporadic thyroid cancer; Familial medullary thyroid cancer; multiple endocrine neoplasias 2A and 2B | Orphan receptor Tyr Kinase |
| ROS | URII avian sarcoma Virus | | Orphan receptor Tyr Kinase |
| PDGF receptor | Translocation | Chronic Myelomonocytic Leukemia | TEL(ETS-like Transcription factor)/ PDGF receptor gene Fusion |
| TGF-β receptor | | Colon carcinoma Mismatch mutation target | |
| NONRECEPTOR TYROSINE KINASES | | | |
| ABL | Abelson Mul.V | Chronic myelogenous Leukemia translocation with BCR | Interact with RB, RNA Polymerase, CRK, CBL |
| FPS/FES | Avian Fujinami SV; GA FeSV | | |
| LCK | Mul.V (murine leukemia virus) promoter insertion | | Src family; T cell Signaling; interacts CD4/CD8 T cells |
| SRC | Avian Rous sarcoma Virus | | Membrane-associated Tyr kinase with signaling function; activated by receptor kinases |
| YES | Avian Y73 virus | | Src family; signaling |
| SER/THR PROTEIN KINASES | | | |
| AKT | AKT8 murine retrovirus | | Regulated by PI(3)K?; regulate 70-kd S6 k? |
| MOS | Maloney murine SV | | GVBD; cystostatic factor; MAP kinase kinase |
| PIM-1 | Promoter insertion Mouse | | |
| RAF/MIL | 3611 murine SV; MH2 avian SV | | Signaling in RAS Pathway |
| MISCELLANEOUS CELL SURFACE | | | |
| APC | Tumor suppressor | Colon cancer | Interacts with catenins |
| DCC | Tumor suppressor | Colon cancer | CAM domains |
| E-cadherin | Candidate tumor Suppressor | Breast cancer | Extracellular homotypic binding; intracellular interacts with catenins |
| PTC/NBCCS | Tumor suppressor and *Drosophila* homology | Nevoid basal cell cancer Syndrome (Gorline syndrome) | 12 transmembrane domain; signals through Gli homogue CI to antagonize Hedgehog pathway |
| TAN-1 Notch homologue | Translocation | T-ALL | Signaling |
| MISCELLANEOUS SIGNALING | | | |
| BCL-2 | Translocation | B-cell lymphoma | Apoptosis |
| CBL | Mu Cas NS-1 V | | Tyrosine- Phosphorylated RING finger interact Abl |
| CRK | CT1010 ASV | | Adapted SH2/SH3 interact Abl |
| DPC4 | Tumor suppressor | Pancreatic cancer | TGF-β-related signaling Pathway |
| MAS | Transfection and Tumorigenicity | | Possible angiotensin Receptor |
| NCK | | | Adaptor SH2/SH3 |

TABLE 2-continued

Oncogenes

| Gene | Source | Human Disease | Function |
|---|---|---|---|
| GUANINE NUCLEOTIDE EXCHANGERS AND BINDING PROTEINS | | | |
| BCR | | Translocated with ABL in CML | Exchanger; protein Kinase |
| DBL | Transfection | | Exchanger |
| GSP | | | |
| NF-1 | Hereditary tumor Suppressor | Tumor suppressor Neurofibromatosis | RAS GAP |
| OST | Transfection | | Exchanger |
| Harvey-Kirsten, N-RAS | HaRat SV; Ki RaSV; Balb-MoMuSV; Transfection | Point mutations in many human tumors | Signal cascade |
| VAV | Transfection | | S112/S113; exchanger |
| NUCLEAR PROTEINS AND TRANSCRIPTION FACTORS | | | |
| BRCA1 | Heritable suppressor | Mammary Cancer/ovarian cancer | Localization unsettled |
| BRCA2 | Heritable suppressor | Mammary cancer | Function unknown |
| ERBA | Avian erythroblastosis Virus | | Thyroid hormone receptor (transcription) |
| ETS | Avian E26 virus | | DNA binding |
| EVII | MuLV promoter Insertion | AML | Transcription factor |
| FOS | FBI/FBR murine osteosarcoma viruses | | Transcription factor with c-JUN |
| GLI | Amplified glioma | Glioma | Zinc finger; cubitus Interruptus homologue is in hedgehog signaling pathway; inhibitory link PTC and hedgehog |
| HMGI/LIM | Translocation t(3:12) t(12:15) | Lipoma | Gene fusions high mobility group HMGI-C (XT-hook) and transcription factor LIM or acidic domain |
| JUN | ASV-17 | | Transcription factor AP-1 with FOS |
| MLL/VHRX + ELI/MEN | Translocation/fusion ELL with MLL Trithorax-like gene | Acute myeloid leukemia | Gene fusion of DNA-binding and methyl transferase MLL with ELI RNA pol II Elongation factor |
| MYB | Avian myeloblastosis Virus | | DNA binding |
| MYC | Avian MC29; Translocation B-cell Lymphomas; promoter Insertion avian leukosis Virus | Burkitt's lymphoma | DNA binding with MAX partner; cyclin Regulation; interact RB?; regulate Apoptosis? |
| N-MYC | Amplified | Neuroblastoma | |
| L-MYC | | Lung cancer | |
| REL | Avian Retriculoendotheliosis Virus | | NF-κB family Transcription factor |
| SKI | Avian SKV770 Retrovirus | | Transcription factor |
| VHL | Heritable suppressor | Von Hippel-Landau Syndrome | Negative regulator or elongin; transcriptional elongation complex |
| WT-1 | | Wilm's tumor | Transcription factor |
| CELL CYCLE/DNA DAMAGE RESPONSE | | | |
| ATM | Hereditary disorder | Ataxia-telangiectasia | Protein/lipid kinase Homology; DNA damage response upstream in P53 pathway |
| BCL-2 | Translocation | Follicular lymphoma | Apoptosis |
| FACC | Point mutation | Fanconi's anemia group C (predisposition Leukemia | |

TABLE 2-continued

Oncogenes

| Gene | Source | Human Disease | Function |
|---|---|---|---|
| FHIT | Fragile site 3p14.2 | Lung carcinoma | Histidine triad-related Diadenosine 5',3''''-$P^1.p^4$ tetraphosphate Asymmetric hydrolase |
| hMLI/MutL | | HNPCC | Mismatch repair; MutL Homologue |
| HMSH2/MutS | | HNPCC | Mismatch repair; MutS Homologue |
| HPMS1 | | HNPCC | Mismatch repair; MutL Homologue |
| hPMS2 | | HNPCC | Mismatch repair; MutL Homologue |
| INK4/MTS1 | Adjacent INK-4B at 9p21; CDK complexes | Candidate MTS1 Suppressor and MLM melanoma gene | p16 CDK inhibitor |
| INK4B/MTS2 | | Candidate suppressor | p15 CDK inhibitor |
| MDM-2 | Amplified | Sarcoma | Negative regulator p53 |
| p53 | Association with SV40 T antigen | Mutated >50% human Tumors, including hereditary Li-Fraumeni syndrome | Transcription factor; Checkpoint control; apoptosis |
| PRAD1/BCL1 | Translocation with Parathyroid hormone or IgG | Parathyroid adenoma; B-CLL | Cyclin D |
| RB | Hereditary Retinoblastoma; Association with many DNA virus tumor Antigens | Retinoblastoma; Osteosarcoma; breast Cancer; other sporadic Cancers | Interact cyclin/cdk; regulate E2F transcription factor |
| XPA | | Xeroderma Pigmentosum; skin Cancer predisposition | Excision repair; photo-product recognition; zinc finger |

V. Examples

The following examples are given for the purpose of illustrating various embodiments of the invention and are not meant to limit the present invention in any fashion. One skilled in the art will appreciate readily that the present invention is well adapted to carry out the objects and obtain the ends and advantages mentioned, as well as those objects, ends and advantages inherent herein. The present examples, along with the methods described herein are presently representative of preferred embodiments, are exemplary, and are not intended as limitations on the scope of the invention. Changes therein and other uses which are encompassed within the spirit of the invention as defined by the scope of the claims will occur to those skilled in the art.

Example 1

Material and Methods

Viruses and Cell Lines. The panel of wild type poxvirus strains (Wyeth, Western Reserve (WR), USSR, Tian Tan, Tash Kent, Patwadangar, Lister, King, IHD-W, IHD-J and Evans) was kindly provided by Dr Geoff Smith, Imperial College, London. Human Adenovirus serotype 5 (Ad5) was obtained from ATCC. The Viral growth factor (VGF) deleted strain of WR (vSC20) was kindly provided by Dr Bernie Moss, NIH. The thymidine kinase deleted strain of WR (vJS6) and the TK-, VGF-double deleted strain of WR (vvDD) are described in Puhlmann et al. (2000) and McCart et al. (2001). WR strain expressing firefly luciferase was kindly provided by Dr Gary Luker, (Uni Michigan).

Vaccinia strain JX-963 was constructed by recombination of a version of the pSC65 plasmid containing the E. coli gpt and human GM-CSF genes (under the control of the p7.5 and pSE/L promoters respectively) into the thymidine kinase gene of the vSC20 (VGF deleted) strain of WR. Further selection of white plaques after propagation of the virus in X-Gal produced a virus with non-functioning lacZ (lacZ is expressed from within VGF in vSC20). Correct insertion into the TK gene and loss of lacZ function was verified by sequencing and GM-CSF production verified by ELISA.

The vvDD expressing luciferase was constructed by insertion of a version of the pSC65 plasmid with luciferase under control of the p7.5 promoter into vSC20. Bioluminescence was verified using an IVIS 50 system (Xenogen, Alameda).

The human tumor cell lines include A2780 (Ovarian, obtained from ECACC), A549 (lung, obtained from ECACC), HCT 116, HT-29 and SW620 (colon, obtained from ATCC), HT-1080 (fibrosarcoma, obtained from ATCC), LNCaP (prostate, obtained from ATCC), PANC-1 (pancreatic, obtained from ATCC), MCF-7 (breast, obtained from ATCC). Non-transformed cells include MRC-5 (lung fibroblast, obtained from ATCC), Beas-2B (bronchial epithelial, kindly provided by Tony Reid, UCSD) and the primary, normal cells NHBE (Normal human bronchial epithelial) and SAEC (Small airway bronchial epithelial), both obtained from Clonetics (Walkersville, Md.).

The mouse tumor cell lines include CMT 64 (C57/B6 lung, obtained from Cancer Research UK), JC (BALB/c mammary, obtained from ATCC), MC38 (C57/B6 colon, obtained from NIH) and TIB-75 (BNL 1ME A.7R.1) (BALB/c hepatic, obtained from ATCC). The cell lines NIH 3T3 and NIH 3T3 overexpressing H-Ras were kindly provided by Richard Marais (ICR, London). The rabbit tumor cell line VX2 has been described previously (Kidd, 1940; Tjernberg, 1962; Chen et al., 2004).

In vitro replication and cytopathic effect assays. Cell lines are seeded into 6-well plates at $5 \times 10^6$ cells/well and left overnight. Virus was then added at a multiplicity of infection (MOI) of 1.0 Plaque forming units (PFU)/cell and allowed to infect for 2 h. At the end of the infection the media was changed and plates incubated for 48 h, the cells were then scraped into the media and collected. Cells were lysed by three rounds of freezing and thawing followed by sonication before serial dilutions of the crude viral lysate was added to BSC-1 cells to titer the virus. Plaque assay was performed as described previously (Earl et al., 1998). Adenovirus was titered on A549 cells (Earl et al., 1998). Studies are typically run in triplicate.

In order to assess the cytopathic effect (CPE) of the virus, cells were seeded at 1000 cells/well in 96-well plates and allowed to attach overnight. Serial dilutions of the viruses to be tested were then added to the plates in triplicate (MOI range from 100 to 0.001) and the plates incubated for a further 72 h. After this time media was replaced with media without serum and MTS (Promega) added to the plates. After 2-4 h incubation the absorbance at 450 nm was read on an ELISA plate reader. Cytopathic effect was determined as reduction in viability of a test well relative to both untreated wells containing cells only (100% viable) and cell-free wells (0% viable). Results were represented as the MOI at which 50% of the cell layer was viable (effective concentration 50%, EC50).

Mouse Syngeneic and Xenograft Tumor Model Studies. Immunocompetent mice are implanted subcutaneously with syngeneic tumor cells ($1 \times 10^6$ cells/mouse), such that JC and TIB-75 cells are implanted into BALB/c mice and MC38 and CMT 64 cells are implanted into C57/B6 mice. Certain human xenograft models involve $1 \times 10^7$ HT29 cells implanted subcutaneously into SCID mice (all mice are aged 8-10 weeks and sex matched). Once tumors reached 50-100 mm$^3$ animals are regrouped and treated as indicated. Tumor sizes were followed by caliper measurement.

Mice treated with luciferase expressing virus can be imaged using an IVIS 100 system (Xenogen, Alameda). Mice are injected intraperitoneally with luciferin (30 mg/kg) and anesthetized (2% isoflurane) prior to imaging.

Some mice are sacrificed at times indicated post-treatment and organs are recovered for viral biodistribution or immunohistochemical studies. For viral biodistribution, organs are snap frozen and ground before plaque assays are performed as described. For immunohistochemistry studies, organs are fixed in formalin before embedding in paraffin blocks for sectioning. Sections are stained with hematoxylin and eosin (H & E) and with viral coat proteins (polyclonal anti-vaccinia antibody or polyclonal antihexon antibody for adenovirus treated animals).

Rabbit Model. The implantation of VX2 tumors into the livers of New Zealand White rabbits and the measurement of tumor progression and metastasis to the lungs by CT and ultrasound scans has been described previously (Paeng et al., 2003).

Cytotoxic T-Lymphocyte (CTL) Assay. This is performed by mixing labeled peripheral blood lymphocytes (PBLs) obtained from rabbits treated as indicated with VX2 tumor cells. After a 4 h period cell apoptosis was measured by propidium iodide staining and flow cytometry.

Neutralizing Antibody Assay. Production of anti-vaccinia neutralizing antibody is measured in the plasma obtained from rabbits post-treatment. Dilutions of plasma are mixed with 1000 PFU of vaccinia overnight before addition to a 96-well plate containing A2780 cells. After 72 h cell viability is measured by MTS assay. Viral neutralization is measured as the dilution of plasma required to prevent viral inactivation.

Statistical Analyses. Kaplan-Meier curves are compared using the Generalized Wilcoxin test. Tumor response rates and metastasis-free rates are typically compared with Fisher's exact test.

Example 2

Rat Tumor Model

Rats (Sprague-Dawley, Males) were exposed to carcinogen (N-Nitrosomorpholine, NNM) in their drinking water (175 mg/L) for a period of 8 weeks, during which time liver cirrhosis developed, followed by in situ development of tumors (hepatocellular carcinoma or cholangiocarcinoma) within the liver between weeks 16-20 on average (model previously described in Oh et al., 2002). Tumor detection and evaluation was performed by an experienced ultrasonographer using ultrasound imaging. Tumor sizes were approximately 0.75-1.5 cm. in diameter at baseline immediately prior to treatment initiation; tumor volumes were not significantly different at baseline between the control and treatment groups (estimated mean volumes were 400-500 mm$^3$). Control animals (n=17) received no treatment, whereas treated animals (n=6) received intravenous injections (via tail vein) with a poxvirus (Wyeth strain; thymidine kinase gene deletion present) expressing human GM-CSF from a synthetic early-late promoter (virus construct described in Mastrangelo et al., 1999). Virus was administered at a dose of $10^8$ plaque-forming units (titered as in Earl et al., 1998) in a total volume of 0.75 ml; (virus suspension mixed with 10 mM Tris up to the desired volume) intravenously by tail vein over 60 seconds. Treatment was repeated every two weeks for three total doses (day 1, 15 and 29).

Over ten weeks following the initiation of treatment, the control tumors increased in size significantly until reaching a mean of approximately 3000 mm$^3$ (S.E. 500) (FIG. 1). Control animals needed to be sacrificed for ethical reasons due to tumor progression at this time. All tumors had increased in size significantly. In contrast, five of the six treated tumors regressed completely (below the limit of detection by ultrasound). The mean tumor volume in the treated group was approximately 50 mm$^3$ (S.E., <10; p<0.01 vs. controls).

Example 3

Rabbit VX2 Tumor Model

Figure 2A:
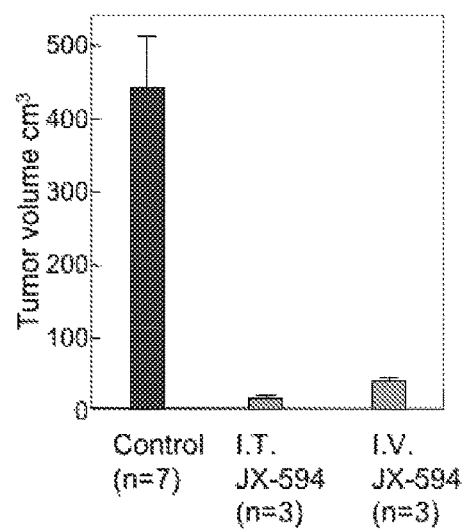
FIGS. 2A-2B—JX-594 Intravenous dose treatment of VX2 liver tumors in rabbits, efficacy against primary tumor and metastases. VX2 cells (from a dissociated 1 mm$^3$ tumor) were implanted into the liver of New Zealand white rabbits and tumor growth followed by ultrasound (US) and CT scan. Once tumors reached 2-4 cm$^3$ animals were treated with a single dose of PBS (n=7) or JX-594 (1×10$^9$ PFU), via intravenous or US guided IT injection (n=3/group).
Figure 2B:
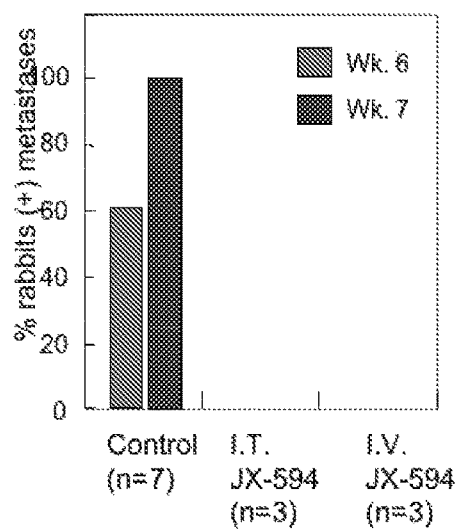

A study was performed in a VX2 rabbit carcinoma model (as described in Paeng et al., 2003). Rabbit was selected as a species because human GM-CSF was previously demonstrated to have significant biological activity in rabbits (in contrast to mice). VX2 tumors were grown in muscle of New Zealand white rabbits and cells from a 1-2 mm$^3$ fragment of tumor were dissociated, resuspended in 0.1 ml normal saline and were injected beneath the liver capsule (21 gauge needle; injection site covered with surgical patch with a purse-string tie) and allowed to grow for 14 days until primary tumors were established (mean diameter, 1.5-2.0 cm; est. volume 2-4 cm$^3$). VX2 cells were demonstrated to be infectable by vaccinia poxvirus ex vivo in a standard burst assay. Tumor sizes were monitored over time by CT scanning and by ultrasound. Over the following seven weeks, control (untreated) animals (n=18) developed tumor progression within the liver, with estimated mean tumor volumes reaching approximately 100 cm$^3$ (S.E. approximately 20). In addition, numerous tumor metastases progressed and became detectable within the lungs and livers over time (FIGS. 2A-B). By week 7, control animals all had detectable metastases, with a mean number of lung metastases of 17 (S.E. 2.3). The median survival of these control animals was 55 days (post-treatment initiation in treated animals), and all were dead within 80 days.

Treated animals (n=3) in the first experiment received a single intravenous injection (via tail vein) with a poxvirus (Wyeth strain; thymidine kinase gene deletion present) expressing human GM-CSF from a synthetic early-late promoter (virus construct described in Mastrangelo et al., 1999). Virus was administered at a dose of $10^9$ plaque-forming units (titered as in Earl et al., 1998) in a total volume of 7 ml; (virus suspension mixed with 10 mM Tris up to the desired volume) intravenously by ear vein over 60 seconds. By week seven, in contrast to controls, treated animals had no lung metastases detectable by CT scanning (FIGS. 2A-2B). Survival was significantly increased, also. By 110 days post-treatment initiation, the median survival had not been reached, and approximately 70% were still alive.

Figure 3:
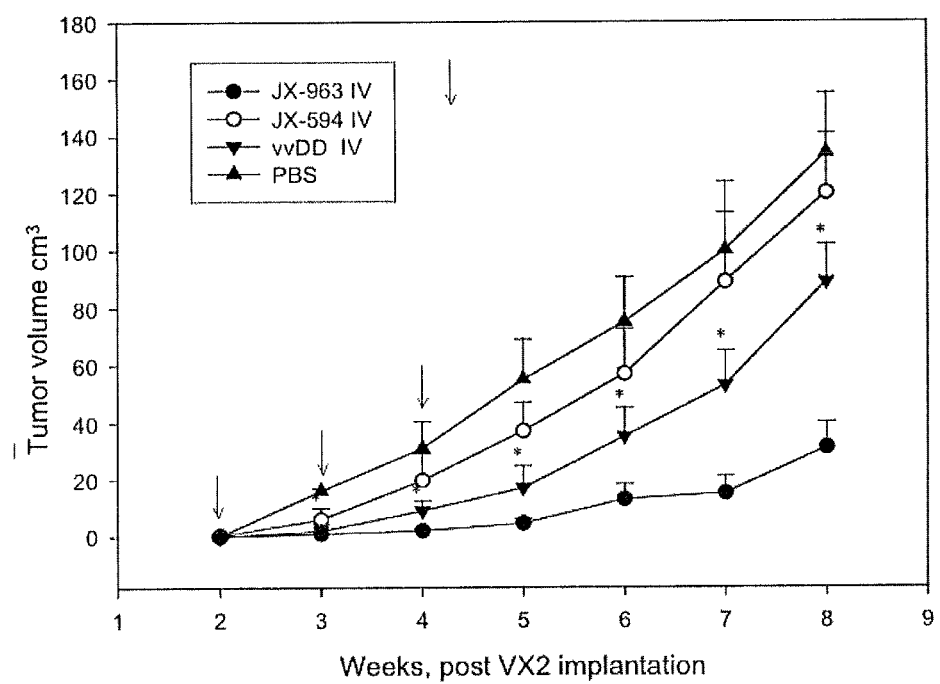
FIG. 3—JX-594 and JX-963 lower dose intravenous repeat treatments of VX2 liver tumors in rabbits. Tumor cells were implanted as described in (FIGS. 2A-2B). Animals were treated intravenously 3 times (every two weeks, arrows) after tumors reached 2-4 cm$^3$ with 1×10$^8$ PFU of JX-594, JX-963 or vvDD (n=6/group), or PBS (n=18). Subsequent primary tumor volume was followed by CT scan.
Figure 4:
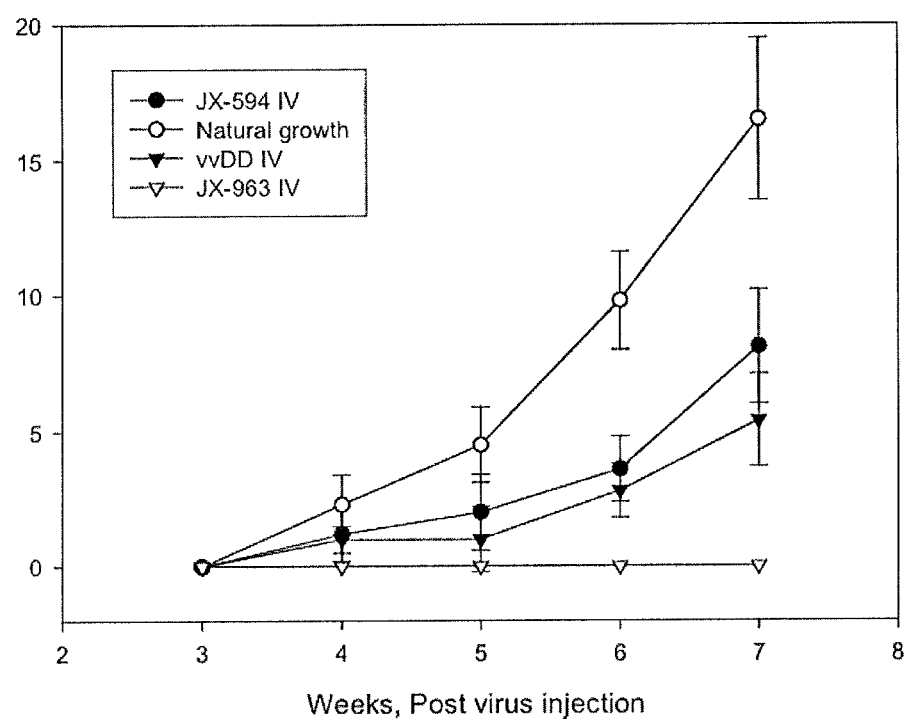
FIG. 4—Effects of JX-594, vvDD and JX-963 on lung metastases in rabbits bearing VX2 liver tumors. Animals (from studies described in FIG. 3) were examined for liver metastases by CT scan at weekly intervals after the beginning of therapy. The mean number of detectable metastases per animal in each group is shown.
Figure 5:
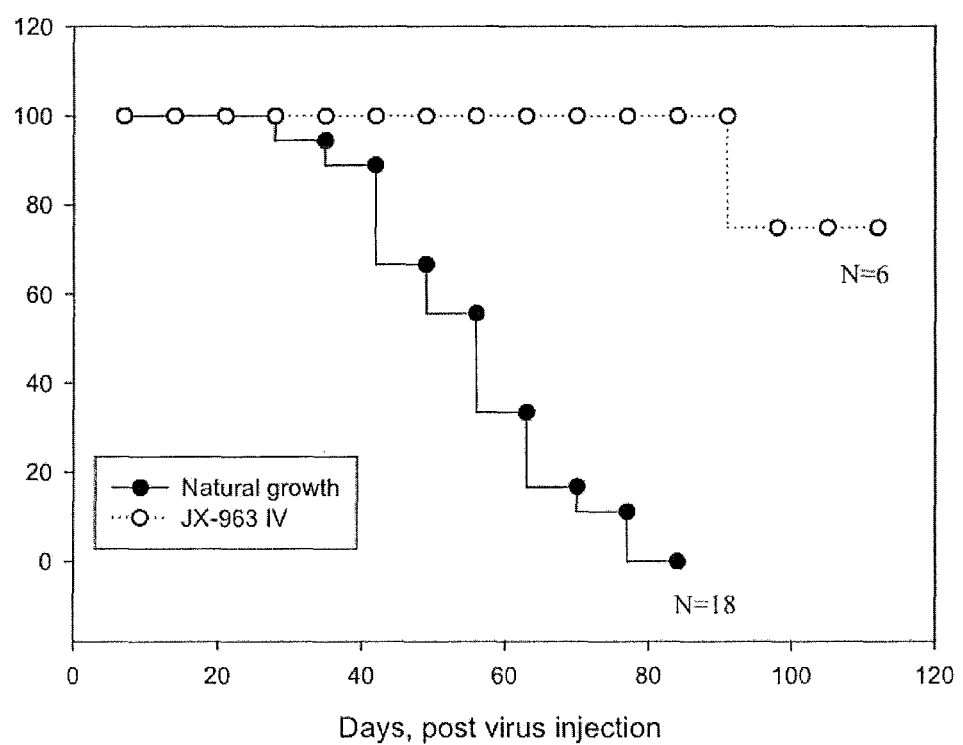
FIG. 5—Survival of rabbits bearing VX2 liver tumors after IV delivery of JX-963. Animals bearing liver tumors were treated with 3 doses of 1×10$^8$ PFU of JX-963 as described in FIG. 3. A Kaplin-Meier survival curve of these animals and the control treated group are shown. As the JX-594 and vvDD groups did not show significant differences in survival, JX594 and vvDD groups were not included.

Treated animals (n=6 per group) in a second experiment received three weekly intravenous injections (via tail vein) with either JX-594, a poxvirus (Wyeth strain; thymidine kinase gene deletion present) expressing human GM-CSF from a synthetic early-late promoter (virus construct described in Mastrangelo et al., 1999, which is hereby incorporated by reference), vvDD, a vaccinia WR strain with deletions in thymidine kinase and vaccinia growth factor genes (vvDD as described by McCart et al., 1999), or JX-963, vaccinia WR strain with deletions in thymidine kinase and vaccinia growth factor genes and expressing human GM-CSF from a synthetic early-late promoter. Virus was administered at a dose of $10^8$ plaque-forming units (titered as in Earl et al., 1998) in a total volume of 7 ml; (virus suspension mixed with 10 mM Tris up to the desired volume) intravenously by ear vein over 60 seconds. By week seven, in contrast to controls, JX-963 treated animals had no lung metastases detectable by CT scanning (p<0.01 vs. controls) (FIG. 4). JX-594-treated animals had a mean of 8 lung tumors (S.E. 2; p<0.05 vs controls). vvDD-treated animals had a mean of 5 lung tumors (S.E. 2; p<0.05 vs controls). Of note, JX-963 and vvDD also had significant efficacy against the primary tumor growth in the liver, in contrast to JX-594 at this dose (FIG. 3) and JX-963 dramatically increased the survival of these animals (FIG. 5).

The GM-CSF-expressing virus JX-963 had significantly better efficacy against both primary tumors and lung metastases than its non-GM-CSF-expressing control vvDD; 2) the GM-CSF-expressing virus JX-963 had significantly better efficacy against both primary tumors and lung metastases than its GM-CSF-expressing Wyeth strain control (despite an additional deletion in the vgf gene not present in JX-594). Therefore, intravenous administration with a vaccinia expressing human GM-CSF resulted in significantly better efficacy over the same vaccinia without GM-CSF, and intravascular administration of a WR strain deletion mutant expressing human GM-CSF was significantly better than a Wyeth strain (standard vaccine strain) deletion mutant expressing GM-CSF.

Example 4

Systemic Cancer Efficacy with JX-963

Targeted therapies hold great promise for the treatment of cancer, but novel agents are still needed as resistance frequently develops through mutation of the target molecules and/or tumor escape through pathway redundancies. Oncolytic viruses are viruses that have their replication restricted to malignant cell types, either inherently or through genetic engineering (Thorne et al., 2005)[1]. Selective intratumoral replication leads to virus multiplication, killing of the infected cancer cell by unique and apoptosis-independent mechanisms (oncolysis) and spread of the virus to other tumor cells. Virotherapeutics therefore have the potential to effectively treat refractory cancers and clinical proof-of-concept has been achieved with local or regional administration for several oncolytic viruses (Parato et al., 2005)[2]. However, for oncolytic viruses to have a major impact on patient survival, systemic efficacy and intravenous delivery will be needed.

Figure 10A:
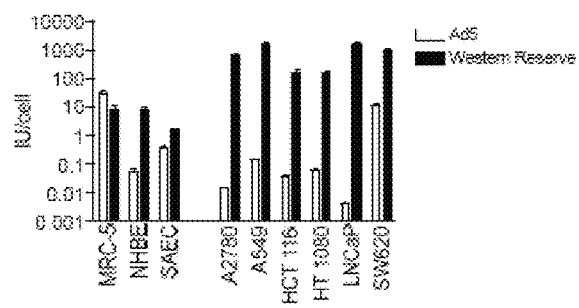
FIGS. 10A-10B—Viral production of cell lines infected with either WR or Ad5, and cytopathic effect produced by viral infection.

The inventor has therefore undertaken a stepwise design and development strategy to create a more effective systemic agent. First, the inventor identified poxviruses such as vaccinia as a virus species that has evolved for systemic dissemination and resistance to clearance by complement and antibodies (Smith et al., 1997; Buller and Palumbo, 1991). Vaccinia has well-defined mechanisms to allow for transport in the blood without inactivation and can spread rapidly within tissues, it also has a long history of human use during the smallpox eradication campaign. A panel of vaccinia viruses used during the vaccination program, and some related strains were screened for their ability to replicate in normal (NHBE) and tumor (A2780) cells. All vaccinia strains replicated to higher levels in the tumor cell line than in the normal cells (FIG. 6A), but the therapeutic index (tumor to normal cell replication ratio) varied between strains. Strains used extensively in the laboratory (such as Western Reserve (WR)) tended to display greater inherent tumor selectivity in vitro than their parental vaccine strains (Wyeth). This is the first time that wild type vaccinia strains have been shown to display inherent superior replication in tumor cell lines relative to normal cells. This is not true for all viruses however, as Adenovirus serotype 5 (Ad5) (the backbone for the majority of oncolytic viruses in the clinic) did not display such selectivity (FIG. 10A).

Another desirable attribute for an oncolytic agent is rapid intratumoral spread (Wein et al., 2003). This can be achieved through a short replication cycle and early release of virus from infected cells. The ability of the WR strain of vaccinia to destroy tumor cells was therefore examined at early time points (72 h) after infection and compared to Ad5 and the oncolytic adenovirus strain dl 1520 (ONYX-015) (Heise et al., 1997) (FIG. 6B). WR displayed up to 5-logs of increased killing potential in tumor cells at this time relative to both Ad5 and dl 1520, as well as greater tumor selectivity than either adenoviral strain.

Figure 10B:
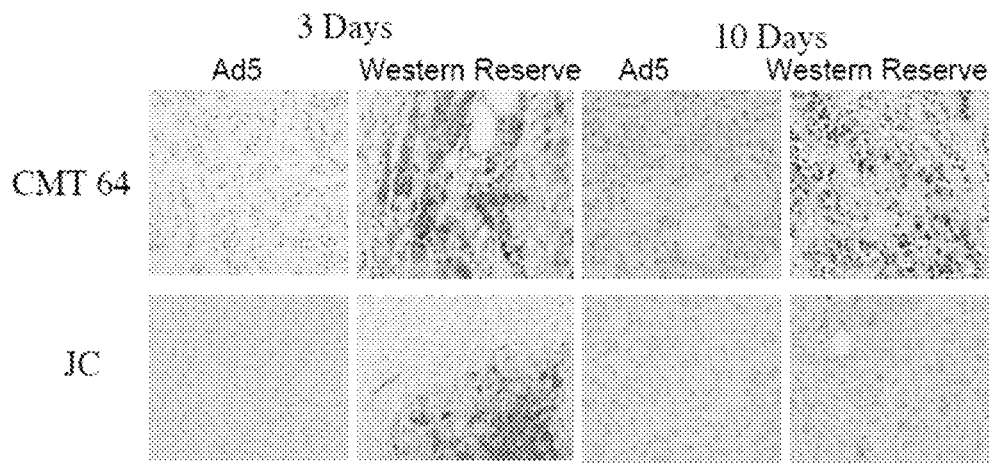

The major limitation of most oncolytic viruses tested to date is an inability to efficiently infect tumors following systemic delivery, as seen when $1 \times 10^9$ plaque forming units (PFU) of Ad5 were delivered intravenously to subcutaneous tumor models in mice (FIG. 6C and FIG. 10B); this equates to a dose of $3.5 \times 10^{12}$ PFU in a 70 kg human, higher than ever given to a patient. Little or no replicating virus was evident in tumors (as detected by immunohistochemical staining for viral coat proteins 48 and 72 h after viral delivery). Vaccinia strain WR however could effectively traffic to and infect the tumors in these same models, with up to 50% of the tumor cells staining positive within 48 h of treatment. Furthermore, vaccinia was able to persist in the tumor for at least 10 days (FIG. 10B), despite the fact an immune response would have been initiated by this time.

Figure 7:
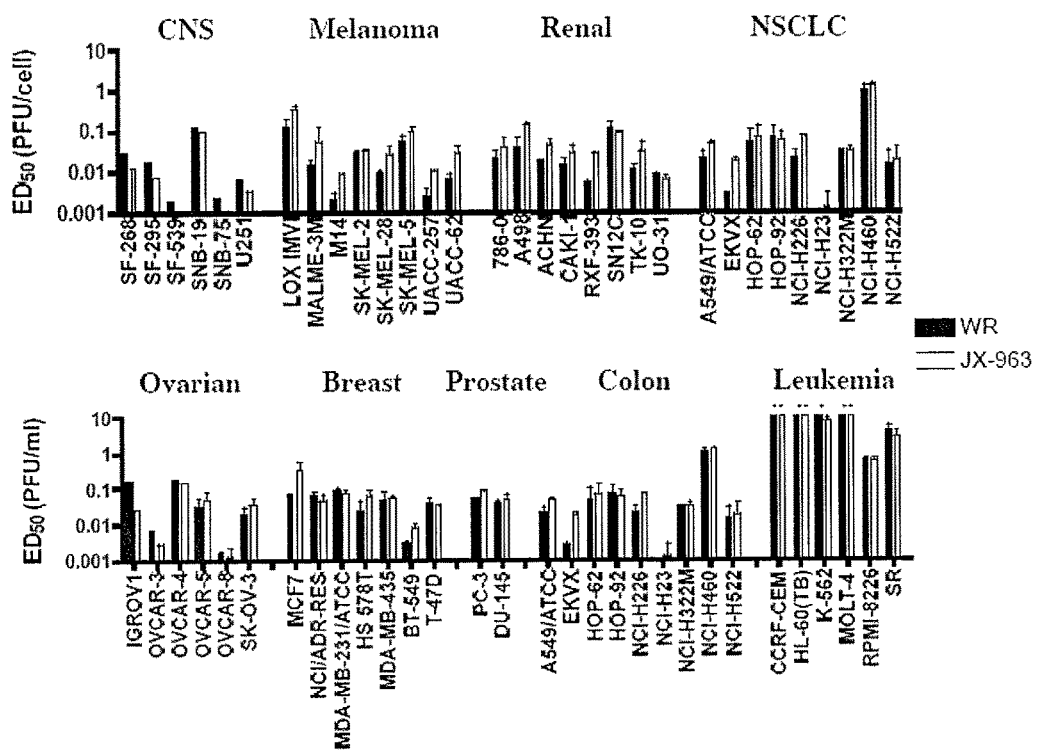
FIG. 7—Cytopathic effect of WR and vvDD on a panel of human tumor cell lines. EC$_{50}$ values were determined 72 h following infection of tumor cell lines with WR or vvDD. The MOI of virus (PFU/cell) needed to reduce the cell viability to 50% of untreated control wells (ED$_{50}$) is plotted.
Figure 11:
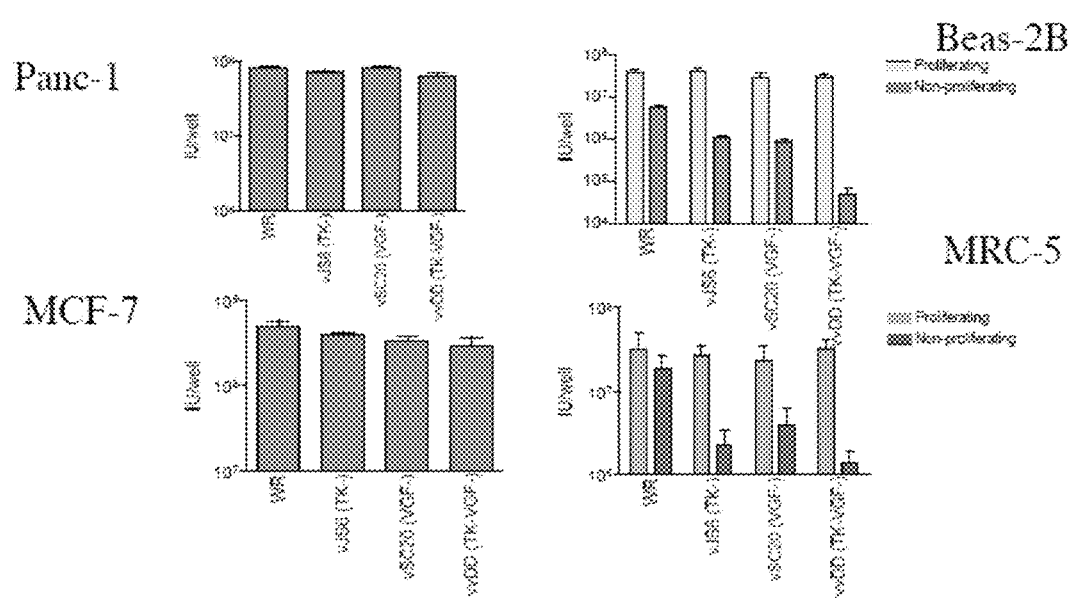
FIG. 11—Viral production of cell lines infected with either WR or Ad5. Human tumor cell lines (Panc-1 and MCF-7) or human immortalized but non-transformed cell lines (Beas-2B and MRC-5), either proliferating or grown to contact inhibition (N.B. tumor cells did not become contact inhibited), were treated with different strains of vaccinia at an MOI of 1.0 PFU/cell. Strains used were Western Reserve (WR) and WR containing deletions in either the Thymidine Kinase (TK) gene (vJS6), the viral growth factor (VGF) gene (vSC20), or containing deletions in both these genes (vvDD). Virus produced after 48 h was titered by plaque assay.

In order to maximize safety, particularly for intravenous administration in immunodeficient cancer patients, attenuating and tumor-targeting genetic deletions were introduced into the virus. The inventor has previously described preferential tumor-expression of viral genes with insertions into the vaccinia thymidine kinase (TK) gene and of TK and viral growth factor (VGF) double deletions (Puhlmann et al., 1999; McCart et al., 2001). Although the targeting mechanisms of these deletions were not previously demonstrated, the rationale was to restrict virus replication and oncolysis to cancer cells with elevated E2F levels (as E2F drives production of the cellular thymidine kinase gene product (Hengstschlager et al. 1994)) and activation of the epidermal growth factor (EGF) receptor pathway (as activation of this pathway by VGF is necessary for efficient viral replication (Andrade et al., 2004)). Here it is shown that the TK and VGF double deleted virus (vvDD) displayed an impressive ability to destroy a wide range of tumor cells of different origins (FIG. 7). It was also found that single deletions in either the vaccinia TK or the VGF genes attenuated the ability of vaccinia to replicate in non-proliferating, non-transformed human cell lines, while the double deleted virus (vvDD) was further attenuated (FIG. 11). None of these strains were attenuated in their ability to replicate in human tumor cells.

Figure 8A:
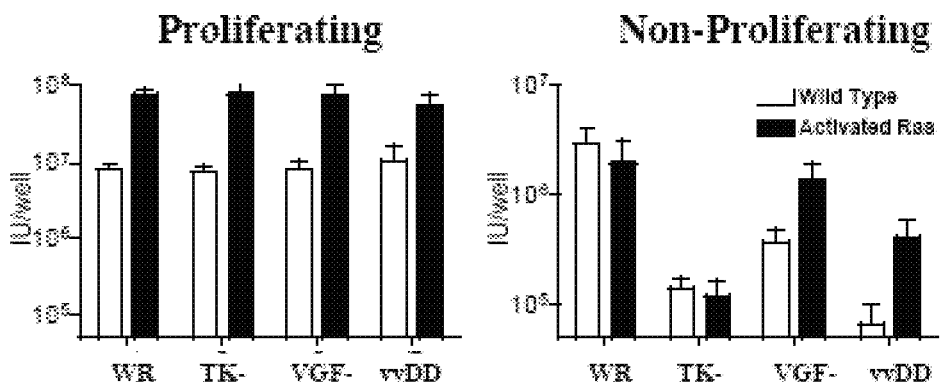
FIGS. 8A-8C—Effects of overexpression of H-Ras on viral replication, biodistribution of WR and vvDD following systemic delivery to tumor bearing mice, and viral gene expression quantified by light production.

It was further found that the block in the ability of the VGF-deleted virus to replicate in non-proliferating, non-transformed cells could be overcome in cells expressing activated H-ras (FIG. 8A). It was found that H-ras activation led to increased replication of even WR (p=0.0094), and that VGF deletion did not inhibit viral replication in H-ras activated cells, whereas the TK deletion did (p=0.016). This indicates that the tumor selectivity introduced by the gene deletions in vvDD is more than a simple preference for proliferating cells, since slowly proliferating or even non-proliferating cells could be targeted if they contained mutations in the EGF-R/Ras/MAP Kinase signaling pathway.

Figure 8B:
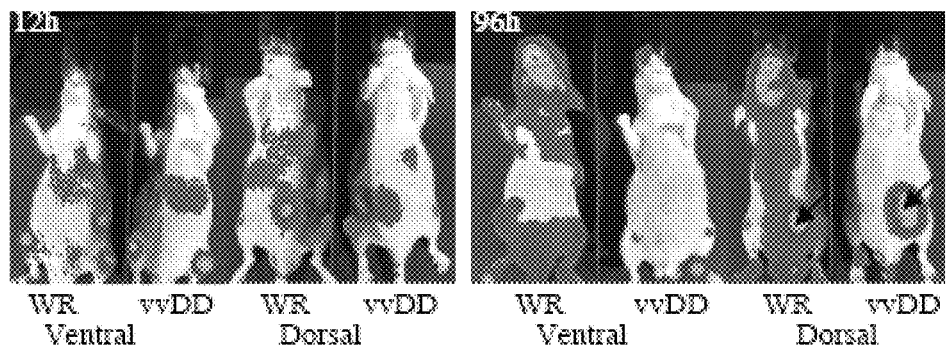
Figure 8C:
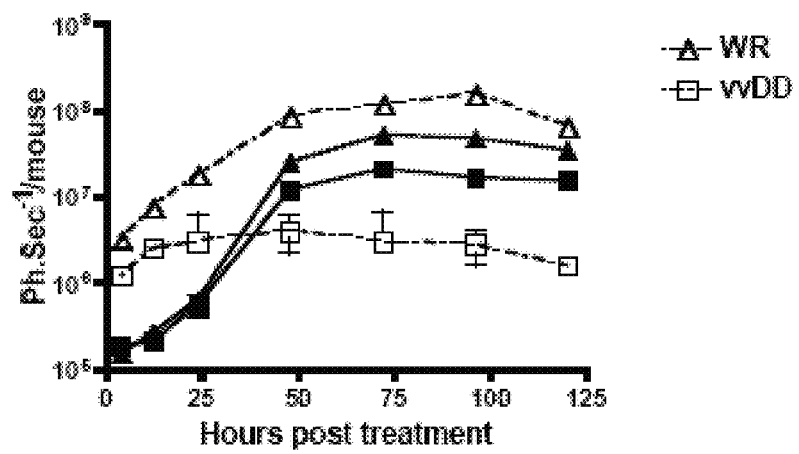
Figure 12:
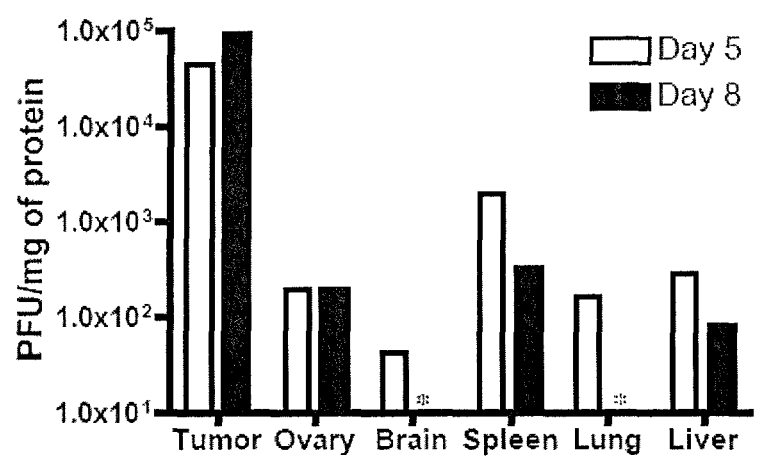
FIG. 12—Recovery of systemically delivered vvDD. Recovery of vvDD delivered systemically (intraperitoneal injection of $1 \times 10^9$ PFU) to C57B/6 mice bearing subcutaneous MC38 tumors. Mice were sacrificed on days 5 or 8 after treatment (n=8/group) and different tissues recovered and viral infectious units (PFU/mg tissue) titered by plaque assay (*=below the limits of detection).

In order to determine whether the double deleted vaccinia (vvDD) might produce toxicity by targeting normal proliferating cells (such as gut epithelial, bone marrow or ovarian cells), in vivo viral gene expression was studied by non-invasive bioluminescence imaging (FIG. 8B) and viral biodistribution was examined post mortem (FIG. 12). Bioluminescence imaging following IV delivery of $1\times10^7$ PFU of WR or vvDD expressing luciferase showed that both viruses displayed similar initial infection and viral gene expression patterns (including spleen, lung, liver and tumor) (FIG. 8B). However, the bioluminescent signal from vvDD was rapidly cleared from most organs other than the tumor, even in immunodeficient mice, while WR continued to replicate in the target organs and spread to other tissues, including bone marrow, skin and brain (FIGS. 8B and 8C). Although vvDD did produce some points of infection outside of the tumor, these appeared transiently and late, indicating secondary spread without replication (data not shown). Recovery of infectious viral units from tissues of mice treated IV with $1\times10^9$ PFU of vvDD (a lethal dose for WR) revealed that by day 8 after treatment the tumor displayed increasing viral titer, with over 1,000-fold more viral copies per mg tissue than any other organ, while all normal tissues were below the limits of detection or showed falling viral titers (FIG. 12).

Figure 13A:
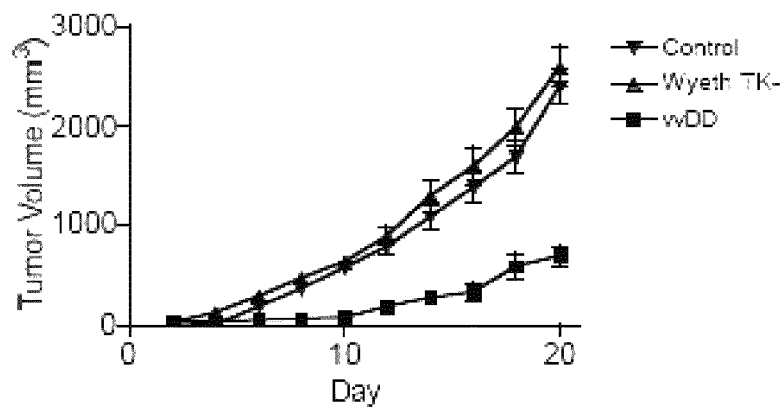
FIGS. 13A-13B—Efficacy of vvDD following delivery by different routes into tumor bearing mouse models.
Figure 13B:
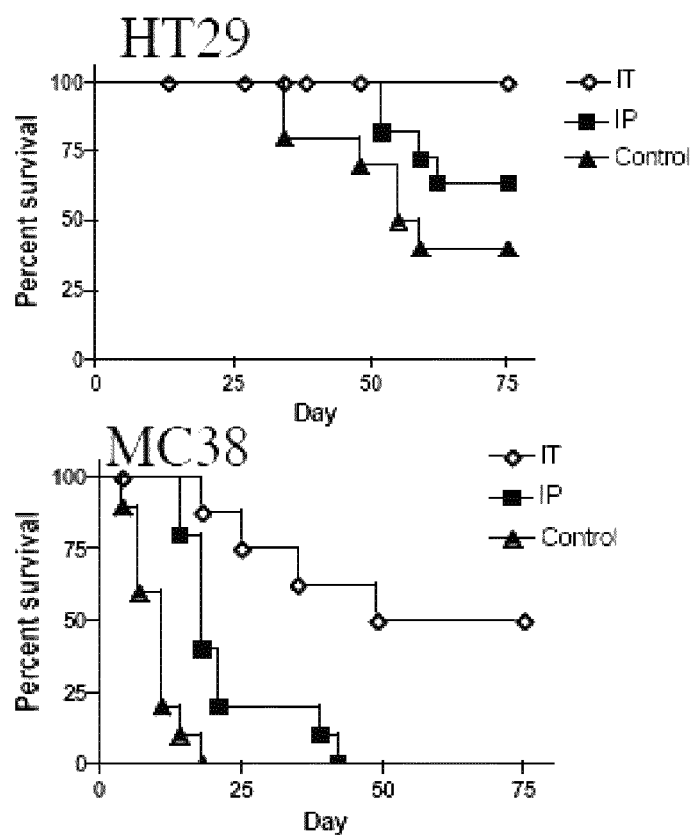

The anti-tumor effects of vvDD were then analyzed in immunocompetent mouse models. vvDD had significantly greater anti-tumor effects than a Wyeth TK deleted vaccinia strain (the most common vaccinia strain in clinical trials, usually used as a vaccine) when both were delivered intravenously (FIG. 13). Further studies showed that $1\times10^9$ PFU of vvDD was capable of significant anti-tumor effects when delivered by either systemic or intratumoral injection to both immunodeficient mice carrying human tumor xenografts and immunocompetent mice bearing syngeneic tumors (FIG. 13).

In order to increase the anti-tumor potential of vvDD, and to suppress the outgrowth of microscopic tumor deposits that are not vascularized at the time of IV dosing, the cytokine GM-CSF was inserted into the site of the TK gene (under the control of the synthetic E/L promoter); this virus was designated JX-963. Because human GM-CSF is not active in rodents but is active in rabbits (Cody et al., 2005), and in order to assess the activity against much larger primary tumors that reproducibly metastasize, JX-963 was used in a rabbit model with primary (VX2) liver tumors and lung metastases (Kim et al., 2006). As in the mouse models, $1\times10^9$ PFU of intravenous vvDD had significant anti-tumor effects (FIG. 9A). The vvDD virus was also capable of inhibiting the outgrowth of microscopic lung metastases. In order to assess additional efficacy due to concomitant GM-CSF expression, JX-963 was compared directly to vvDD. JX-963 produced greater efficacy against the primary tumor, and completely blocked outgrowth of lung metastases. GM-CSF was detected in the plasma of JX-963 treated mice by ELISA (data not shown). In addition to direct oncolytic effects, JX-963 was also found to cross-protect the animal against the tumor by raising a CTL response against the VX2 tumor cells (FIG. 9B).

Figure 14:
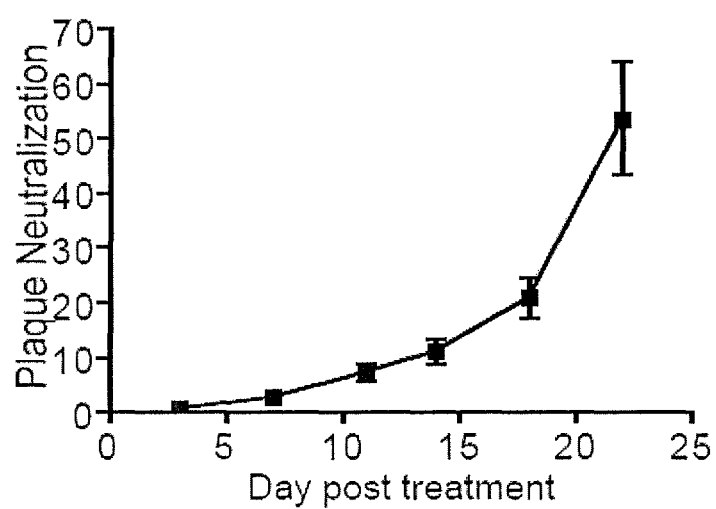
FIG. 14—Formation of neutralizing antibodies following treatment of VX2 tumor bearing rabbits with JX-963 ($1 \times 10^8$ PFU). Dilutions of plasma obtained from rabbits at indicated times were incubated with a known number of viral PFU, and dilutions required to retain 50% of the plaques are shown (n=3).
Figure 17:
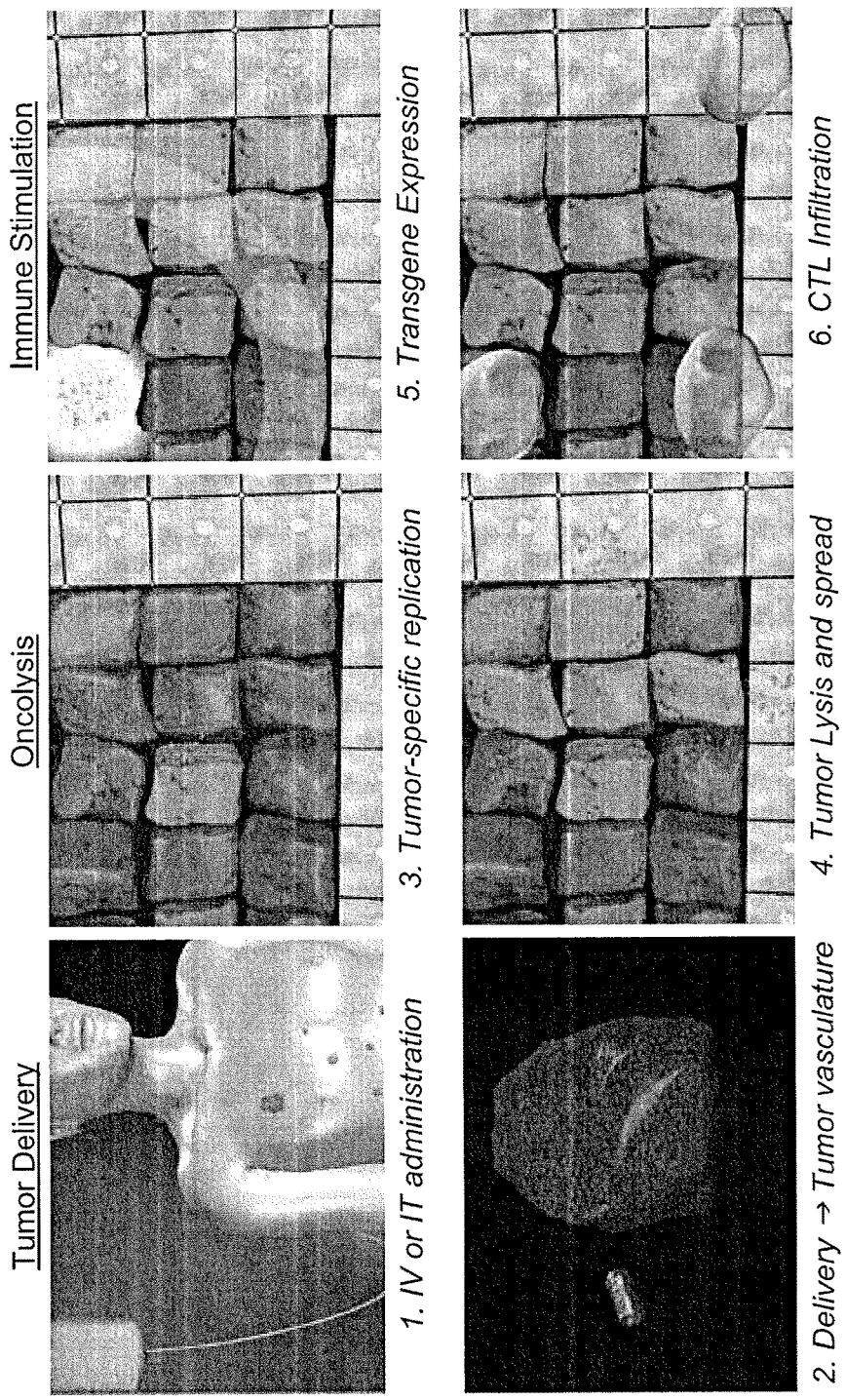
FIG. 17. Targeted oncolytic virotherapy having multiple, novel mechanisms for cancer eradication.
Figure 18:
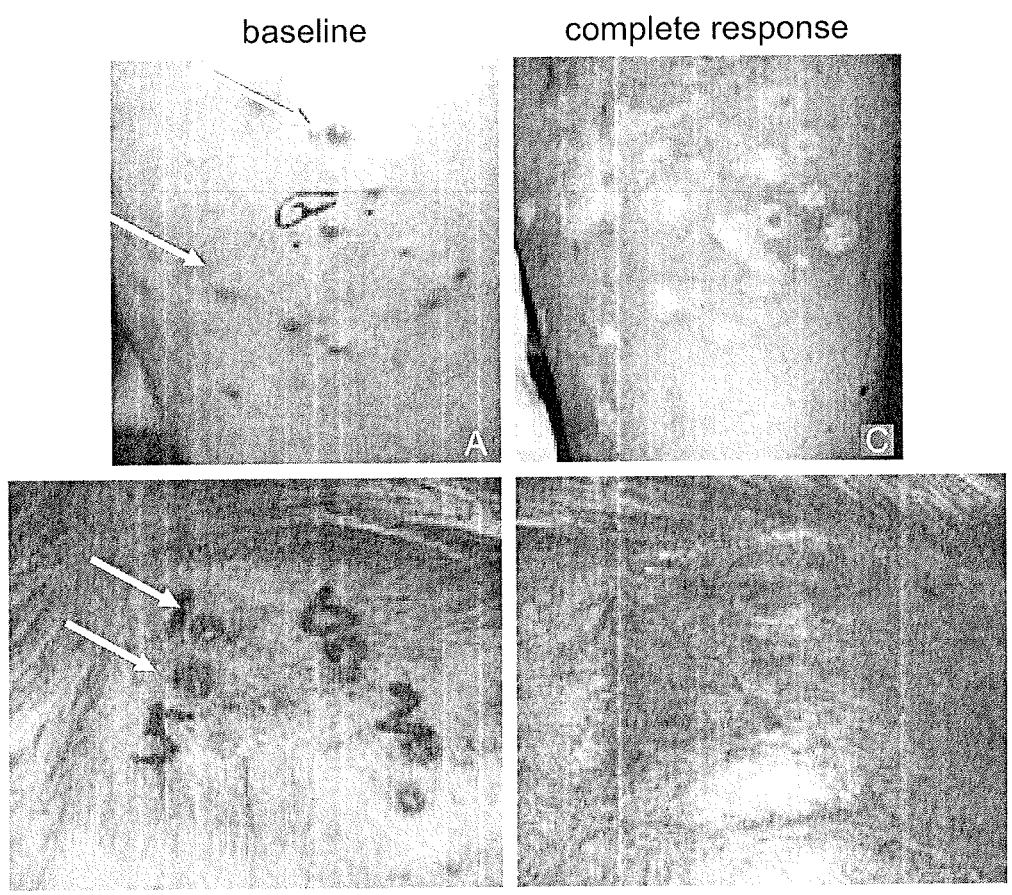
FIG. 18. Long-term survivors disease-free after JX-594 phase I clinical trial metastatic melanoma. Patient 1, top, is a 32 year-old woman: Refractory: DTIC, IL-2; injected tumors: CR; non-injected metastases: −dermal: CR; breast: CR with surgery. Alive, disease-free 1.5+ years. Patient 2, bottom, 75 year-old man: multiple metastatic sites (n=24); injected tumors: CR; non-injected metastases: −CR; Alive, disease-free 3+ years.
Figure 19:
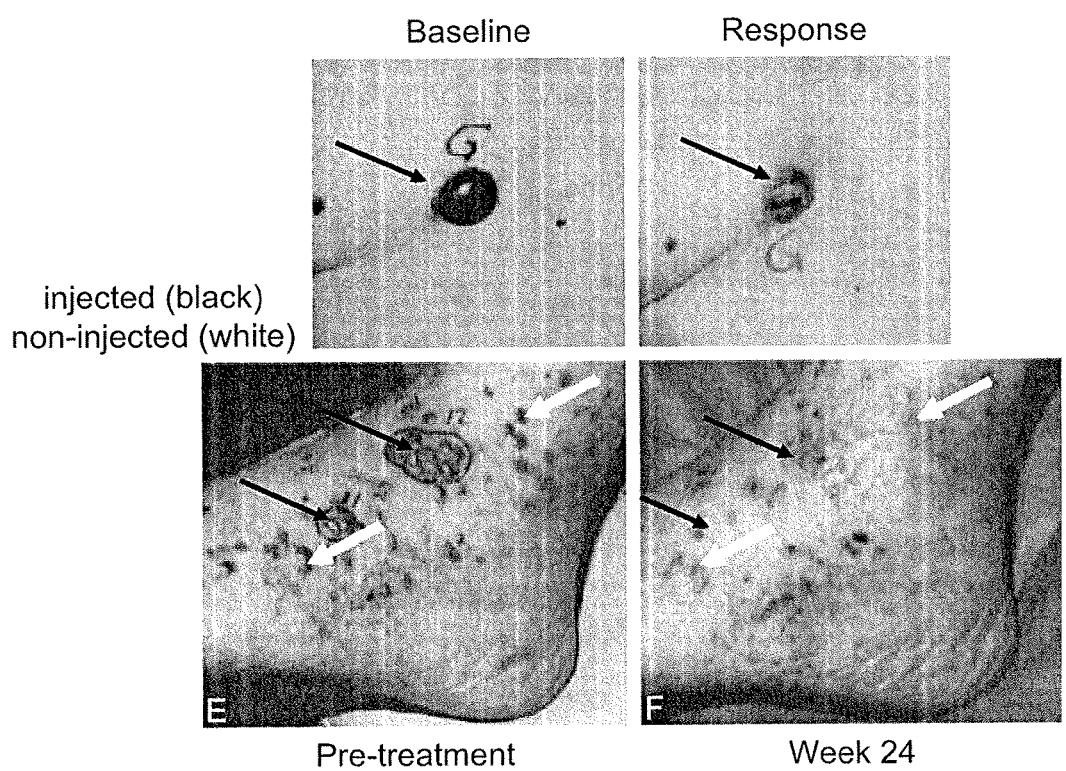
FIG. 19. JX-594 phase I clinical trial responses in both injected and non-injected tumors.
Figure 22:
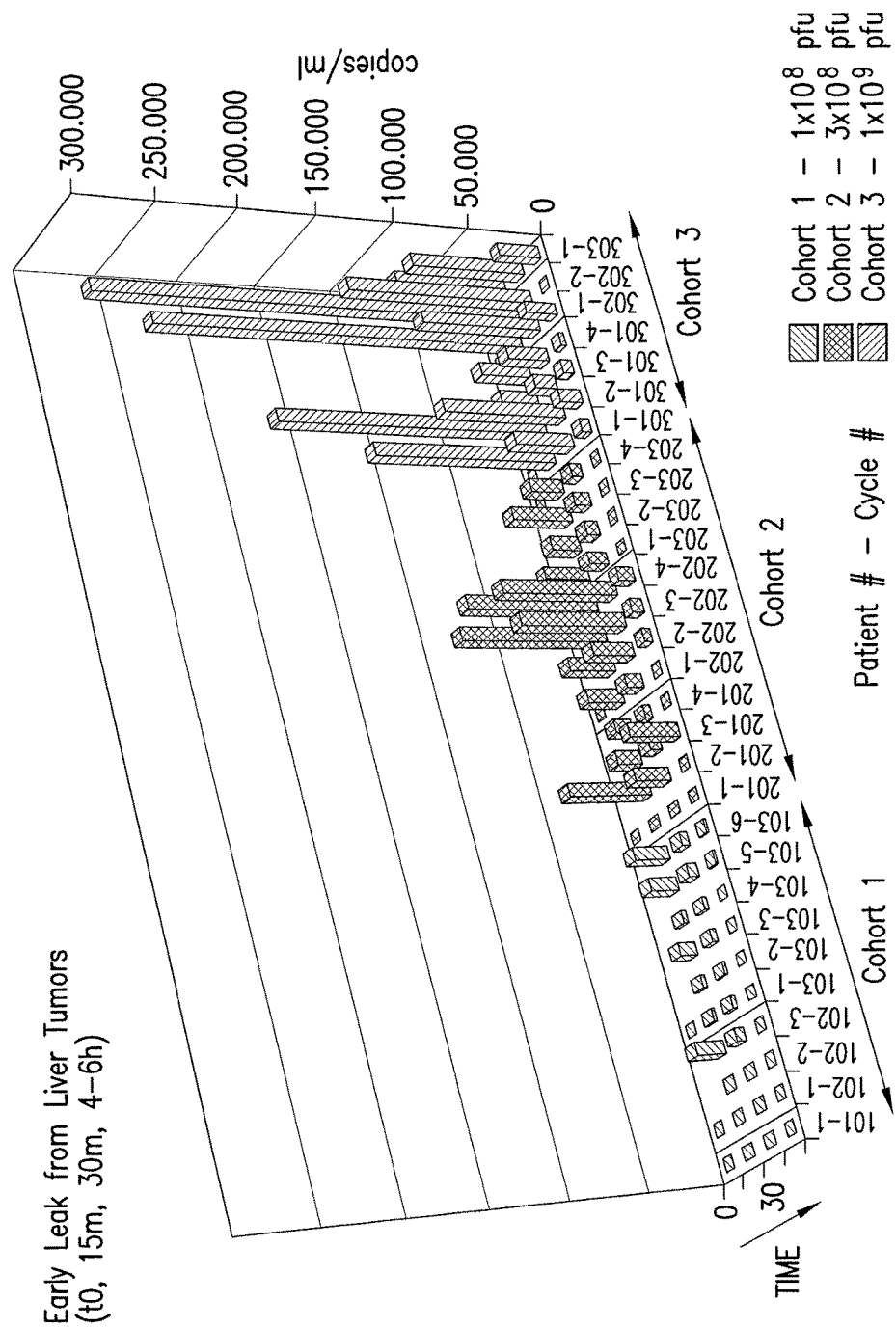
FIG. 22. Intravenous dissemination of JX-594 in bloodstream: early leak from tumor corresponds with dose, mostly cleared by 6 hrs.
Figure 24:
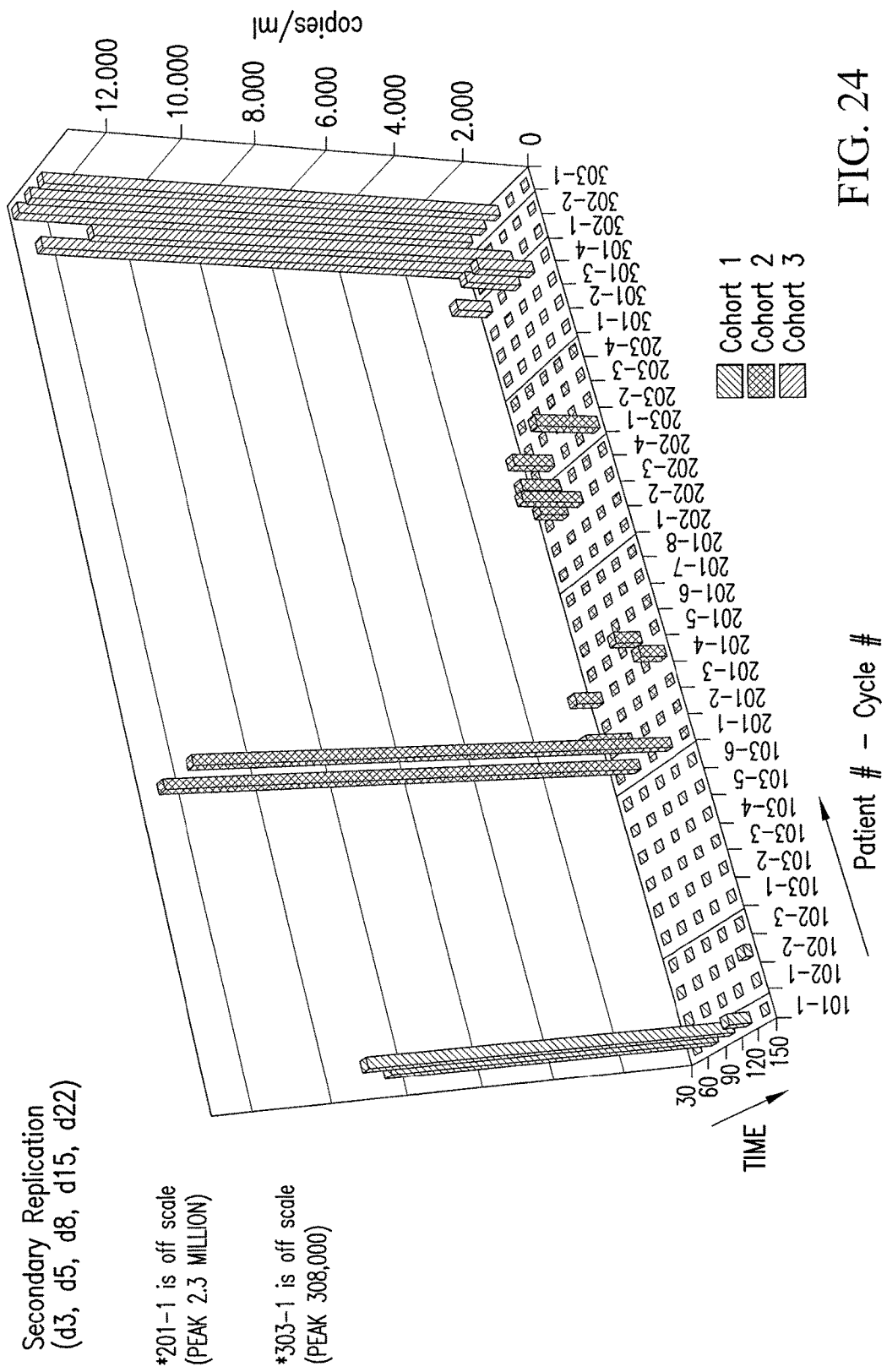
FIG. 24. Replication viremia of JX-594 evident in 80% of patients: Secondary wave of JX-594 in blood cycles 1-7, days 3-22.
Figure 25:
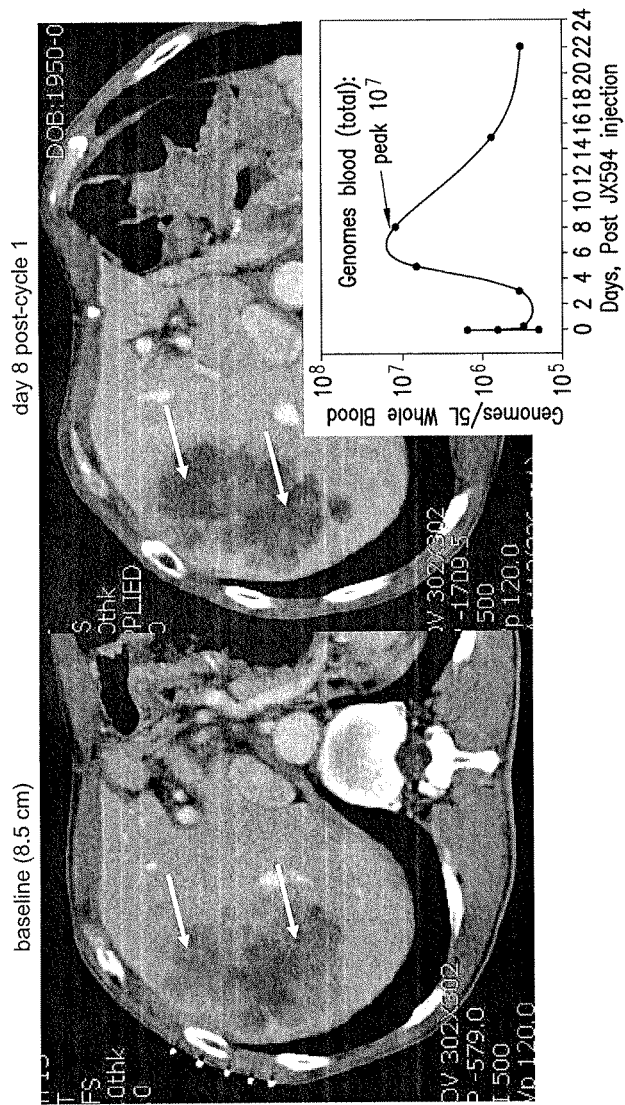
FIG. 25. JX-594 replication-associated vascular shutdown acute treatment-induced avascular necrosis (pt. 1, gastric cancer).
Figure 26:
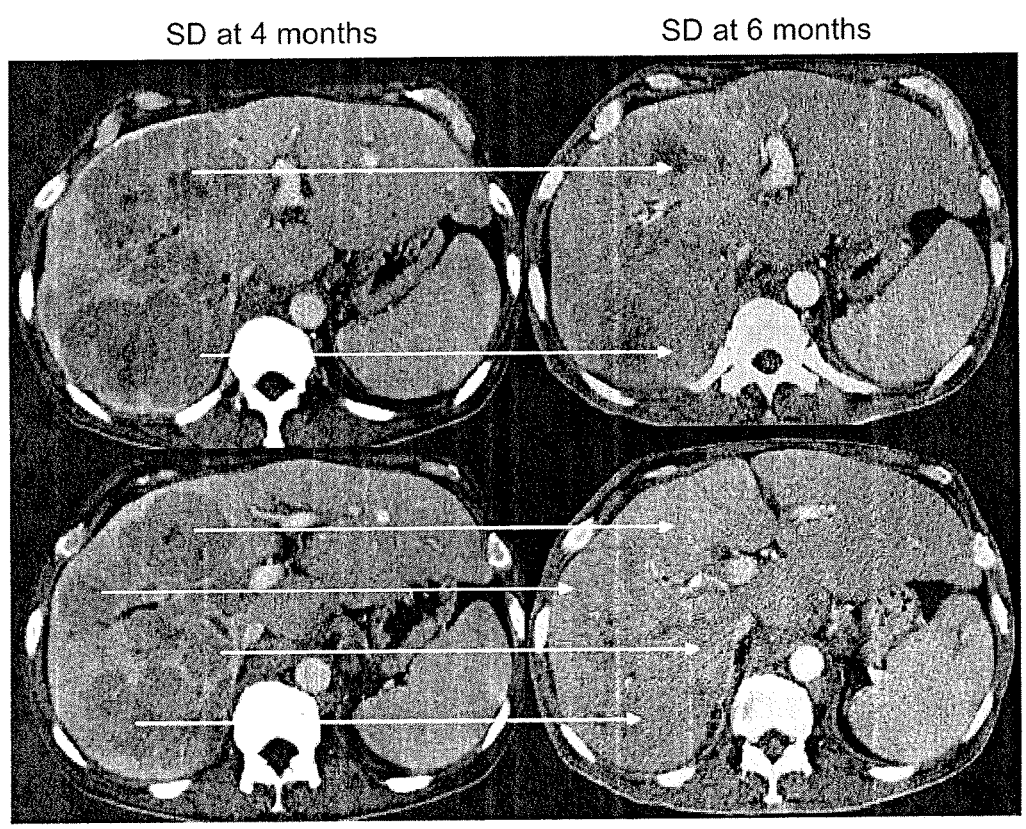
FIG. 26. Long-term Stable Disease with JX-594 squamous cell carcinoma control (lung—cohort 2).
Figure 27:
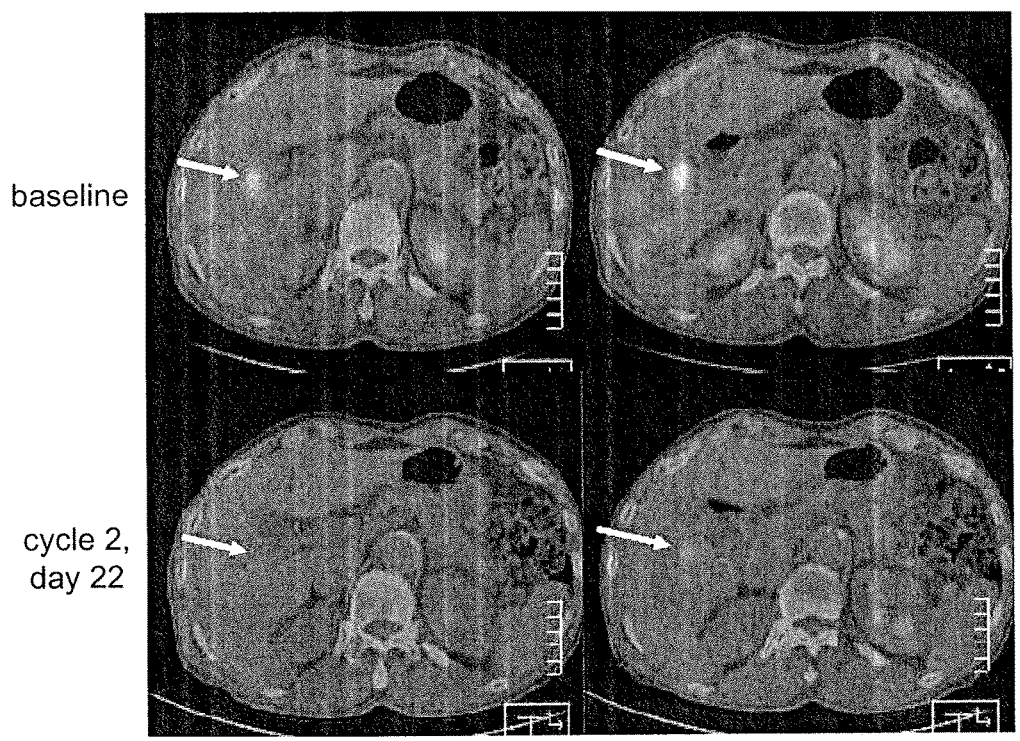
FIG. 27. Metabolic (PET) response JX-594 injected tumor melanoma response after 2 cycles of JX-594 (cohort 3).
Figure 28:
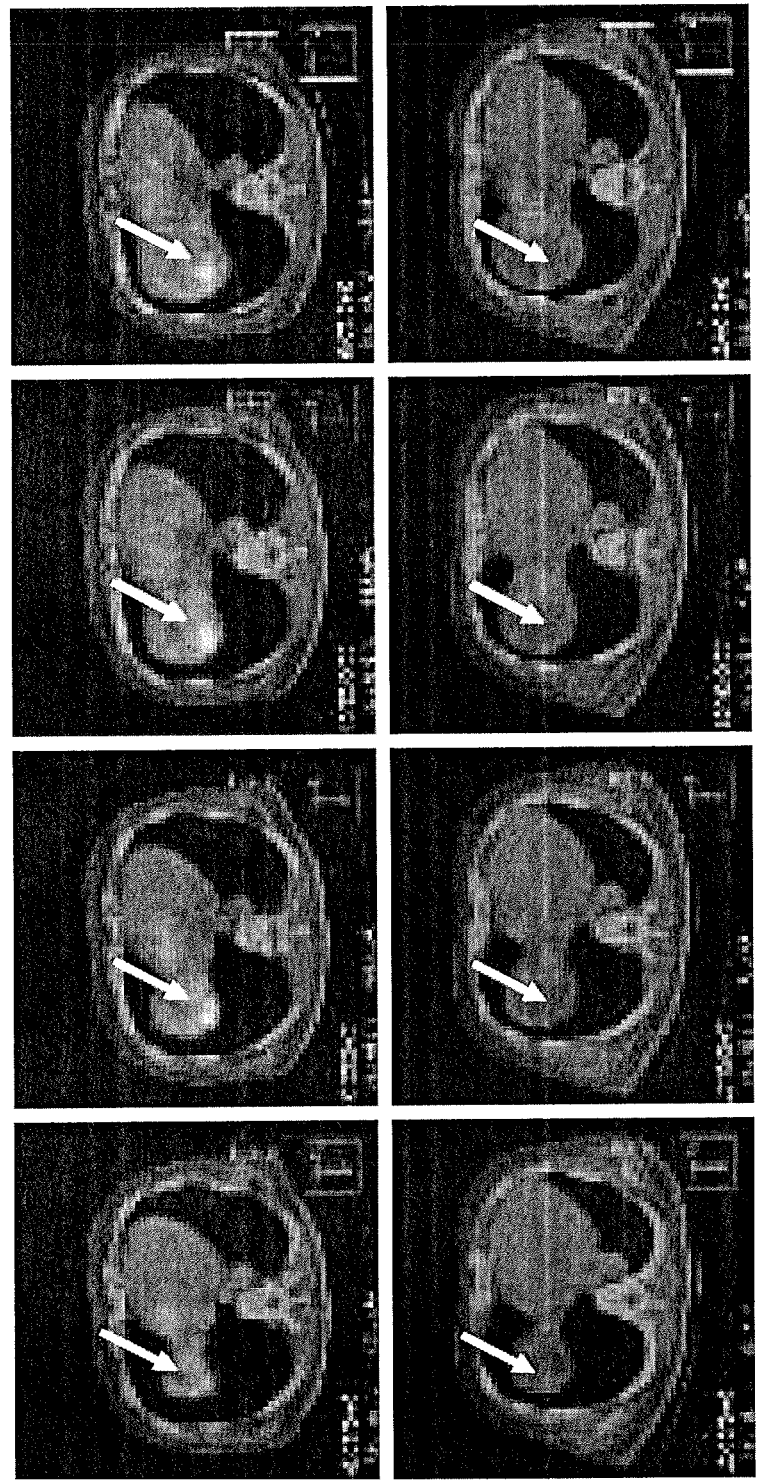
FIG. 28. Metabolic (PET) response JX-594 injected tumor liver carcinoma long-term control (cohort 2) for 9+ months.
Figure 29:
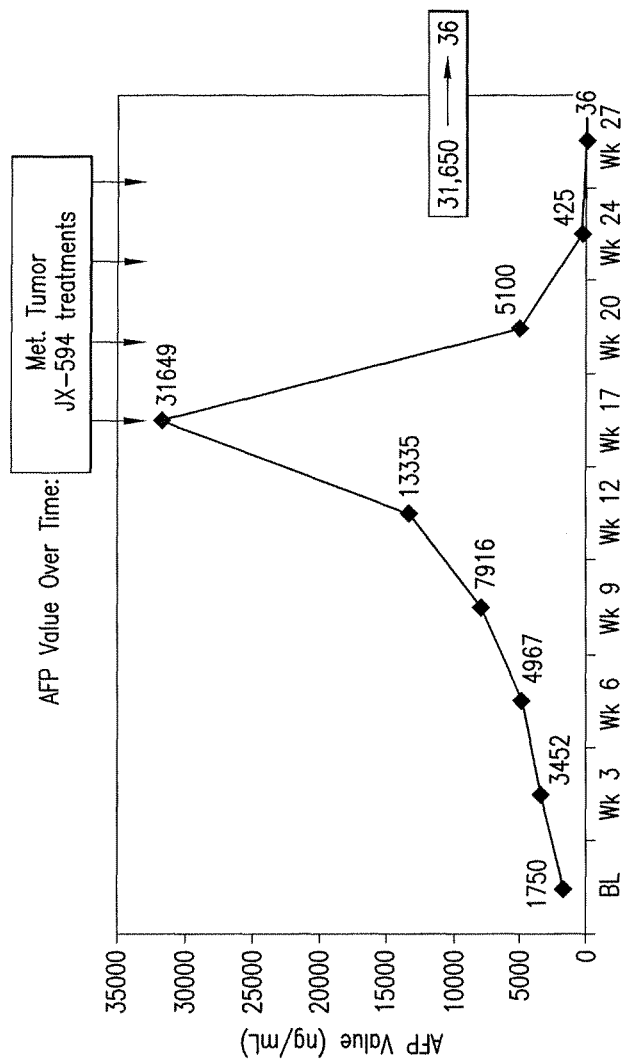
FIG. 29. Tumor Marker Response: 99.9% decrease in AFP Rapid liver cancer destruction demonstrated by blood marker.
Figure 30:
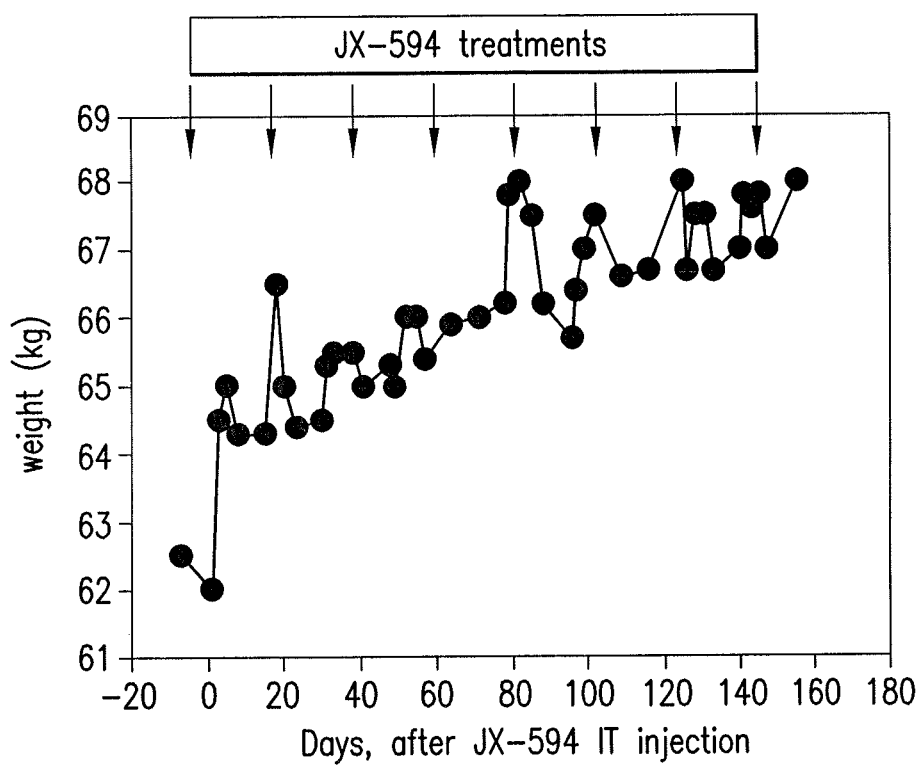
FIG. 30. Body Weight Gain on JX-594 10% increase (6 kg; 14 lb.) demonstrates tolerability, efficacy.
Figure 31:
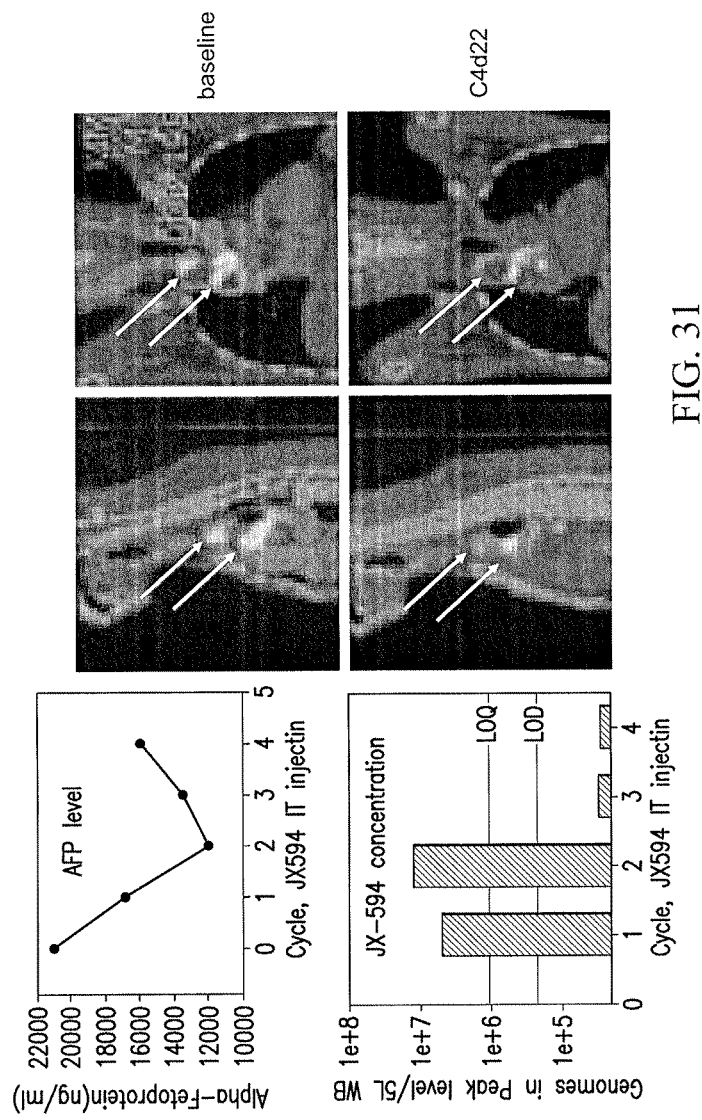
FIG. 31. Systemic viremia and tumor response: JX-594-associated viremia, resultant systemic efficacy (HCC-cohort 2)—AFP decrease 40%.
Figure 32:
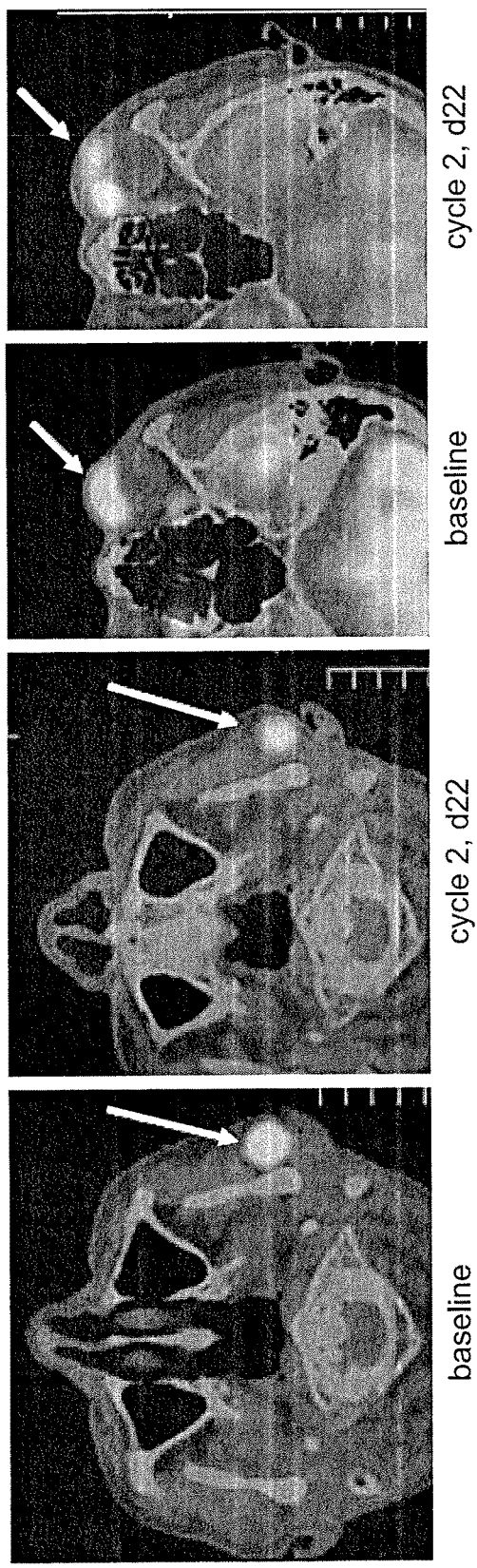
FIG. 32. Systemic JX-594 delivery to tumors and response: Efficacy in non-injected distant tumors after liver met injection. PET metabolic response in two non-injected tumors after 2 cycles (Pt. 304, cohort 3).

One concern in using vaccinia virus as an anti-tumor agent is that, even though systemic delivery to the tumor is initially possible in naïve individuals, the immune response raised by prior exposure to the virus may inhibit the efficacy of subsequent treatment. A strong anti-viral antibody response was raised within 3 weeks of initial infection in the rabbits tested (FIG. 14). To study the feasibility of repeat dosing after neutralizing antibody formation, four rabbits that had initially responded to treatment but had tumor progression after four weeks off of therapy were re-treated. $1\times10^9$ PFU of JX-963 delivered intravenously at 6 weeks after the initial treatment resulted in a decrease in primary tumor size in 3 of 4 animals treated (FIG. 9C).

Therefore, by selecting vaccinia virus, that has evolved to spread through the hematopoietic system, and screening strains for tumor selective replication the inventor was able to find a virus capable of systemic tumor delivery with rapid oncolytic effects. In order to improve the safety of this virus several deletions capable of increasing its therapeutic index were introduced, their mechanism of action described and their biodistribution examined in vivo. Dramatic therapeutic effects against large primary tumors following systemic delivery were demonstrated. Finally, because it is unlikely all tumor cells will be infected, even following systemic viral delivery, GM-CSF was expressed from this viral backbone. The addition of GM-CSF was found to increase the effectiveness of this virus against primary tumors, prevent the outgrowth of micrometastases, and produced an anti-tumor CTL response. This indicates that this virus, JX-963, is capable of systemic delivery to tumors, where it rapidly and efficiently destroys tumor tissue, while sparing normal organs, and at the same time induces an immune response within the tumor that is capable of recognizing tumor antigens produced in situ. Repeat dosing was further shown to produce additional anti-tumor effects, either by direct oncolysis or by boosting the anti-tumor immune response. JX-963 therefore has the potential to effectively treat a variety of tumors.

Example 5

Treatment of Hepatic Carcinoma

A. Objectives (1) To determine the maximally-tolerated dose (MTD) and/or maximum-feasible dose (MFD) of JX-594 administered by intratumoral (IT) injection, (2) To evaluate the safety of JX-594 administered by I.T. injection, (3) To evaluate the replication/pharmacokinetics of JX-594 administered by I.T. injection, (4) To evaluate the immune response to JX-594 and to tumor-associated antigens following I.T. injection (increased inflammatory infiltration at the injected and non-injected sites; neutralizing antibody formation; cytokine responses; and tumor and virus specific Tlymphocytes induction), (5) To evaluate the anti-tumoral efficacy of JX-594 administered by I.T. injection at the injected and non-injected sites B. Study Design This is a Phase I, open-label, dose-escalation study in hepatic carcinoma patients with superficial injectable tumor nodule(s) under imaging guide. Patients who have refractory tumors will receive one treatment of the following four dose levels in a sequential dose escalating design: Cohort 1: $1 \times 10^8$ pfu, Cohort 2: $3 \times 10^8$ pfu, Cohort 3: $1 \times 10^9$ pfu, Cohort 4: $3 \times 10^9$ pfu Target period of such a study will be 15 months. The enrolled patients will receive 1 treatment per cycle. If a patient receives the treatment without a dose-limiting toxicity (DLT) and the target tumor has not progressed, the patient will move on to an additional cycle up to a total of 4 cycles. If a patient has target tumor progressed or is withdrawn from the study due to a DLT or other reasons, the patient will conduct an End of Study Visit and go into the follow-up phase. A cycle is defined as 3 weeks. A DLT will be observed only at the first cycle.

A dose can be distributed into 1-3 lesions. The sum total of the maximal diameters of the lesion(s) to be injected must be less than 10 cm. Three patients will be treated at each dose level unless a DLT is observed. Enrollment will proceed to the next dose level if 0 of 3 patients experiences a DLT; if one of the first 3 patients experiences a DLT, then an additional patient will be enrolled until a second DLT occurs (which is defined as the toxic dose at this time) or until a total of six patients has been treated. If a second DLT doesn't appear in the cohort, the patient advances to the next dose level.

MTD is defined as the dose immediately preceding the dose at which 2 patients experience a DLT after the treatment with JX-594. MFD is defined as the top dose level when MTD is not defined. When MTD/MFD are defined, six additional patients will be treated in order to obtain more data of the safety and toxicity at this dose level. If MTD doesn't occur in Cohort 4 and the efficacy of PR develops in over ⅔ at the previous cohort dose, the clinical study of 6 additional patients will be conducted with this dose.

DLT is defined as any one of the following, attributed to JX-594: 1. Grade 4 toxicity of any period 2. ☐ Grade 3 toxicity (excluding flu-like symptoms: fatigue, nausea, myalgia, fever) lasting >5 days. The National Cancer Institute common Toxicity Criteria of the US will be used to assign the severity of toxicity occurring in this study.

1. Decision on Control Tumor(s) (Non-injected Tumor(s)) (Cycle 1) and JX-594 Injection (Cycle 2+)

During Cycle 1 the investigator will decide control tumor site(s). The control tumor(s) must be a clear tumor nodule located in the lobes other than hepatic lobes of the target tumor(s) and be outside the lymphatic drainage of the target tumor(s). Accordingly, control tumor(s) will be located separately in the left and right lobes of the liver. However, if tumor nodules exist within the limit of one side of the liver, control tumor(s) may be non-injected tumor nodule(s) with JX-594; however a control tumor may not be established if the tumor has an extensive single nodule. This control tumor will be assessed in identical fashion to JX-594 treated tumor(s). This will enable an assessment of the control effect on tumor growth and local toxicity/activity.

If this patient advances to Cycle 2, the control tumor(s) will be injected with JX-594 at the same dose level as the targeted tumor in Cycle 1. As described above, the dose will be distributed among the tumors proportionally based on the tumor size.

2. Non-Target (Non-Injected) Tumor Responders

Non-injected tumors may respond in this study; this phenomenon has been reported in a previous Phase I trial of JX-594 with such patients. It is necessary to understand the mechanism of this effect; possibilities include spread of the virus from the injected tumors and/or induction of tumor-specific cytotoxic (tumor infiltration of T-lymphocytes (CTL) and subsequent cytotoxic T-lymphocytes-mediated tumor destruction). In order to better understand the mechanism(s) of this effect, the investigators will perform the following. If a non-injected tumor(s) responds clinically, core biopsies or fine needle aspirates will be performed at the same collection time points as the injected tumor (See Appendix A; total non-target tumor biopsies do not to exceed two sites). Specimens from non-injected tumors will be analyzed with same method as will be used for materials to be obtained from the injected tumor.

C. Patient Selection

1. Inclusion Criteria

Typically, patients will meet all the following criteria: (1) older than 18 years of age, (2) clinically or histologically confirmed (primary or metastatic) hepatic carcinoma patients with superficial injectable tumor (≤10 cm longest diameter) under imaging guide, which has progressed despite of standard therapies (i.e. refractory to standard therapies), (3) progressed tumor despite of standard treatments such as surgical resection, intraarterial chemoembolization, chemotherapy, and radiation therapy, (4) Patients with Karnofsky Performance Status (KPS) of ≥70, (5) Patients with anticipated survival of at least 16 weeks, (6) If sexually active patients, patients have willingness to use a contraceptive method for 3 months after the treatment with JX-594, (7) Patients with ability to understand and willingness to sign a written informed consent, (8) Patients with ability to comply with the study procedures and follow-up examinations, (9) Patients with adequate bone marrow function: WBC >3,000 cells/mm3, ANC >1,500 cells/mm3, hemoglobin >10 g/dL, and platelet count >75,000 cells/mm3, (10) Patients with adequate renal function: serum creatinine <1.5 mg/dL, (11) Patients with adequate hepatic function: serum AST (≤2.5 of ULN), ALT (≤2.5 of ULN), total bilirubin (≤2.0 mg/dL); for primary lung cancer the patients should be classified to A or B by Child-Pugh classification.

2. Exclusion Criteria

Patients must not meet any of the following exclusion criteria: (1) Pregnant or nursing an infant, (2) HIV patients, (3) Patients classified to C by Child-Pugh classification; patients with total bilirubin >2 mg/dL among patients classified to A or B (in case of primary hepatic cancer), (4) Patients with clinically significant active infection or uncontrolled medical condition (e.g., respiratory, neurological, cardiovascular, gastrointestinal, genitourinary system) considered high risk for new experimental drug treatment, (5) Patients with significant immunodeficiency or family member with the condition due to underlying illness and/or medication taken, (6) Patients with history of eczema requiring systemic therapy, (7) Patients with unstable cardiac disease including MI, unstable angina, congestive heart failure, myocarditis, arrhythmias diagnosed and requiring medication within 6 months prior to patient enrollment of the study, or any other clinically significant condition in cardiac status, (8) Patients who received systemic corticosteroid or any other immunosuppressive medication within 4 weeks prior to study drug treatment, (9) Patients who received any other investigational drug study, radiotherapy, chemotherapy or surgery within 4 weeks prior to patient enrollment of the study, (10) Patients enable or unwilling to give a written informed consent, (11) Patients with hypersensitivity to ingredient(s) of the study drug.

D. Study Visit Procedures

A summary table of the study procedures is presented in the Schedule of Observations and Tests. Usually, +1/−1 day window from the scheduled day may be allowed, and weekends and holidays are not counted.

1. Screening Visit (Day—14 to 0)

This is a clinical study using viruses and the study will proceeded, discussing with the patient. Any patient who wants to take part must provide a written informed consent. After signing an informed consent, each patient will conduct the following assessments within 14 days before the initiation of the study:

Clinical Assessments include (1) A thorough medical and surgical history, including anti-cancer treatments, (2) Weight and vital signs (temperature, pulse rate and blood pressure), (3) Physical examination (whole body systems), (4) Karnofsky Performance Score, (5) Chest x-rays (posterior-anterior and bilateral), (6) 12-lead ECG (acceptable if done within 3 months prior to patient enrollment of the study), (7) Concomitant medication assessment (all medications taken within 14 days prior to patient enrollment of the study).

Laboratory Assessments include (1) Routine blood test (including platelet count and differential counts), (2) Serum chemistries; sodium, potassium, BUN, creatinine, ALT, AST, alkaline phosphatase, total bilirubin, LDH, calcium, phosphorus, magnesium, random glucose, total protein, albumin and uric acid, (3) Coagulation test: prothrombin time (PT), partial thromboplastin time (PTT), and International Normalized Ratio (INR); fibrinogen, (4) HIV, HBV and alpha Fetoprotein test, (5) Neutralizing antibody titer, (6) Viral genomes (Q-PCR), (7) Routine urinalysis (including microscopic examination), (8) Pregnancy test (for women of childbearing potential), (9) Test of appropriate tumor markers (CA125, CEA, AFP, PSA, CA19-9, etc.) at the screening test, depending on the type of tumor; when it is increased, the test will be performed on the 22nd day of each cycle.

Imaging-based Assessments and Measurement of Tumor include measurement of a tumor nodule using abdomen CT scan (Measurement of longest diameter); may be replaced with CT taken on Day 1 (before the treatment). (Acceptable if done within 2 weeks prior to patient enrollment of the study).

Day 1 (Cycle 1-4)—It should be noticed which assessments are to be performed before or after the administration of JX-594.

Day 1; Pre-treatment—Clinical Assessments: Physical examination (whole body systems), Weight and vital signs (temperature, pulse rate and blood pressure), Karnofsky Performance Score, Identification of concurrent therapies, Test and assessment of target tumor(s), Measurement of target tumor(s) (n=1-3); measurement of additional non-injected tumor(s), (n=1-3), Biopsy of target tumor(s).

Laboratory Assessments: Blood—1. Routine blood test (including platelet count and differential counts), 2. Serum chemistry test: sodium, potassium, BUN, creatinine, ALT, AST, alkaline phosphatase, total bilirubin, LDH, calcium, phosphorus, magnesium, random glucose, total protein, albumin and uric acid, 3. Coagulation test: prothrombin time (PT), partial thromboplastin time (PTT), and International Normalized Ratio (INR); fibrinogen, 4. Cytokines (including GM-CSF), 5. Neutralizing antibody titer, 6. Viral genomes (Q-PCR)

Laboratory Assessments: Others—1. Urine test for pfu, 2. Throat swab for pfu

Study Drug Administration—1. Administration of JX-594 as described in Chapter 8

Day 1: Post-treatment—1. Physical examination. Vital signs will be taken twice an hour (30 minutes and 60 minutes) for 6 hours and will be taken routinely later, 2. Blood will be drawn for the cytokine analysis at the following time-points: 1 hour and 3 hours post-treatment, 3. Blood will be drawn for the measurement of circulating JX-594 genomes at the following, time-points: 10-15 minutes, 25-35 minutes and 4-6 hours after the start of administration, 4. Urine and throat swab samples for viral shedding will be taken 3-4 hours post-treatment, 5. Record of side effects and concurrent illnesses Day 3 (Cycle 1-4)—Laboratory Assessments: Blood—1. Routine blood test (including platelet count and differential counts), 2. Serum chemistry test: sodium, potassium, BUN, creatinine, ALT, AST, alkaline phosphatase, total bilirubin, LDH, calcium, phosphorus, magnesium, random glucose, total protein, albumin and uric acid, 3. Coagulation test: prothrombin time (PT), partial thromboplastin time (PTT) and International Normalized Ratio (INR); fibrinogen, 4. Cytokines (including GM-CSF), 5. Neutralizing antibody titer, 6. Viral genomes (Q-PCR).

Laboratory Assessments: Others—1. Urine test for pfu, 2. Throat swab for pfu

Clinical Assessments—Record of side effects and concurrent illnesses

Imaging-based Assessments: abdomen CT scan when suspicious of side effects at clinical Assessments.

Day 5 (Cycle 1-4)—Clinical Assessments—Record of side effects and concurrent illnesses.

Laboratory Assessments: Blood—1. Routine blood test (including platelet count and differential counts), 2. Serum chemistry test: sodium, potassium, BUN, creatinine, ALT, AST, alkaline phosphatase, total bilirubin, LDH, calcium, phosphorus, magnesium, random glucose, total protein, albumin and uric acid, 3. Coagulation test: prothrombin time (PT), partial thromboplastin time (PTT), and International Normalized Ratio (INR); fibrinogen, 4. Viral genomes (Q-PCR).

Day 8 (Cycle 1-4)—Clinical Assessments—Physical examination, CT scan; biopsy of target tumor(s) (Biopsy will also be performed on up to 1 or 2 non-injected tumor(s) which shows a significant change including inflammation, necrosis or shrinkage, etc.). Biopsy will be performed only at Cycle 1 and 2 by the PI's subjective evaluation of the patient condition. Record of side effects and concurrent illnesses.

Laboratory Assessments: Blood—1. Routine blood test (including platelet count and differential counts), 2. Serum chemistry test: sodium, potassium, BUN, creatinine, ALT, AST, alkaline phosphatase, total bilirubin, LDH, calcium, phosphorus, magnesium, random glucose, total protein, albumin and uric acid, 3. Coagulation test: prothrombin time (PT), partial thromboplastin time (PTT) and International Normalized Ratio (INR); fibrinogen, 4. Cytokines (including GM-CSF), 5. Neutralizing antibody titer, 6. Viral genomes (Q-PCR).

Laboratory Assessments: Others—1. Urine test for pfu, 2. Throat swab for pfu 3. Fine needle aspiration of the necrosis when necrosis occurs (performed only at Cycle 1 and 2).

Day 15 (Cycle 1-4)—Clinical Assessments—Physical examination.

Laboratory Assessments: Blood—1. Routine blood test (including platelet count and differential counts) 2. Serum chemistry test: sodium, potassium, BUN, creatinine, ALT, AST, alkaline, phosphatase, total bilirubin, LDH, calcium, phosphorus, magnesium, random glucose, total protein, albumin and uric acid, 3. Coagulation test: prothrombin time (PT), partial thromboplastin time (PTT) and International Normalized Ratio (INR); fibrinogen, 4. Viral genomes (Q-PCR).

Laboratory Assessments: Others—1. Urine test for pfu, 2. Throat swab for pfu

Day 22 (Cycle 1-4)—Clinical Assessments—1. Physical examination, 2. Imaging-based assessments: abdomen CT scan (performed at Cycle 2 and 4 only), 3. Measurement of target tumor(s) (n=1-3); measurement of additional non-injected tumors (n=1-3), 4. Biopsy of target tumor(s) (Biopsy will also be performed on up to 1 or 2 non-injected tumor(s) which show a significant change including inflammation, necrosis or shrinkage.), 5. Record of side effects and concurrent illnesses, 6. Day 22 may be used as Day 1 pre of the following cycle. There may be up to one week interval between Day 22 and Day 1 of the following cycle.

Laboratory Assessments: Blood—1. Routine blood test (including platelet count and differential counts), 2. Serum chemistry test: sodium, potassium, BUN, creatinine, ALT, AST, alkaline phosphatase, total bilirubin, LDH, calcium, phosphorus, magnesium, random glucose, total protein, albumin and uric acid, 3. Coagulation test: prothrombin time (PT), partial thromboplastin time (PTT) and International Normalized Ratio (INR); fibrinogen, 4. Neutralizing antibody, 5. Viral genomes (Q-PCR), 6. Test of appropriate tumor markers (CA125, CEA, AFP, PSA, CA19-9, etc.) at the screening test, depending on the type of tumor; when it is increased, the test will be performed on the $22^{nd}$ day of each cycle.

Laboratory Assessments: Others—1. Urine test for pfu, 2. Throat swab for pfu

Day 28 or End of Study Visit—Clinical Assessments—Physical examination, and Record of side effects and concurrent illnesses.

Laboratory Assessments: Blood—1. Routine blood test (including platelet count and differential counts), 2. Serum chemistry test: sodium, potassium, BUN, creatinine, ALT, AST, alkaline phosphatase, total bilirubin, LDH, calcium, phosphorus, magnesium, random glucose, total protein, albumin and uric acid, 3. Coagulation test: prothrombin time (PT), partial thromboplastin time (PTT) and International Normalized Ratio (INR); fibrinogen, 4. Viral genomes (Q-PCR).

Cycle 3-4—1. A patient whose injection site tumor has not shown >25% increase in longest diameter on Day 22 of Cycle 2 will advance to Cycle 3-4, 2. A patient whose injection site tumor has shown 25-50% increase in longest diameter on Day 22 of Cycle 2 may advance to Cycle 3-4, 3. A patient whose injection site tumor has shown >50% increase in longest diameter on Day 22 of Cycle 2 will be terminated from the study.

Follow-up and Review of Patients—Patients who have completed the clinical study will be followed up in the fashion of routine follow-up for hepatic cancer patients for one year after the End of Study visit. Regardless of the clinical study, patients alive may take routine tests such as hepatoma serum test and imaging-based assessments when they return for a visit to the hospital and take examinations every 3 months. After the completion of the clinical study, if a remarkable clinical benefit is determined, up to total 4 times of additional injection may be administered after obtaining a separate written informed consent. At this time, all procedures of the study will proceed in the same fashion as the first 4 administrations of this study. After the completion of the study up to Cycle 4, until PI judges there is a significant clinical benefit (more than stable disease), up to total 4 times of additional injection of the study drug may be administered. In this case, PI should discuss with the Sponsor in advance and obtain an agreement from the Sponsor. All study plans will proceed in the same fashion as this clinical study.

E. Viral Replication, Spread and Special Tests

1. Q-PCR and Plaque-forming Unit Assays of Plasma and Urine (Pharmacokinetic Test)

Viral spread to the bloodstream will be assessed by quantitative polymerase chain reaction (Q-PCR) test. To detect whether viruses are present in the urine and throat swabs, samples will be collected post-treatment.

2. Tumor Biopsies and Fine Needle Aspirations (Immunity Response Test)

To find out viral replication at the tumor site(s), core biopsies and fine needle aspirations will be conducted (if deemed safe and easy) before and after the treatment. These biopsies will be analyzed for evidence of viral replication, inflammatory and immune cell infiltration, necrosis and apoptosis.

To obtain tissues, core biopsy needle will be used or fine needle aspiration biopsy will be performed under imaging guide. However, sometimes these biopsies may cause an urgency or dangerous situation to the patient. Therefore, when doing a biopsy to obtain tissues, the safety for patient should be the first concern. If a patient's condition is highly likely to get into a danger (hepatic capsular tumor etc.), tissues should be obtained via a safe route.

If the PI judges that tissue biopsy (fine needle aspiration) is likely to cause a danger to the patient, biopsy (fine needle aspiration) may not be carried out. In addition, if needed for the safety of a patient, at the PI's discretion, patients may be hospitalized and observed for up to 5 day before and after administrating a tissue biopsy (fine needle aspiration) and/or intratumoral injection with JX-594.

3. Cytokine Analysis (Immunity Response Test)

Serum concentrations of GM-CSF, IL-1, IL-4, IL-6, IL-10, IFN-δ and TNF-α will be measured with ELISA assay.

4. Neutralizing Antibody Assay (Pharmacokinetic Test)

The occurrence of neutralizing antibody titer of JX-594 in the serially diluted serum of a patient will be identified with a plaque assay.

5. Pharmacokinetic Blood Draws

Pharmacokinetic draw of 3 mL blood each will be taken in a mini yellow top vacutainer.

F. Administration of Investigational Drugs

1. Dose, Administration and Treatment Schedule

Dose. Doses will typically be as follows: Cohort 1: $1\times10^8$ pfu, Cohort 2: $3\times10^8$ pfu, Cohort 3: $1\times10^9$ pfu, Cohort 4: $3\times10^9$ pfu.

Drug Administration. JX-594 can be administered via intratumoral injection. Intratumoral injections will be administered by an expert physician in the manner as described. Using a 21-gauge needle or smaller, tumors will be injected directly with virus-containing solution whose volume is equivalent to approximately 25% of the total volume of tumors (1-3 tumors) to be injected. Typically, injection will be conducted under imaging guide (e.g., under CT). One to three tumors can be injected. Each tumor should receive equal amount of solution. If 2-3 tumors are injected, the volume of virus solution injected into a tumor will be proportional to the volume of the tumor over the others (i.e., if a tumor is twice the volume of the other, the larger tumor will receive ⅔ of the total volume of virus solution).

Although the target tumor(s) selected at Cycle 1 may stop growing, injections should be continued at all cycles. However, if necessary, at Cycle 3 the investigators may additionally select non-target tumors which have not been injected at Cycle 1 and 2, up to three, including the target tumor(s) at Cycle 1. The sum of the maximal diameters of the injected tumors must be ≤10 cm. The dose of intratumorally injected virus solution will be proportional to the volume of the tumor.

JX-594 Preparation. JX-594 is supplied in a frozen (−60° C. or below), single-use glass vial containing 150 μl virus formulation (to deliver 0.1 mL). The volume of 100 μl contains $1.9 \times 10^8$ pfu virus. The vial should be thawed vertically at room temperature. JX-594 should not be placed in a hot water bath. Re-suspend with a pipette. While being diluted and carried to a patient, the virus may be stored at 4° C. Thawed JX-594 should not be injected after 4 hours.

A senior pharmacist and other designated pharmacists should store JX-594 vertically in biological safety cabinets (Class 2) with caution (use of gloves, safety glasses, a gown etc.). Initial procedure for all dilutions: When use a syringe, withdraw required volume of sterile saline solution and transfer to a standardized falcon tube. The final volume of the virus plus diluent for injection should be equivalent to approximately 25% of the target tumor volume.

Cohort 1: One (1) vial of JX-594 will be used to the patients in Cohort 1. The prescribed volume of JX-594 transferred to sterile saline solution will be drawn up with a micropipette/syringe.

Cohort 2: Two (2) vials of JX-594 will be used to the patients in Cohort 2. After mixing, the content in the first vial will be transferred to the second viral. The prescribed volume of JX-594 transferred to sterile saline solution will be drawn up with a micropipette/syringe.

Cohort 3 and 4: Four (4) or eleven (11) vials of JX-594 will be used for administration to the patients in Cohort 3 or 4, respectively. All contents will be transferred to a mixed small polypropylene tube. The prescribed volume of JX-594 transferred to sterile saline solution will be drawn up with a micro-pipette/syringe.

Final procedure for all dilutions: Wrap the tube with aluminum foil or place it in light-proof bag at room temperature. Vortex vigorously for 10 seconds prior to the administration. It should not be injected after 30 minutes exposed at room temperature or after 4 hours thawed.

Treatment Schedule. Typically, enrolled patients receive 1 treatment or dose of JX-594 per cycle. A patient whose JX-594-injected target tumor has not progressed at the end of a cycle will receive the treatment at the subsequent cycle (up to a total of 4 cycles). A patient whose target tumor has progressed will terminate visits. A cycle is defined as 3 weeks. A dose can be divided evenly among 1-3 lesions. The sum of the maximal diameters of the injected lesions must be ≤10 cm.

Dose Escalation. In the dose escalation phase of the clinical study, 2-6 patients will be enrolled per each cohort. If none of the first 3 patients experience a DLT, the study will proceed to the next cohort. If a DLT occurs in one of the first 3 patients in a cohort, the study will proceed until up to a total of 6 patients will be enrolled to the cohort or 2 patients including the first one experience a DLT.

If less than 2 patients out of 6 in Cohort 1 experience a DLT up to 2 weeks following the first injection, the study will advance to the next cohort. If 2 patients experience a DLT, the immediately preceding dose will be defined as the MTD.

Second patient will not enroll until 1 week after administrating the first injection to the first patient at Cycle 1; this rule applies to the next patient's entry. If a DLT occurs in a cohort, all subsequently enrolled patients will start treatment at 2 weeks after completing the first injection at Cycle 1 to all previously enrolled patients. Patients will enter for the cohort of the next dose level at least 2 weeks after the last patient in the previous cohort completes the first injection at Cycle 1.

If more than 2 patients in Cohort 1 experience a DLT, the clinical study will be discontinued.

G. Safety

After treatment, systemic side effects may occur: Fever, chills, myalgia, fatigue/asthenia, nausea, and vomiting. Side effects at the injected tumor site such as pain, necrosis, ulceration and inflammation may occur. In the light of experience on pre-clinical study and GM-CSF clinical study, temporary increase in lymphocyte, monocyte, or white blood cell accompanied with increased neutrophilia may occur. The following may occur at the injected tumor site: Pain, necrosis, ulceration and inflammation.

Although highly unlikely and not described on the previous Phase I trial with JX-594, a disseminated vaccinia-associated rash or encephalitis is theoretically possible; these complications have been described in approximately 1 in 10,000 and 1 in 1,000,000 vaccine recipients, respectively.

1. Dose-Limiting Toxicity (DLT)

DLT is defined as any Grade 3 or more toxicity attributed to JX-594, excluding flu-like symptom(s) (e.g., fatigue, nausea or myalgia), lasting longer than 5 days or any Grade 4 toxicity of any duration attributed to JX-594.

Security of Safety for Patients from Risk of Procedure. Biopsy may cause complications such as intra-peritoneal bleeding and/or shock due to bursting of the tumor. Although the incidence of reported complication is <0.1% and can be cured with transcatheter embolization, the safety for patient should be the first concern. Therefore, if the treating physician judges that a biopsy is likely to cause a danger to the patient, the biopsy may not be carried out. In addition, if needed for the safety of a patient, at the PI's discretion, patients may be hospitalized and observed for up to 5 day before and after undergoing a biopsy and/or intratumoral injection with JX-594.

H. Efficacy

The primary objective of such a study is a Phase I clinical study for safety, not a clinical benefit. Nevertheless, this study is expected to cause shrinkage of the injected and/or non-injected tumor(s) due to direct viral effect (i.e., oncolysis effect) and/or immune-mediated tumor destruction induced by the treatment.

The criterion of efficacy assessment is changes in target lesions. If any changes in non-target lesions, they will be evaluated based on the response of target lesions with reference to the table below.

Evaluation of Target Lesions. Complete Response (CR): Disappearance of all target lesions Partial Response (PR): At least a 30% decrease in the sum of LD of target lesions taking as reference the baseline sum LD. Progressive Disease (PD): At least a 20% increase in the sum of LD of target lesions taking as references the smallest sum LD recorded since the treatment started. Stable Disease (SD): Neither sufficient shrinkage to qualify for PR nor sufficient increase to qualify for PD taking as references the smallest sum LD since the treatment started.

The evaluation criteria of overall response are presented in the following table. The best overall response means the best response recorded from the starting point of the treatment until disease progression/recurrence.

TABLE 3

Evaluation of best overall response

| Target lesions | Non-target lesions | New lesions | Overall response |
|---|---|---|---|
| CR | CR | No | CR |
| CR | Non-CR/Non-PD | No | PR |
| PR | Non-PD | No | PR |
| SD | Non-PD | No | SD |
| PD | Any | Yes or No | PD |
| Any | PD | Yes or No | PD |
| Any | Any | Yes | PD |

CR = Complete Response;
PR = Partial Response;
SD = Stable Disease;
PD = Progression Note: Patients with a global deterioration of health status requiring discontinuation of treatment without objective evidence of disease progression at that time should be classified as having "symptomatic deterioration." Every effort should be made to detect the objective disease progression, even after discontinuation of treatment.

In some circumstances, it may be difficult to distinguish residual disease from normal tissue. When the evaluation of complete response depends on this determination, it is recommended that the residual lesion be investigated (fine-needle aspiration/biopsy) before confirming the complete response status.)

Guideline for Evaluation of Measurable Lesions. All measurements should be taken on the last day of Cycle 2 (Day 22) and the last day of Cycle 4 (Day 22) by CT or MRI and recorded in metric notation by use of a ruler or calipers. All baseline evaluations should be performed as closely as possible to the beginning of treatment and never more than 4 weeks before the beginning of the treatment.

Note: Lesions that have been previously irradiated is not acceptable as measurable lesions. If these lesions are considered acceptable as measurable lesions at the investigator's discretion, condition for consideration of these lesions should be described in the protocol. Also note that tumor lesions that are situated in a previously irradiated area might not be considered measurable. If the investigator considers it is appropriate as measurable lesions, the conditions under which such lesions should be considered must be defined in the protocol.

The same method of assessment and the same technique should be used to characterize each identified and reported lesion at baseline and during follow-up. Imaging based evaluation is preferred to evaluation by clinical examination when both methods have been used to assess the anti-tumor effect of a treatment.

Conventional CT should be performed with contiguous cuts of 10 mm or less in slice thickness. Spiral CT should be performed using a 5 mm contiguous reconstruction algorithm. If applicable, PET-CT may be performed in the screening visit and in this case PET-CT should be used in the assessment on Day 22 of Cycle 2. If necessary, PET-CT may be repeated on Day 22 of Cycle 4.

Confirmation of Measurement/Duration of Response. Confirmation: To be assigned a status of PR or CR, changes in tumor measurements must be confirmed by repeat assessments that should be performed at 8 weeks after the criteria for response are first met. In the case of SD, follow-up measurements of minimum 16-week interval must have met SD criteria at least once after study entry.

Duration of Response: The duration of overall response is defined as the time from date of first documented CR or PR (whichever documented first) to the earliest of date of objectively confirmed recurrence or progressive disease (taking as reference for progressive disease the smallest measurements recorded since the treatment started). The duration of overall complete response is defined as the time from date of first documented CR to the earliest of date of objectively confirmed recurrence.

Duration of Stable Disease: SD is defined as the time from date of first documented SD after the treatment to the earliest of date of objectively confirmed PD (taking the smallest measurements recorded since the treatment started as reference).

Reassessment of Tumor Response. If needed, independent radiologists of this study will assess tumor response. However, the assessments result will be used for the study purpose only and will not affect clinical conclusion.

I. Statistical Methods and Data Analysis

1. Sample Size

The estimated sample size will be 18 patients and the possible range will be 2-30 patients. The primary objectives of the study are to determine the safety and MTD or MFD of JX-594 by intratumoral injection. This study represents the 2nd clinical trial of JX-594 in humans. Because there are not previous clinical studies in human which are based on meaningful statistical calculations, the sample size for this study is selected based upon clinical safety considerations. The results of the study may be used to provide estimates of variability for determining sample size requirements for future clinical studies.

The patients in each cohort have a chance to stop the study before reaching the actual MTD as well as a chance to advance beyond the actual MTD. The tables below show the statistical likelihood of each outcome based on the true DLT incidence. The table below presents the probabilities (various true incidences given to each patient population) of each outcome in a cohort of the first 3 patients.

TABLE 4

| # DLTs in a Cohort of 3 Patients | Action | True Incidence of DLT in Patient Population | | | | |
|---|---|---|---|---|---|---|
| | | 0.1 | 0.2 | 0.3 | 0.4 | 0.5 |
| | | Probability of each outcome | | | | |
| 0 | Advance to next cohort | 0.729 | 0.512 | 0.343 | 0.216 | 0.125 |
| 1 | Enroll additional | 0.243 | 0.384 | 0.441 | 0.432 | 0.375 |

TABLE 4-continued

| # DLTs in a Cohort of 3 Patients | Action | True Incidence of DLT in Patient Population | | | | |
|---|---|---|---|---|---|---|
| | | 0.1 | 0.2 | 0.3 | 0.4 | 0.5 |
| | | Probability of each outcome | | | | |
| ≥2 | 3 patients Stop treatment, define MTD | 0.028 | 0.104 | 0.216 | 0.352 | 0.500 |

The following table shows the probabilities of each outcome in a cohort of 6 patients. After observing 1 DLT in the first 3 patients in the cohort and adding 3 more patients to the cohort, it represents various true incidences in the given patient population.

TABLE 5

| # DLTs in a Cohort of 6 Patients | Action | True Incidence of DLT in Patient Population | | | | |
|---|---|---|---|---|---|---|
| | | 0.1 | 0.2 | 0.3 | 0.4 | 0.5 |
| | | Probability of each outcome | | | | |
| 0 | NA | NA | NA | NA | NA | NA |
| 1 | Enroll additional 3 patients | 0.177 | 0.197 | 0.151 | 0.093 | 0.047 |
| ≥2* | Stop treatment, define MTD | 0.066 | 0.187 | 0.290 | 0.339 | 0.328 |

*1 patient out of the 1st 3 and 1 patient out of the 2nd 3

2. Statistical Methods/Data Analysis

☐The population to be summarized will be an intent-to-treat (ITT) population, defined as all patients to have received at least one treatment with JX-594. In addition, an evaluable patient population will also be assessed as a subset of the ITT population. Evaluable patients are those to have received at least one cycle of therapy with appropriate tumor measurement being performed at a proper time period of the pre- and the post-treatment.

This study will proceed with four treatment cohorts to have two to six patients according to the cohort. The data for each cohort will be summarized with appropriate descriptive statistics, frequency tabulations, graphs, and data listings. The data from the treatment cohorts will be combined for selected data displays. Specific data displays to be generated are described below.

Subject age, weight, and height will be summarized with descriptive statistics (mean, median, standard deviation, minimum and maximum), while gender and race will be summarized with frequency tabulations. The data for the treatment cohorts will be summarized separately for each patient as well as combined. To do this, individual patient listings will be produced. Physical medical history data will be separated for each treatment cohort and will be combined to summarize with frequency tabulations. ☐Treatment administration will be summarized with descriptive statistics (mean, median, standard deviation, minimum and maximum). ☐Any patients who receive the study drug will be included in the safety analysis. Safety data including adverse events, laboratory results, toxicity, vital signs and withdrawal information will be separately summarized at the time of termination of each treatment cohort. ☐AEs will be coded and tabulated using the COSTART body system classification scheme. The number and percent of subjects who have AEs will be tabulated by treatment cohort and treatment purpose; in addition, the data will be stratified by the severity of AE and investigator-specified relationship to JX-594.

Laboratory results will be summarized, at the time of termination, with shift tables displaying the numbers of patients with changes from pre- to post-treatment. Laboratory results of selected variables will be displayed graphically.

In addition to the overall tumor response rates, tumor response rates at the target and nontarget sites will be reported. Time-to-tumor progression at the target and non-target sites will be reported and overall survival will also be reported. ☐As this is an uncontrolled, nonrandomized study with a small number of patients in each group, hypothesis to test data from this study alone is not assumed. In order to assess differences between treatment cohorts, either parametric or nonparametric methods may be used to compare each group, as appropriate.

Example 6

Treatment of Unresectable Malignant Melanoma

A. Dose and Schedule
1. Rationale for Dose and Schedule

A total dose per treatment of $1 \times 10^8$ pfu will be given. This dose is lower than the top weekly dose of $1.6 \times 10^8$ pfu, which was safely administered in the first Phase I study of JX-594 for the treatment of surgically incurable cutaneous melanoma (Mastrangelo et al., 1998). Furthermore, $1 \times 10^8$ pfu is ten times lower than the top dose that has been safely administered to date (n=2 patients) in the ongoing Phase I intratumoral (IT) trial with JX-594 and three times lower than the top dose level cleared to date. In that trial, treatments by IT injection into 1-3 liver tumors are administered every three weeks. Preliminary results from this study reveal that flu-like symptoms and hematology parameters recover to baseline levels typically within 4 days (i.e., Day 5) after treatment with JX-594.

A weekly dosing regimen was chosen because patients in all cohorts recovered from mild to moderate treatment-related toxicities by Day 5 in the ongoing liver IT study described above. Furthermore, data from Mastrangelo et al. 1998 indicate that twice weekly IT injections of up to $8 \times 10^7$ pfu per treatment are safe and effective.

As evidenced by the initial Phase I/II melanoma study (Mastrangelo et al., 1998), patients were found to have developed a significant humoral immune response to vaccinia virus within 14-21 days following re-vaccination. Antibody titers were found to reach a plateau at 4-6 weeks following exposure despite continuing treatments. Therefore, this protocol investigates weekly IT administration for six weeks in order to confer maximum possible delivery and JX-594 anti-tumoral effects prior to the development of high titer antibodies and T cells.

2. Rationale for Study

Melanoma may be the optimal target for JX-594 immunotherapy because of the relatively high rate of accessible disease for injection, the positive response of melanoma seen with IL-2 immunotherapy, and the lack of effective, tolerable therapy for patient with metastatic melanoma. Furthermore, it is contemplated that JX-594 replication targets the EGFR pathway, which is highly expressed in melanocytes.

Results from an initial Phase I/II study suggest that intratumoral injection of JX-594 is safe and effective in treating both injected and distant disease in patients with surgically incurable metastatic melanoma. Response of both injected tumors (in 5 of 7 patients) and response of at least one non-injected tumor (in 4 of 7 patients) was demonstrated, including two patients who achieved a partial response (6+ months) and a complete response (4+ months) to JX-594 treatment. Particularly noteworthy is that efficacy and gene expression occurred despite pre-treatment vaccination (and, therefore, pre-existing anti-vaccinia immunity) in all patients.

This study design was selected in order to expand on the initial Phase I/II study described above and evaluate injected tumor response in up to 15 evaluable patients with Stage 3 or Stage 4 unresectable metastatic melanoma. In addition, JX-594 safety, pharmacokinetics, pharmacodynamics, immune response to JX-594, and expression of the GM-CSF transgene in the blood and tumor tissues will be evaluated. The investigators will also evaluate whether JX-594 is able to spread intravenously and infect non-injected regional and distant disease, suggesting that it may be able to confer similar anti-tumor effects as those experienced at the site of direct intratumoral injection. This finding, in addition to adding to the overall clinical experience of JX-594 administered IT, would strongly support treatment of JX-594 by IV administration for treatment of advanced/metastatic disease, particularly in the treatment of advanced malignant melanoma.

B. Investigational Product Description

JX-594 is a cancer-targeted, replication-selective vaccinia virus derived from the commonly used Wyeth vaccine strain (Dryvax®, Wyeth laboratories). The virus is derived from a vaccine strain with thymidine kinase (TK) gene inactivated. JX-594 contains the gene and promoter for hGM-CSF, a potent cytokine involved in immune response. JX-594 is further modified with the insertion of lacZ gene to allow tracking of the virus in tissues.

C. Objectives

Objective include evaluation of (a) the objective response rate of injected tumor(s), (b) the safety and toxicity of JX-594 administered by IT injection, (c) the objective response rate of entire disease burden after JX-594 administration by IT injection (RECIST criteria), (d) the progression-free survival (PFS) time, and (e) the response rate of non-injected tumor(s).

D. Study Design

1. Study Overview

This is a Phase I/II, open-label trial in patients with unresectable Stage 3 or Stage 4 malignant melanoma. Patients will receive a total of six (6) intratumoral injections with JX-594 over a period of 6 weeks. A total dose of $1 \times 10^8$ plaque-forming units (pfu) will be administered at each treatment and will be divided evenly among up to five (5) tumors. If patients experience a partial injected tumor response to IT treatment with JX-594 after completing 6 treatments, an additional 3 treatments administered weekly may be given.

2. Study Endpoints

Primary endpoints for clinical studies are typically response rate for injected tumor(s), including complete response rate, partial response rate, and duration of response. Secondary endpoints for such studies can include safety, as determined by incidence of treatment-related adverse events, serious adverse events (SAEs), and clinically-significant changes from baseline in routine laboratory parameters including complete response rate, partial response rate, duration of response, Progression-free survival (PFS), Response rate of non-injected tumor(s), including complete response rate, partial response rate, and duration of response. Other endpoints may include overall survival, clinical benefit (including weight gain and improvement in performance status), JX-594 assessment (e.g., viral genome (Q-PCR) in plasma and/or whole blood; Viral infectious virus in plasma and/or whole blood, optional (plaque assay)), Immunologic assessment (JX-594 neutralizing antibodies in serum; plasma GM-CSF measurements (ELISA assay)), histologic assessment (viral gene expression in the tissue; GM-CSF expression; lac-Z expression; inflammatory cell infiltration; necrosis; apoptosis; virus replication factories within the cytoplasm; EGFR pathway status; and tumor thymidine kinase status).

3. Dose

Typically, virus will be diluted in sterile normal saline as described in herein. A total dose of $1 \times 10^8$ plaque-forming units (pfu) will be administered at each treatment and will be divided evenly among up to five (5) tumors.

4. Overall Study Duration and Follow Up

A study period will typically consist of patient visits for screening, study treatment, and post-treatment follow-up evaluations.

Screening. Patient eligibility for a study will be determined within 14 days prior to first treatment with JX-594.

Treatment. Eligible patients will be treated with a dose of $1 \times 10^8$ pfu administered by intratumoral injection weekly (Days 1, 8, 15, 22, 29, and 36) for a total of 6 treatments given over 6 weeks. Patients must continue to meet all eligibility criteria before re-treatment. If a treatment is missed for any reason, the missed treatment will be given the following week provided the eligibility criteria are met, and the visit schedule will be adjusted and patients will be followed accordingly such that the patient receives a total of 6 treatments. Injections may be delayed for a cumulative maximum of 4 weeks. Patients who have delayed treatment will still complete all 6 treatments and will be evaluated for response one week after their 6th treatment. Assessment of response will be initially conducted one week after the final dose is administered (i.e., Day 43). If patients experience a partial injected tumor response to IT treatment with JX-594 after completing 6 treatments, an additional 3 treatments administered weekly may be given.

Post-Treatment Follow-up. All patients will return for a follow-up visit 28 days after last treatment with JX-594 (i.e., Day 64). For 6 months after completion of therapy or until patient has progressive disease at the injection site, begins a new cancer therapy, or dies. The patient will return to the clinic every three weeks after the last injection for tumor measurement by physical exam (PE) (if possible) and evaluation of response. Every 6 weeks, patient will also have a response assessment by PE and/or CT/MRI. After 6 months of follow-up, patient will return to the clinic every 3 months for tumor measurement and response assessments (including CT/MRI) until progressive disease at the injection site, death, or until initiation of new cancer therapy.

Long-Term Follow-up of Gene Therapy Products. After disease progression at the injection site or initiation of new cancer therapy, patient may continue to be monitored for survival and for potential long-term effects of gene therapy according to current FDA guidelines. If patients are no longer returning to the clinic for treatment or post-treatment follow-up, this data may be collected by mail or phone.

E. Study Population

1. Inclusion Criteria

Patients will typically meet all of the following criteria: histologically-confirmed, stage 3 or Stage 4 malignant melanoma; at least one tumor mass measurable by CT/MRI and/or physical examination that can be injected by direct visualization or by ultrasound-guidance; anticipated survival of at least 16 weeks; cancer is not surgically resectable for cure; KPS score of ≥70; age ≥8 years; men and women of reproductive potential must be willing to follow accepted birth control methods during treatment and for 3 months after the last treatment with JX-594; understand and willfully sign an Institutional Review Board (IRB)/Independent Ethics Committee (IEC)-approved written informed consent form; able to comply with study procedures and follow-up examinations; adequate liver function (total bilirubin ≤2.0× ULN; AST, ALT≤2.0×ULN); adequate bone marrow function (WBC >3,500 cells/mm$^3$ and <50,000 cells/mm$^3$; ANC >1,500 cells/mm$^3$, hemoglobin >10 g/dL; platelet count >125,000 plts/mm$^3$); acceptable coagulation status (INR< (ULN+10%)); and acceptable kidney function (serum creatinine <2.0 mg/dL).

2. Exclusion Criteria

Typically, patients should not meet any of the following exclusion criteria: target tumor(s) adherent to and/or invading a major vascular structure (e.g., carotid artery); pregnant or nursing an infant; known infection with HIV; systemic corticosteroid or other immunosuppressive medication use within 4 weeks of first treatment with JX-594; clinically significant active infection or uncontrolled medical condition (e.g., pulmonary, neurological, cardiovascular, gastrointestinal, genitourinary) considered high risk for investigational new drug treatment; significant immunodeficiency due to underlying illness and/or medication (e.g., systemic corticosteroids); history of eczema that at some stage has required systemic therapy; clinically significant and/or rapidly accumulating ascites, peri-cardial and/or pleural effusions (e.g., requiring drainage for symptom control); severe or unstable cardiac disease which includes, but is not limited to, any of the following within 6 months prior to screening: myocardial infarct, unstable angina, congestive heart failure, myocarditis, arrhythmias diagnosed and requiring medication, or any clinically-significant change in cardiac status; treatment of the target tumor(s) with radiotherapy, chemotherapy, surgery, or an investigational drug within 4 weeks of screening (6 weeks in case of mitomycin C or nitrosoureas); experienced a severe reaction or side-effect as a result of a previous smallpox vaccination; inability or unwillingness to give informed consent or comply with the procedures required in this protocol; patients with household contacts who are pregnant or nursing an infant, children <5 years old, have history of eczema that at some stage has required systemic therapy, or have a significant immunodeficiency due to underlying illness (e.g., HIV) and/or medication (e.g., systemic corticosteroids) will be excluded unless alternate living arrangements can be made during the patient's active dosing period and for three weeks following the last dose of study medication.

3. Other Eligibility Criteria Considerations

Deviations to Eligibility Criteria. Patients with minor deviations from the above inclusion/exclusion criteria (e.g., laboratory values outside the pre-specified range) may be allowed into the study if these deviations are not expected to affect the patient's safety, the conduct of the study, or the interpretation of the study results. Written approval by the study sponsor or sponsor's representative for enrollment of patients with minor deviations should be requested.

4. Patient Enrollment Procedures

Once the investigator conducts the screening evaluations and confirms a patient's eligibility, the sponsor typically reviews screening and eligibility information and provides written verification to the investigator for each patient's enrollment. Upon confirming enrollment, the patient will be assigned an identifier using a pre-defined patient numbering scheme. The patient identifier will be a composite of study number, site number, patient number and patient initials.

F. Investigational Product

JX-594 will be supplied by Jennerex Biotherapeutics. Typically, JX-594 is formulated as a liquid and is stored frozen in glass vials designed for single use. Each vial contains 0.15 mL. The virus solution is a colorless to slightly yellow solution that is clear to slightly opalescent. The concentration of JX-594 is 1.9×10$^9$ pfu/mL.

JX-594 is considered a Biosafety Level 2 (BSL-2) infectious substance. The BSL-2 designation and associated guidelines apply to agents of moderate potential hazard to personnel and the environment. Examples of other BSL-2 agents include the measles virus, salmonellae and the Hepatitis B virus. Institutional infection control policies should be consulted.

JX-594 is typically stored in a monitored, secure freezer with restricted access. JX-594 will be stored in clearly-labeled vials within secondary packaging at −60° C. or below with appropriate bio-hazard labeling (indicating the nature of the agent) on the freezer door and the door of the room. Freezers should have an alert limit set at −65° C. to allow time to respond before freezer temperature rises to −60° C. An extended time at >−60° C. will require placing affected material on quarantine until the titer can be reconfirmed.

Worksheets designed to ensure proper handling and preparation of JX-594 will be provided to a study site with supplemental study information. Institutional infection control policies for preparation, transport, and disposal of viral vectors [Biosafety Level 2 (BSL-2)] should be consulted and followed. Gloves, gown and ocular shield should be worn at all times. All work with JX-594 will be carried out in a vertical biological safety cabinet (class 2) in accordance with BSL-2 handling guidelines in a pharmacy/laboratory under the direction of an accredited pharmacist/scientist. The hood itself will be wiped down with 70% ethanol before and after each use.

Thawing. Thawing should occur at room temperature with the vial upright. JX-594 should not be placed in a hot water bath. Once thawed, place the vial in 15 mL polypropylene conical centrifuge tube (e.g., Corning or Falcon), cap the tube, and centrifuge at 100×g for 2 minutes. Remove the vial of JX-594 from the polypropylene tube with forceps or equivalent. Virus formulation must be stored on ice or refrigerated (2-8° C.) until diluted and delivered to patient. Infusion should not begin more than 4 hours after virus formulation has been thawed.

Preparation. After centrifugation of a vial, gently re-suspend with micropipettor (200 μL micropipettor set to 100 μL suggested). Care must be taken not to blow bubbles into the formulation. Approximately 2.75 mL of virus solution (JX-594+saline) is typically prepared, which will be distributed into 5 syringes of 0.5 mL/each. Using a micropipettor, transfer 2.64 mL of sterile normal saline to an appropriately-sized polypropylene tube (e.g., 5 mL Falcon tube). From one (1) vial of JX-594, draw up 116 μL of JX-594 and transfer to the Falcon tube containing the saline. Replace the cap on the Falcon tube, shield the tube from light (with foil or place in light-proof receptacle), and immediately place the covered tube at 2-8° C. (refrigerate or place on wet ice).

Within 30 minutes prior to administration, vortex vigorously for 10 seconds. After vortexing, draw up 0.5 mL of the virus solution (JX-594+saline) into each of 5 syringes. Cap the syringes and deliver to the investigator for injection. Do not begin injection more than 4 hours after virus formulation has been thawed. Virus formulation must be stored on ice or refrigerated (2-8° C.) until diluted and delivered to patient.

1. Administration of JX-594

JX-594 will be administered by intratumoral injection every week for a total of six (6) injections over six weeks. Administration will be done on Days 1, 8, 15, 22, 29, and 36. Patients will receive a dose of $1 \times 10_8$ pfu per treatment divided over ≤5 lesions. Only lesions accessible for treatment via percutaneous injection (e.g., palpable skin nodules or lymph node metastases) or ultrasound (US)-guided injection will be eligible for treatment.

The Investigator will determine at each treatment which lesions (tumors) to inject. Tumors will be injected based on size; the largest lesions should be injected at each treatment. At the investigator's discretion, one or more syringes may be used to treat a tumor.

After aseptic skin preparation at the needle entry site(s), a local anesthetic will be administered. An 18-22 gauge needle will be used for injection. The injection needle will be introduced into the tumor as described below. Injections will be done by the principal investigator or sub-investigator.

Injection into each tumor will be done by injecting the entire syringe volume (0.5 mL) into 4 equally-spaced needle tracts per tumor radiating out from the central puncture site. As an example, the virus injection can be performed as follows: (1) insert the needle (18-22 gauge) into the center of the tumor, (2) extend the needle toward the edge of the tumor (to within 1-3 mm of the edge of the tumor), (3) inject about 25% of the syringe volume (approximately 0.125 mL) while pulling back towards the central puncture site, (4) without withdrawing the needle completely from the tumor, repeat the steps above at spacing of 90° for a total of 4 needle tracks.

Expected Toxicities. The following systemic toxicities are expected following treatment: fever, chills, anorexia, myalgia, fatigue/asthenia and/or headache. Transient decreases are expected in neutrophils, lymphocytes, platelets and hematocrit. Hematologic parameters typically returned to baseline levels by Day 5 (typical duration 2-3 days). For Cycle 1 only, an increase of leukocytes within the first four days following the initial injection is possible. Total white blood cell counts of 24,000/µL and 118,000/µL were reported in two patients in Cohort 3 within 5-8 days post-dose. Increase in eosinophils is also expected post-treatment and typically remains elevated through Day 8. At the injected sites, the following toxicities are likely: pain, necrosis, ulceration and inflammation. At other sites of viral replication (e.g., distant tumors), pain, necrosis, ulceration, and inflammation are possible.

Although highly unlikely and not observed after any treatment or exposure to JX-594, a disseminated vaccinia-associated rash or encephalitis is possible; these complications have been described in approximately 1 in 10,000 and 1 in 1,000,000 smallpox vaccine recipients, respectively. Furthermore, a statistically significant increased risk of myocarditis (1-2 per 10,000 vaccinees) was demonstrated in a recent program of vaccinations with the NYCBOH vaccinia strain (Arness et al., 2004).

G. Statistics

1. Outcome Definitions

Following are definitions of the outcomes relative to the statistical analyses. Toxicity coding and the definitions of progressive disease, complete response, partial response, duration of overall response, evaluable patient, and treatment-related are discussed elsewhere in the protocol.

Progression-Free Survival. Time from first treatment with JX-594 until date of diagnosis of progression, as assessed by the investigator, or the date of death without progression. Patients last known to be alive without progression will be censored at the time of their last assessment of progression. Patients who receive non-protocol therapy prior to the documentation of progressive disease will also be designated as censored in the statistical analyses.

Overall Survival. Time from first treatment with JX-594 until the date of death or date last known to be alive; patients last known to be alive are designated as censored in statistical analyses.

2. Analysis Sets or Populations

All patients who receive JX-594 will be analyzed for demographic characteristics at screening and subsequently for safety, efficacy, pharmacokinetics and pharmacodynamics. The population to be summarized will be an intent-to-treat (ITT) population, defined as all patients receiving at least one treatment with JX-594. In addition, an evaluable patient population will also be assessed (a subset of the ITT population). A patient will be considered an evaluable patient if the patient receives at least one treatment of JX-594 and has appropriate tumor measurement at baseline and at the first appropriate time point post-treatment.

3. Method of Analysis

Continuous variables will be summarized using descriptive statistics (n, mean, standard deviation, median, minimum, and maximum). Categorical variables will be summarized showing the number and percentage (n, %) of patients within each classification. Analyses will be done based on evaluable patients, as well as on the intent-to-treat population. Overall analyses will be conducted; additionally, safety and efficacy analyses will be correlated with disease staging.

Safety: Methods of Analysis. Patients who receive any study medication will be included in the safety analysis. Safety data including adverse events, laboratory results, toxicity, vital signs and withdrawal information will be summarized over time. Patient age, weight, and height will be summarized with descriptive statistics, while gender and race will be summarized with frequency tabulations. Medical history data will be summarized with frequency tabulations.

Adverse events will be coded and tabulated using the MedDRA classification scheme. The incidence of treatment-emergent AEs will be tabulated; in addition, the data will be stratified by adverse event severity (grade) and investigator-specified relationship to JX-594. The analysis of safety will focus on non-hematologic adverse events of Grade 3 or 4 and hematologic adverse events of Grade 4. A listing of SAEs will be produced.

Hematology and serum chemistry results will be summarized using descriptive statistics for continuous variables. In addition, a nadir analysis of selected hematology parameters will be performed and summarized. Laboratory results will be summarized over time in shift tables displaying the numbers of patients with post-dosing changes from baseline relative to the reference range. Laboratory results for selected variables will also be displayed graphically.

KPS performance scores will be summarized using descriptive statistics for categorical variables. The maximum shift in KPS performance scores compared with screening and/or baseline may also be summarized. The remaining safety variables will be summarized using descriptive statistics.

Pharmacokinetic/Pharmacodynamic: Methods of Analysis. Over time, viral replication and shedding into the blood will be assessed by following genome concentrations in the blood. Blood concentrations of JX-594 and GM-CSF levels will be measured in all patients and pharmacokinetic parameters estimated.

The pharmacodynamic parameters to be analyzed will include the effect of JX-594 and GM-CSF on peripheral blood counts, MIA, and tumor biopsy tissue. The immune response to JX-594 following IT injection will be evaluated and summarized, including changes from baseline in white blood cell subsets (absolute eosinophil count, ANC, lymphocytes), cytokines, and formation of neutralizing antibodies to JX-594.

The change from baseline in histologic endpoints (tumor tissue and normal tissue control), including inflammatory cell infiltration, viral gene expression, GM-CSF expression, lac-Z expression and tumor necrosis will be evaluated and summarized. Apoptosis, virus replication factories within the cytoplasm, EGFR pathway status, and tumor thymidine kinase status may also be evaluated.

Efficacy: Methods of Analysis. Treatment response rate based on RECIST criteria will be evaluated for the following: overall response, injected tumor response, and non-injected tumor response. Rates of complete response, partial response, stable disease, and progressive disease will be summarized. Progression-free survival, time-toprogression, duration of response, and overall survival will also be reported. Correlation to disease staging will be assessed.

Progression free survival and duration of response will be estimated using the Kaplan-Meier method. The median, (2-sided) 95% confidence interval for the median, minimum, and maximum duration, as well as the number of censored patients, will be presented. Descriptive statistics and curve for progression-free survival will be made. Assessment of clinical benefit to patients will also be made by evaluation of weight gain and improvement in performance status over time following treatment with JX-594. The change over time in the melanoma inhibitory activity protein (MIA) may be evaluated. MIA may also be compared against treatment response.

Independent Review of Response Assessment. Sites may be asked to provide copies of all radiology data for selected patients (digital or CD-ROM preferred) to an independent radiology reviewer (IRR). For patients with skin lesions, photographs would also be sent to the IRR for independent review. Results from both the site and IRR will be reported. No evaluation of discordance between readers will be conducted.

Example 7

Treatment of Refractory Liver Tumors

In a Phase I pilot trial of JX-594, seven melanoma patients received escalating doses injected into superficial skin metastases (Mastrangelo et al., 1999). No maximum-tolerated dose (MTD) was reported; tumor responses were reported. The objectives of the current trial were to define the following: safety and MTD at significantly higher doses (100-fold), without pre-immunization (as was done in the pilot study), specifically following treatment within a solid organ; pharmacokinetics, including replication-dependent shedding into the blood over three weeks; efficacy against a broad spectrum of cancer types. In this Phase I trial the inventors therefore treated patients with liver tumors (primary or metastatic) by intratumoral injection. For the first time, the inventors report an MTD, plus high-level JX-594 replication and systemic GM-CSF expression, efficacy and distant tumor targeting at well-tolerated doses. The results reported herein support future i.t. and i.v. trials with JX-594 and products from this class.

A. Materials and Methods

1. Study Design

The primary objective was to determine the safety and MTD of JX-594. Secondary objectives included pharmacokinetics, replication and shedding (urine, throat swabs), immune responses (neutralizing antibodies, cytokines) and tumor responses. Patients received one of four dose levels ($10^8$, $3\times10^8$, $10^9$, $3\times10^9$ plaque-forming units, pfu) in a group-sequential dose escalation design (2-6 patients per dose level). The MTD was defined as the dose level immediately preceding that for which two or more dose-limiting toxicities (DLT) were observed. DLT was defined as any grade 4 toxicity, or grade 3 toxicity lasting $\geq 5$ days. An independent Data Safety Monitoring Board (DSMB) reviewed all dose-escalation decisions and major safety assessments.

2. Patient Selection

Patients signed informed consent, according to Good Clinical Practice (GCP) guidelines. Inclusion criteria included unresectable, injectable solid tumor(s) within the liver that had progressed despite treatment with standard therapies, normal hematopoietic function (leukocyte count >3,000 $mm^3$, hemoglobin >10 g/dL, platelet count >75,000/$mm^3$ and organ function (including creatinine $\leq 1.5$ mg/dL, AST/ALT$\leq 2\cdot 5$ of ULN, Child-Pugh class A or B), life expectancy $\geq 16$ weeks, and Karnofsky Performance Status (KPS)$\geq 70$. Exclusion criteria included increased risk for vaccination complications (e.g., immunosuppression, eczema), treatment with immunosuppressive or cancer treatment agents within 4 weeks, pregnancy, or nursing.

3. Manufacturing and Preparation of JX-594

JX-594 is a Wyeth strain vaccinia modified by insertion of the human GM-CSF and lacZ genes into the TK gene region under control of the synthetic early-late promoter and p7•5 promoter, respectively. Clinical trial material was generated according to GMP guidelines in Vero cells and purified through sucrose gradient centrifugation. The genome-to-pfu ratio was approximately 70:1. JX-594 was formulated in phosphate-buffered saline with 10% glycerol, 138 mM sodium chloride at pH 7•4. Final product QC release tests included assays for sterility, endotoxin and potency. JX-594 was diluted in 0.9% normal saline in a volume equivalent to 25% of the estimated total volume of target tumor(s).

4. Treatment Procedure

JX-594 was administered via imaging-guided intratumoral injection using 21-gauge PEIT (percutaneous ethanol injection, multi-pore; HAKKO Medicals; Tokyo, Japan) needles. Tumors (n=1-3) were injected every three weeks along two needle tracks during withdrawal of the needle through the tumor. The initial treatment course was 2 cycles; up to 6 additional cycles were allowed if tumor response occurred.

5. Patient Monitoring

Patients were monitored as described in Table 6. Patients were monitored after treatment in the hospital for at least 48 hours, and for four weeks as out-patients.

TABLE 6

Study Procedures

| Study Day | Day -14~0 | Day 1 Pre | Day 1 Post | Day 3 | Day 5 | Day 8 | Day 15 | Day 22[7] | End of Study Visit/Day 28 |
|---|---|---|---|---|---|---|---|---|---|
| JX-594 injection (under CT-guidance) | | | x | | | | | | |
| *Clinical Evaluations* | | | | | | | | | |
| Physical exam, ECOG performance status | x | x | x[1] | x | x | x | x | x | x |
| *Safety Laboratory Evaluations[2]* | | | | | | | | | |
| Hematology[3]/Coagulation | x | x | | x | x | x | x | x | x |
| Serum Chemistries | x | x | | x | x | x | x | x | x |
| *Viral Assays* | | | | | | | | | |
| Plasma/blood levels of JX-594: Q-PCR | | x | x[4] | x | x | x | x | x | x |
| Shedding (throat swab, urine): plaque assay | | x | x[4] | x | | x | x | x | |
| *Immunologic Evaluations* | | | | | | | | | |
| Neutralizing antibodies | | x | | | | | | x | |
| Cytokines (inc. GM-CSF) | | x | x[5] | x | | x | | | |
| *Pathologic Evaluations* | | | | | | | | | |
| Tumor biopsy | | x[6] | | | | x[6] | | x[6] | |
| *Efficacy Evaluations* | | | | | | | | | |
| CT scan | x | | | | | | | x | |
| PET-CT (optional) | | | | | | | | | |
| Serum tumor markers[8] | x | | | | | | | x | |

6. Neutralizing Antibody (NAb) Titers

NAb titers were determined by cytopathic effect inhibition assay. Heat-inactivated serum was serially diluted in media using half log dilutions. 50 μL samples were incubated with 1,000 pfu JX-594 for two hours, then inoculated onto A2780 cells. After 3 days, cell viability was determined using Cell Counting Kit-8 (Donjindo Laboratories, Kumamoto, Japan). NAb titer was defined as the reciprocal of the highest dilution of serum that resulted in ≥50% cell viability.

7. Quantitative PCR for JX-594

Quantitative PCR (Q-PCR) was used to measure JX-594 genomes in blood serially due to its reproducibility and ability to detect product regardless of antibody and/or complement neutralization. JX-594 DNA was purified from samples using the QIAamp DNA Blood Mini Kit (Qiagen GmbH, Hilden, Germany). Q-PCR was run as described previously (Kulesh et al., 2004). The lower limits of JX-594 detection and quantitation were 666 and 3,333 copies/mL plasma, respectively.

8. JX-594 Shedding Detection

A plaque-forming assay was used to detect any shedding of infectious JX-594 into the environment; infectious unit shedding would have public health relevance. Urine and saliva samples were spun, resuspended in 10 mM Tris (pH 9•0), and titered on A2780 cells by plaque assays. The detection limit was 20 pfu/ml sample.

9. Cytokine Assays

GM-CSF was detected by ELISA kit (BioSource International; Carlsbad, Calif., USA) following the instructions of the vendor. Serum levels of IL-1β, IL-6, IL-10, TNF-alpha, and interferon-gamma were assessed using the LIN-COplex kit as instructed by the manufacturer (LINCO; St. Charles, Mo.).

10. Histopathology Staining for Vaccinia Proteins and LacZ in Blood and Tumor Samples Formalin-fixed, paraffin-embedded biopsies were stained with hematoxylin and eosin for histology. For immunohistochemistry, mouse monoclonal antibodies for B5R (Vac-14, α-B5R, 46 μg/mL; Dr. Gary Cohen, University Pennsylvania; diluted 1:50 or 1:100) were used, followed by incubation with DAKO EnVision+™ anti-mouse HRP-labeled polymer (DAKO, Carpinteria, Calif.) prior to development using DAB (Kirkegaard & Perry Laboratories; Gaithersburg, Md.). For LacZ staining, cells were spun at 900 rpm for 1 minute, rinsed, and fixed with 0.5% gluteraldehyde on glass slides. Cells were then washed and stained with X-gal solution for 4 hours to overnight.

11. Tumor Response Assessment

Tumor response was assessed after every two cycles. Contrast-enhanced CT scanning was standard (unless contraindicated). Maximum tumor diameters and Hounsfield units (HU; density estimate) were obtained. RECIST and Choi criteria for response were applied (Choi et al., 2007). Tumor markers were followed if elevated at baseline.

12. Statistical Issues

Study sample size was determined by safety issues. The intent-to-treat population (≥1 dose) and standard dose-escalation design were utilized. The likelihood of dose escalation, given varying true DLT rates in the treated population, was calculated as per routine in Phase I dose-escalation trials.

B. Results

1. Patient Characteristics

Figure 34:
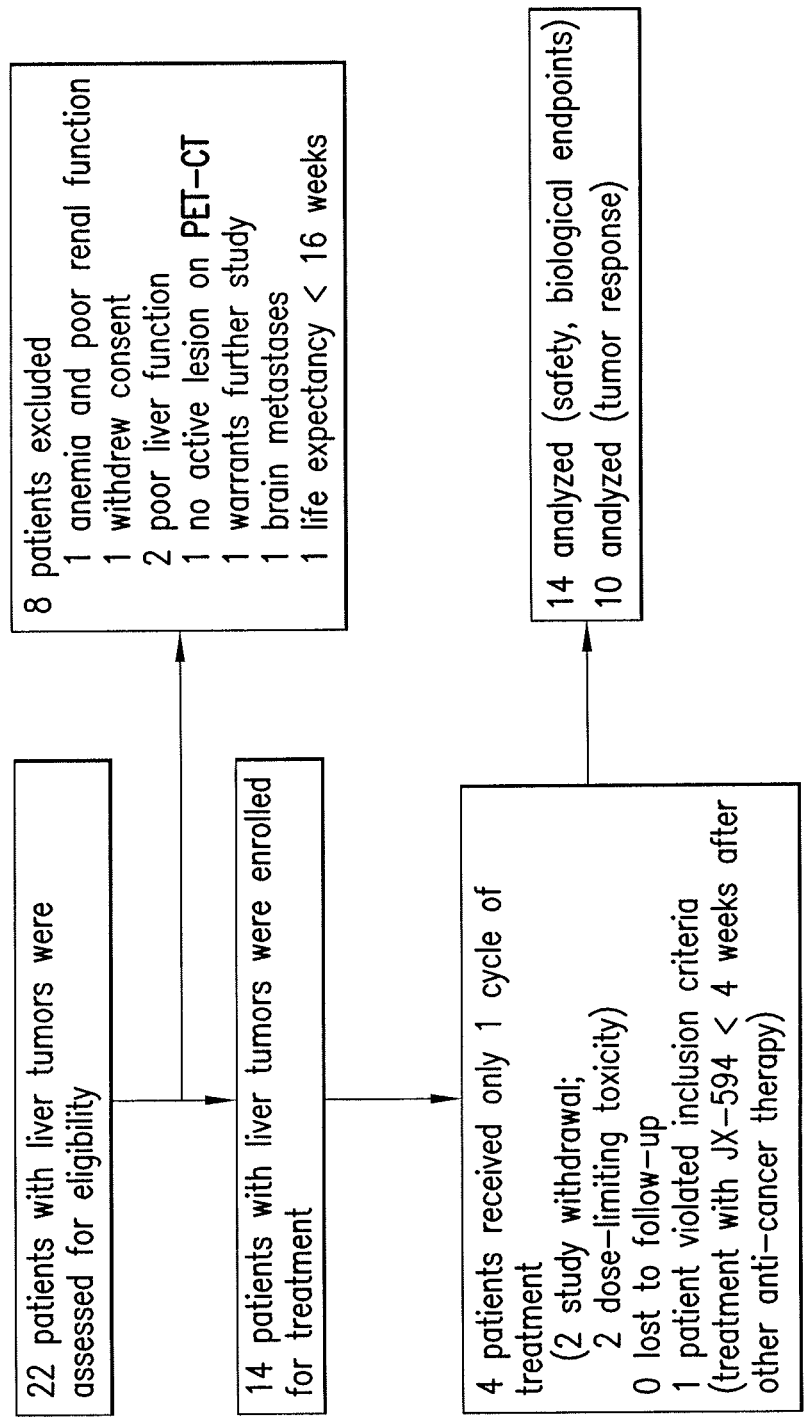
FIG. 34. Trial profile.

Fourteen patients were enrolled (characteristics listed in Table 7; trial profile in FIG. 34). Three patients were treated in cohorts 1-2, six in the third and two in the highest. Six patients were treated in cohort 3 at the request of the DSMB due to an unrelated patient death attributed to tumor progression. Two patients (cohorts 1, 3) had treatment suspended after one cycle due to unrelated adverse events, and patients at the highest dose received one cycle due to DLT (see below).

TABLE 7

Patient demographics

| | |
|---|---|
| Mean Age (years) | 56.5 (37-66) |
| Sex | 11 males, 3 females |
| Mean previous therapies | 5.6 (2-12) |
| Tumor size (cm) | 6.9 (3.5-9.8) |
| Cycles of JX-594 received | 3.4 (1-8) |
| Tumor types | Colon (4), HCC (3), melanoma (2), RCC (1), SCC-thymic (1), SCC-lung (1), gastric (1), extragonadal germ cell (1) | b. Laboratory Data

Figure 35A:
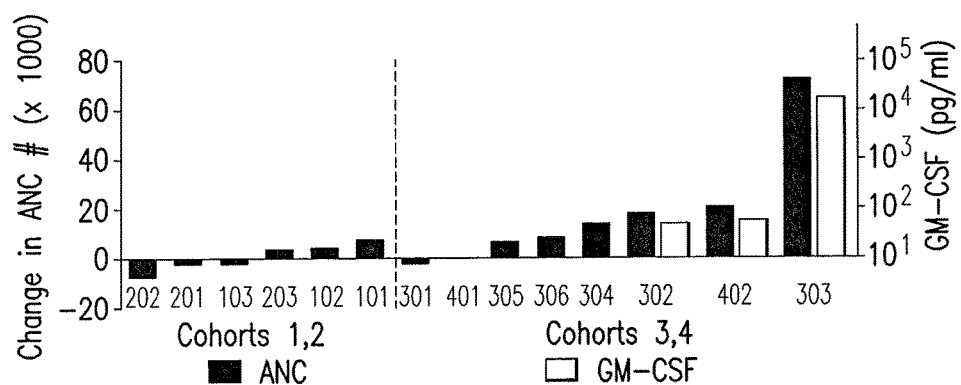
FIGS. 35A-35B. Key hematologic tests and liver function tests (error bars, standard error of mean). (A) Increase in ANC correlates with increased JX-594 dose and expression of hGM-CSF. Filled bars: ANC; open bars: GM-CSF. X-axis: patient identification number. (B) ALT levels of patients in cohorts 3 and 4 in the first cycle. The majority of patients experienced no significant changes in ALT levels over time; mild, transient transaminitis was also observed.
Figure 35B:
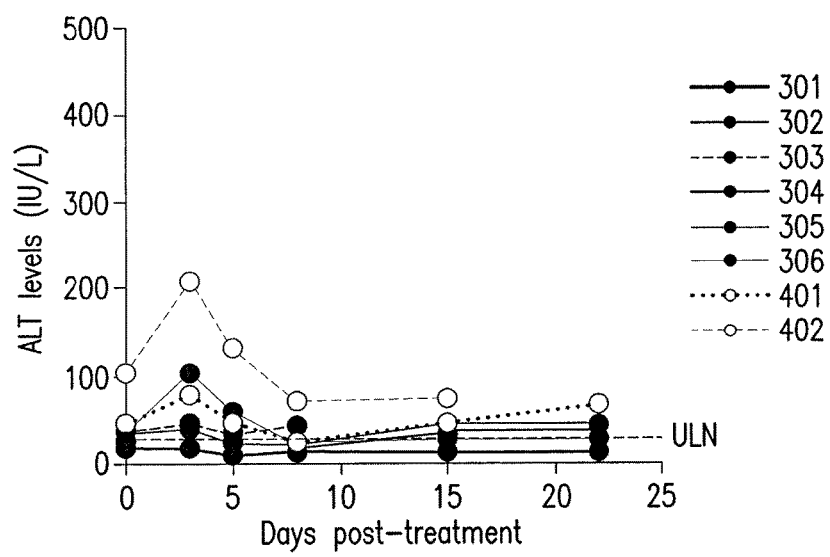

Treatment-related transient decreases in lymphocytes, platelets and hematocrit were noted during the first 3 days. Nine patients had a significant increase in absolute neutrophil counts (ANC) within the first four days (seven increased >100%; FIG. 35A). ANC increases were dose-related and frequently associated with GM-CSF detection in the blood. ANC increased significantly ($\geq 5,000/\mu L$) in 75% of patients in cohorts 3 and 4 (versus 17% in cohorts 1, 2; FIG. 35A); increases in monocytes and eosinophils were observed. Thrombocytopenia was also dose-dependent (FIG. 36A) but cycle-independent (FIG. 36B). ANC increases were greatest in cycle 1 (FIG. 36C). Lymphopenia and leukopenia occurred in 2 patients (Table 8). Significant transaminitis did not occur at the MTD (FIG. 35B).

TABLE 8

Most Common Adverse Events (including Grade 1/2 AEs Experienced by $\geq 3$ Patients and Grade 3/4 AEs Experienced by $\geq 1$ Patient) possibly related to JX-594

| | | Number of Patients by Cohort | | | | | | | | | | | |
|---|---|---|---|---|---|---|---|---|---|---|---|---|---|
| | | Grade 1/2 | | | | Grade 3 | | | | Grade 4 (5) | | | |
| Body System | Event | 1 (n = 3) | 2 (n = 3) | 3 (n = 6) | 4 (n = 2) | 1 (n = 3) | 2 (n = 3) | 3 (n = 6) | 4 (n = 2) | 1 (n = 3) | 2 (n = 3) | 3 (n = 6) | 4 (n = 2) | Total Patients (n = 14) |
| General | Fever | 3 | 3 | 5 | 2 | | | 1 | | | | | | (14) 100% |
| | Chills | 3 | 2 | 6 | 2 | | 1 | | | | | | | (14) 100% |
| | Fatigue | | 2 | 3 | 1 | | | | | | | | | (6) 43% |
| Gastrointestinal | Anorexia | 2 | 2 | 5 | | | | | 1 | | | | | (10) 71% |
| | Nausea | 1 | 1 | 1 | | | | | | | | | | (3) 21% |
| Nervous System | Headache | 1 | 1 | 2 | | | | | | | | | | (4) 29% |
| Metabolic/ Laboratory | Hyponatremia | | | | | | | 2 | | | | | | (2) 14% |
| | Alk Phos increased | | | | | | 1 | 1 | | | | | | (2) 14% |
| | Hyperbilirubinemia | | | | | 1 | | | 2 | | | | | (3) 21% |
| | ALT increased | | | | | 1 | | 1 | | | | | | (2) 14% |
| | AST increased | | | | | 1 | | | 1 | | | | | (2) 14% |
| | Hypophosphatemia | | | | | | | 1 | | | | | | (1) 7% |
| | Fibrinogen decrease | 1 | 1 | | | | | | | | | | | (2) 14% |
| Hematologic | Leukocyte count increased | | | 2 | 1 | | | 1 | | | | | | (4) 29% |
| | Platelet count decreased | | | 1 | | | 2 | | | | | | | (3) 21% |
| | Leukopenia | | 1 | 1 | | | 1 | | | | | | | (3) 21% |
| | Neutrophil count decreased | | | | | | | 2 | | | | | | (2) 14% |
| Pain | Pain - general | 1 | 1 | 2 | | | | | | | | | | (4) 29% |

2. Treatment-related Toxicity a. Adverse Events (AE)

JX-594 was well-tolerated up to the MTD ($10^9$ pfu). No treatment-related deaths occurred on study. All patients experienced grade 1-2 flu-like symptoms (from 4-16 hours post-treatment). Dose-related hypotension (grade 2, no organ dysfunction) occurred within 4-12 hours. Table 8 lists the most common AEs possibly related to JX-594. Only one serious AE case (anorexia and abdominal pain) was deemed treatment-related. Ten serious and unrelated (according to the PI) AEs were reported and attributed to tumor progression-associated complications. Four patients died from tumor progression during the AE reporting period.

Two patients in cohort 4 experienced DLTs. Both experienced Grade 3 direct hyperbilirubinemia due to tumor swelling and obstruction of the intrahepatic bile duct, plus Grade III anorexia and abdominal pain.

3. Pharmacokinetic and Pharmacodynamic Endpoints a. Serum GM-CSF

Thirteen patients were negative for serum GM-CSF at baseline. Three patients at the MTD had detectable GM-CSF >48 hours (46-16,000 pg/mL) after JX-594 injection (FIG. 35A), concentrations that were higher than those reported following subcutaneous injection of GM-CSF protein in patients (Cebon et al., 1992). GM-CSF concentrations correlated with WBC induction (FIG. 35A).

b. Neutralizing Antibodies (NAb)

Low (<10) or undetectable anti-JX-594 antibody (NAb) levels were noted at baseline in 79% of patients. All patients developed NAb within 22 days. NAb titers peaked after the first dose in 45% of patients, and increased further in 55%.

Figure 38A:
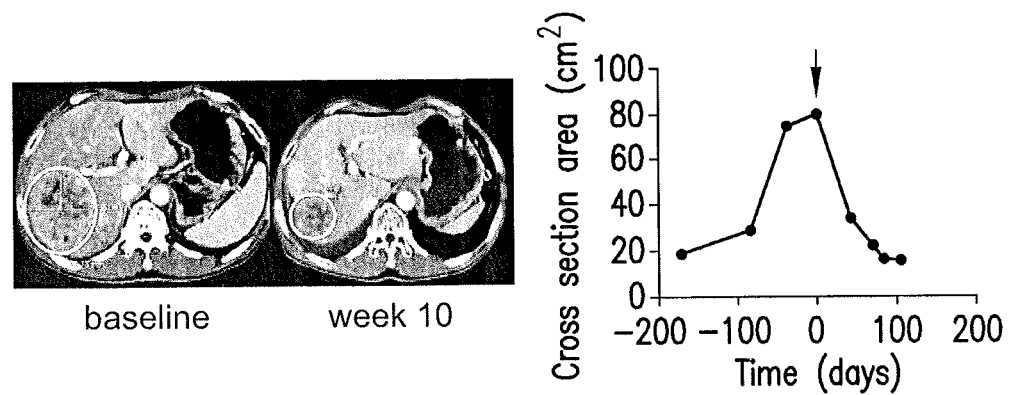
FIGS. 38A-38B. Antitumoral efficacy. (A) Representative CT scans and tumor measurements of a non-small cell lung cancer target tumor. circles: tumors. Arrow: time when JX-594 administration was initiated. Note the changes in the cross sectional area of the tumor over time. (B) Representative physical, CT and PET-CT scan results demonstrating objective tumor response (after 4 cycles) of metastatic tumor in neck, injected after induction of high titer neutralizing antibodies to JX-594.
Figure 38B:
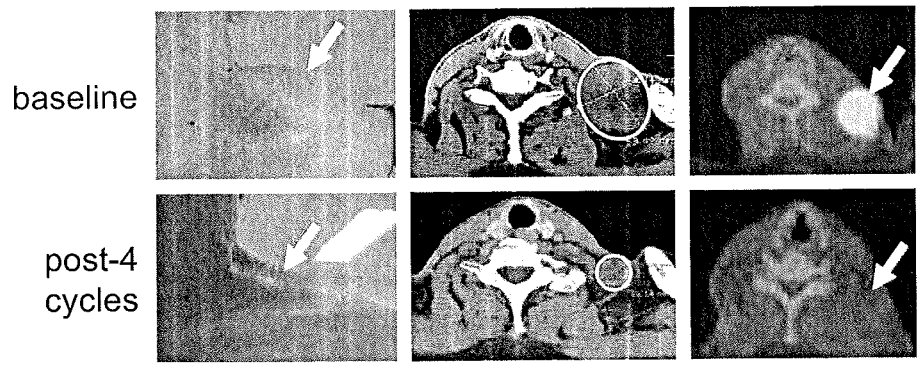

No correlation was seen between baseline or post-treatment NAb titers and any clinical or laboratory endpoint, including JX-594 pharmacokinetics, replication, GM-CSF expression or efficacy. Three patients with objective RECIST tumor responses had detectable baseline NAb titers and high titers post-treatment (32,000, 32,000, and 10,000). In addition, two patients had newly developed neck metastases treated after high-level NAb induction, and both tumors underwent objective responses (below; Table 9 and FIG. 38B).

e. JX-594 Dissemination, Replication within Non-Injected Distant Tumor Sites

Figure 37B:
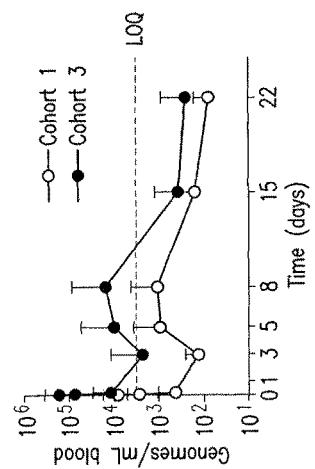
FIGS. 37A-37F. Pharmacokinetics, blood-borne spread and distant tumor infection by JX-594. (A) Acute genome concentrations in circulation. JX-594 genomes were detected as early as 15 minutes post-injection. For cohorts 1 to 3, the acute clearance rates were consistent between cohorts. (B) JX-594 genome concentrations of cohorts 1 and 3 in cycle 1 are shown. Concentrations of JX-594 genomes, including levels of secondary viremia peaks, were dose-related. LOQ: limit of quantitation. Error bars represent standard error of the mean. (C) Representative JX-594 genome concentrations in cycle 1. (D) JX-594 recovery and hGM-CSF expression from a melanoma patient (cohort 3). High levels of JX-594 genomes and GM-CSF were detected in circulation as well as malignant body fluids (cohort 3, melanoma patient). Asterisk: undetectable; PE: pleural effusion. (E) Infectious JX-594 presence was demonstrated by lac-Z expression (blue) from cells in a malignant pleural effusion. (F) Biopsy sample from non-injected liver cancer metastasis (neck) showing vaccinia virus B5R staining (arrows; brown).
Figure 37D:
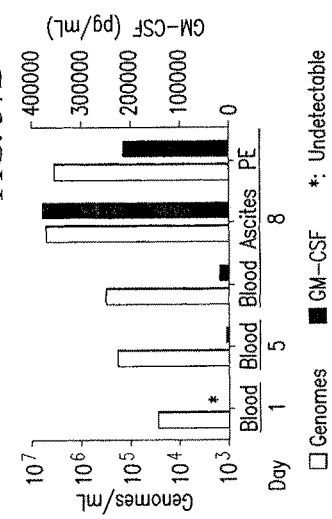
Figure 37A:
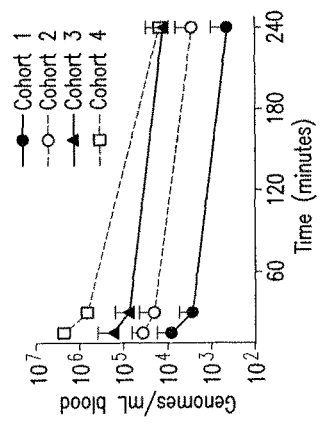
Figure 37C:
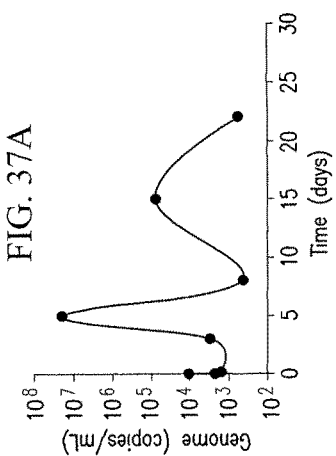
Figure 37E:
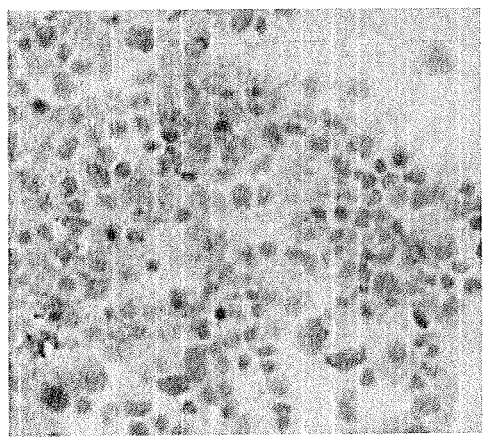
Figure 37F:
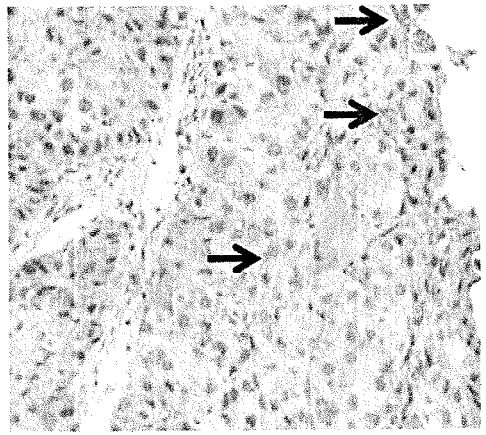

JX-594 was detected in non-injected tumor tissues, indicating distant tumor-selective infection and replication (FIG. 37D-F). For example, the malignant ascites and pleural

TABLE 9

Target tumor responses and survival duration

| Patient (tumor type/diameter/previous treatments) | Cohort/ cycles | RECIST[2] | Choi[3] | PET | Tumor Marker[4] | Survival[5] |
|---|---|---|---|---|---|---|
| 103 (SCC lung/9.8 cm/5) | 1/6 | PR | + (↓51% diam) | n.a. | n.a. | 19 · 8 m[6] |
| 201 (HCC/6.2 cm/5) | 2/8 | Liver: PR Neck: PR | + (↓30% diam) + (↓57% diam) | Liver: neg Neck: −76% | PR (−98%) | 11 + m |
| 304 (Melanoma/7.8 cm/3) | 3/6 | Liver: PR Neck: SD | + (↓33% diam) + (↓51% HU) | Liver: −29% Neck: −42% | n.a. | 12 · 2 + m |
| 301 (RCC/5.7 cm/5) | 3/4 | SD | + (↓42% HU[7]) | +40% | n.a. | 15 · 1 m[6] |
| 302 (Colon/9.0 cm/6) | 3/4 | SD | + (↓15% HU) | +4% | SD | 8 · 9 m |
| 202 (SCC thymic/9.7 cm/4) | 2/4 | SD | + (↓16% HU) | n.a. | n.a. | 10 · 1 m |
| 102 (Colon/4.1 cm/4) | 1/3 | SD | + (↓31% HU) | n.a. | n.a. | 8 · 2 m |
| 203 (Extragonadal germ/ 6.1 cm/4) | 2/5 | SD | + (↓40% HU) | −6% | SD | 4 · 5 m |
| 305 (Colon/7.4 cm/5) | 3/2 | SD | − (↑28%) | +55% | PD | 1 · 8 m |
| 306 (Colon/5.8 cm/11) | 3/2 | PD | + (↓33% HU) | +56% | SD | 9 · 4 m[6] |
| 101 Gastric/8.5 cm/6) | 1/1 | n.a.[8] | n.a.[8] | n.a. | n.a. | 1 · 8 m |
| 303 (Melanoma/10.9 cm/7) | 3/1 | n.a. | n.a. | n.a. | n.a. | 10 d |
| 401 (HCC/3.5 cm/12) | 4/1 | n.a. | n.a. | −41% | PR (−81%) | 3 + m |
| 402 (HCC/9.8 cm/2) | 4/1 | n.a. | n.a. | n.a. | PR (−65%) | 18 + d |

[1]First number reflects dose level (eg. 103 was in dose level 1)
[2]RECIST criteria: partial response (PR) is a maximum diameter decrease of ≥30%; progressive disease (PD) is an increase of ≥20%; stable disease is a change in diameter between these two bounds for PR and PD
[3]Choi criteria: maximum diameter decrease of ≥10% or density decrease of ≥15%; + indicates response
[4]Tumor marker response definition: ≥50% decrease: PR; ≥25% increase: PD; <50% decrease or 25% increase: SD; marker was alpha-fetoprotein (AFP) in patients 201, 301, 402; PIVKA2 for 401; carcinoembryonic antigen (CEA) for 302, 305, 306.
[5]Survival: + indicates no cancer-related death; m: months; d: days
[6]still alive
[7]HU: Hounsfield units
[8]CT scans performed at week 3 showed tumor progression c. Cytokines Interleukin-6, IL-10, and TNF-α peaked at 3 hours. Later peaks (day 3-22) were also observed. Cytokine induction was greater in cycles 2-8 than in cycle 1. Interleukin-6 induction correlated with GM-CSF in serum. IL-1β and IL-4 induction were not noted.

d. JX-594 Pharmacokinetics

All patients had JX-594 genomes detected immediately after injection (49 of 50 cycles). Concentrations correlated with dose (FIGS. 37A and 37B), decreasing ~50% within 15 minutes and ~90% within 4-6 hours. Initial clearance rates were not dose-dependent nor antibody titer-dependent. Following initial release and clearance of injected JX-594 in blood, delayed re-emergence of circulating JX-594 was frequently detected, consistent with replication. Twelve of 15 (80%) patients had detectable genomes (blood or plasma) between days 3-22. Secondary peak concentrations generally correlated with dose, and the pharmacokinetics were similar (FIG. 37B). Lower secondary concentration peaks were detected after repeat dosing in cycles 2-7 (4 of 11 patients). Representative pharmacokinetics are shown in FIG. 37C.

effusion of one patient had higher genome concentrations (17-and 12-fold higher, respectively) and GM-CSF concentrations (24-and 13-fold higher, respectively) than in blood at the same timepoint (FIG. 37D). LacZ(+) cells in the pleural effusion confirmed JX-594 infection (FIG. 37E). Another patient had a distant neck tumor biopsied and replicating JX-594 was demonstrated histologically (FIG. 37F).

f. JX-594 Shedding

No infectious JX-594 was detected in any throat or urine sample.

4. Antitumoral Efficacy of JX-594

Ten patients were evaluable for target tumor responses; non-evaluable patients had contraindications to contrast (2) or no post-treatment scans (2). Nine (90%) had either objective response (30%) or stable disease (60%) by CT RECIST criteria. Eight (80%) had objective responses by Choi criteria (Table 9). Patients with response by both RECIST and Choi criteria had non-small cell lung cancer (FIG. 38A), HCC and melanoma (Table 9). Objective responses were durable; regrowth at responding tumor sites did not occur (4-18 months follow-up). Direct injection of previously non-injected tumors in the neck in two patients, after 4 prior cycles in the liver, led to Choi and/or RECIST responses despite high-level neutralizing antibodies to JX-594 (Table 9, FIG. 38B); therefore, re-treatment efficacy was feasible.

Responses in distant, non-injected tumors were also assessed. Among seven patients with distant non-injected tumors, six patients had stable distant disease by RECIST criteria; the time-to-progression of these distant tumors ranged from 6+ to 30+ weeks. Three of these patients had responses by Choi criteria (n=2) or PET-CT (n=1; 25-100% decrease; Table 10).

TABLE 10

Responses of distant tumors in patients with target tumor control (RECIST PR or SD)

| Patient (dose gp[1]) | Distant tumor size (cm)/location | RECIST | Choi | PET | Time to tumor progression[2] |
|---|---|---|---|---|---|
| 202 | 5.9/Liver | SD | + (↓35% HU) | n.a. | 30+ wks |
| 103 | 8.5/Liver | SD | + (↓22% HU) | n.a. | 7+ wks |
| 304 | 7/face, mediastinum | n.a. | n.a. | CR - SC tumor PR - PA tumor | 6+ wks |
| 102 | 4.3/Liver | SD | − (↓10% HU) | n.a. | 9 wks |
| 203 | 8.3/LNs | SD | − (↑5%) | −6% (12 wks) | 15 wks |
| 201 | 3.7/Liver | SD | − (↓6%) | SD | 18 wks |
| 301 | 11.8/Liver | PD | − (↑22%) | +10% | 6 wks |

[1]First number reflects dose level (e.g. 103 was in dose level 1)
[2]by CT RECIST;
+indicates no cancer-related death
HU: Hounsfield units;
LN: lymph nodes;
SC: supraclavicular;
PA: preauricular;
CR: complete response;
PR: partial response;
SD: stable disease;
PD: progressive disease To date, eight patients (57%) have survived for at least 8 months, four more than one year and one up to 20+ months. Median survival was 9 months.

* * *

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 4,554,101
U.S. Pat. No. 4,683,202
U.S. Pat. No. 4,684,611
U.S. Pat. No. 4,952,500
U.S. Pat. No. 5,073,627
U.S. Pat. No. 5,302,523
U.S. Pat. No. 5,322,783
U.S. Pat. No. 5,384,253
U.S. Pat. No. 5,399,363
U.S. Pat. No. 5,464,765
U.S. Pat. No. 5,466,468
U.S. Pat. No. 5,538,877
U.S. Pat. No. 5,538,880
U.S. Pat. No. 5,543,158
U.S. Pat. No. 5,550,318
U.S. Pat. No. 5,563,055
U.S. Pat. No. 5,580,859
U.S. Pat. No. 5,589,466
U.S. Pat. No. 5,591,616
U.S. Pat. No. 5,610,042
U.S. Pat. No. 5,633,016
U.S. Pat. No. 5,641,515
U.S. Pat. No. 5,656,610
U.S. Pat. No. 5,702,932
U.S. Pat. No. 5,736,524
U.S. Pat. No. 5,739,169
U.S. Pat. No. 5,780,448
U.S. Pat. No. 5,789,215
U.S. Pat. No. 5,798,339
U.S. Pat. No. 5,801,005
U.S. Pat. No. 5,824,311
U.S. Pat. No. 5,824,348
U.S. Pat. No. 5,830,880
U.S. Pat. No. 5,846,225
U.S. Pat. No. 5,846,233
U.S. Pat. No. 5,846,945
U.S. Pat. No. 5,925,565
U.S. Pat. No. 5,928,906
U.S. Pat. No. 5,935,819
U.S. Pat. No. 5,945,100
U.S. Pat. No. 5,981,274
U.S. Pat. No. 5,994,624

Alcami and Smith, *Cell.*, 71(1):153-167, 1992.
Alcami et al., *J. Gen. Virol.*, 80:949-959, 1999.
Alcami et al., *Sem. Virol.*, 5:419-427, 1998.
Alcami et al., *Virology*, 74(23):11230-11239, 2000.
Almendro et al., *J. Immunol.*, 157(12):5411-5421, 1996.
Arap et al., *Cancer Res.*, 55(6):1351-1354, 1995.
Arness et al., *Am. Epidemiol.*, 160:642-51, 2004.
Austin-Ward and Villaseca, *Revista Medica de Chile*, 126 (7):838-845, 1998.
Ausubel et al., In: *Current Protocols in Molecular Biology*, John, Wiley & Sons, Inc, NY, 16.15.1-16.18.10, 1996.
Bajorin et al., *J. Clin. Oncol.*, 6(5):786-792, 1988.
Bakhshi et al., *Cell*, 41(3):899-906, 1985.
Blasco and Moss, *J. Virology*, 66(7): 4170-4179, 1992.
Blasco et al., *J. Virology*, 67(6):3319-3325, 1993.
Boyd et al., *Cell*, 79:341-351, 1994.
Brizel, *Semin. Radiat. Oncol.*, 8(4):237-246, 1998.
Bukowski et al., *Clinical Cancer Res.*, 4(10):2337-2347, 1998.
Caldas et al., *Cancer Res.*, 54:3568-3573, 1994.
Carbonelli et al., *FEMS Microbiol. Lett.*, 177(1):75-82, 1999.
Cebon et al., *Br. Haematol.*, 80(2):144-150, 1992.
Chandler et al., *Proc. Natl. Acad. Sci. USA*, 94(8):3596-601, 1997.
Chen and Okayama, *Mol. Cell Biol.*, 7(8):2745-2752, 1987.
Cheng et al., *Cancer Res.*, 54(21):5547-5551, 1994.
Choi et al., *J. Clin. Oncol.*, 25(13):1753-1759, 2007.
Christodoulides et al., *Microbiology*, 144(Pt 11):3027-3037, 1998.
Cleary and Sklar, *Proc. Natl. Acad. Sci. USA*, 82(21):7439-7443, 1985.
Cleary et al., *J. Exp. Med.*, 164(1):315-320, 1986.
Cocea, *Biotechniques*, 23(5):814-816, 1997.
Colamonici et al., *J. Biol. Chem.*, 270:15974-15978, 1995.
Culver et al., *Science*, 256(5063):1550-1552, 1992.
Curran, *Seminars Radiation Oncol.*, 8(4Suppl):2-4, 1998.
Davidson et al., *J. Immunother.*, 21(5):389-398, 1998.
Dillman, *Cancer Biother. Radiopharm.*, 14(1):5-10, 1999.
Dobbelstein and Shenk, *J. Virology*, 70:6479-6485, 1996.
Durrant and Spendlove, *Curr. Opin. Investig. Drugs*, 2(7): 959-66, 2001.
Eliopoulos et al., *Oncogene*, 11(7):1217-28, 1995.
Erlandsson, *Cancer Genet. Cytogenet.*, 104(1):1-18, 1998.
Fechheimer et al., *Proc Natl. Acad. Sci. USA*, 84:8463-8467, 1987.
Fraley et al., *Proc. Natl. Acad. Sci. USA*, 76:3348-3352, 1979.
GenBank Accession Number NC001559
Gnant et al., *Ann Surg*, 230(3):352-360, 1999.
Gnant et al., *Cancer Res.*, 59(14):3396-403, 1999.
Gnant et al., *J. Natl. Cancer Inst.*, 91(20):1744-1750, 1999.
Goebel et al., *Virology*, 179(1):247-266, 517-563, 1990.
Gopal, *Mol. Cell Biol.*, 5:1188-1190, 1985.
Graham and Van Der Eb, *Virology*, 52:456-467, 1973.
Graham et al., *Virology*, 229(1):12-24, 1997.
Gross et al., *Genes Dev.*, 13(15):1899-911, 1999.
Gross et al., *J. Biol. Chem.*, 274:1156-1163, 1999.
Hanibuchi et al., *Int. J. Cancer*, 78(4):480-485, 1998.
Harland and Weintraub, *J. Cell Biol.*, 101(3):1094-1099, 1985.
Heise et al., *Cancer Gene Ther.*, 6(6):499-504, 1999.
Heise et al., *Cancer Res.*, 59(11):2623-2628, 1999.
Hellstrand et al., *Acta Oncologica*, 37(4):347-353, 1998.
Hermiston, *J. Clin. Invest.*, 105:1169-1172, 2000.
Ho et al., *J. Biol. Chem.*, 27:7765-7769, 1998.
Homey et al., *Nature. Rev. Immunol.*, 2:175-184, 2002.
Hui and Hashimoto, *Infection Immun.*, 66(11):5329-5336, 1998.
Hussussian et al., *Nat. Genet.*, 8(1):15-21, 1994.
Ikeda et al., *Nat. Med.*, 5(8):881-7, 1999.
Inouye and Inouye, *Nucleic Acids Res.*, 13:3101-3109, 1985.
Irie and Morton, *Proc. Natl. Acad. Sci. USA*, 83(22):8694-8698, 1986.
Irie et al., *Lancet.*, 1(8641):786-787, 1989.
Isaacs et al., *Proc. Natl. Acad. Sci. USA*, 89(2):628-32, 1992.
Johnson and Hamdy, *Oncol. Rep.*, 5(3):553-557, 1998.
Ju et al., *Gene Ther.*, 7(19):1672-1679, 2000.
Ju et al., *J. Neuropathol. Exp. Neurol.*, 59(3):241-250, 2000.
Kaeppler et al., *Plant Cell Reports*, 9:415-418, 1990.
Kamb et al., *Nat. Genet.*, 8(1):23-26, 1994.
Kamb et al., *Science*, 2674:436-440, 1994.
Kaneda et al., *Science*, 243:375-378, 1989.
Kato et al, *J. Biol. Chem.*, 266:3361-3364, 1991.
Kay et al., *Proc. Natl. Acad. Sci. USA*, 94(9):4686-4691, 1997.
Kerr et al., *Br. J. Cancer*, 26(4):239-257, 1972.
Kettle et al., *J. Gen. Virology*, 78:677-685, 1997.
Kim et al., *Nat. Med.*, 7:781-787, 2001.
Kolmel, *J. Neurooncol.*, 38(2-3):121-125, 1998.
Kraus et al. *FEBS Lett.*, 428(3):165-170, 1998.
Kulesh et al., *J. Clin. Microbiol.*, 42(2):601-609, 2004.
Kyte and Doolittle, *J. Mol. Biol.*, 157(1):105-132, 1982.
Lareyre et al., *J. Biol. Chem.*, 274(12):8282-8290, 1999.
Lee et al., *Biochem. Biophys. Res. Commun.*, 238(2):462-467, 1997.
Levenson et al., *Hum. Gene Ther.*, 9(8):1233-1236, 1998.
Liebermann, *Oncogene*, 17(10):1189-94, 1998.
Macejak and Sarnow, *Nature*, 353:90-94, 1991.
Magi-Galluzzi et al., *Anal. Quant. Cytol. Histol.*, 20(5):343-350, 1998.
Mangray and King, *Front Biosci.*, 3:D1148-1160, 1998.
Marsters et al., *Recent Prog. Horm. Res.*, 54:225-234, 1999.
Mastrangelo et al., *Cancer Gene Ther.*, 6(5):409-422, 1999.
Mastrangelo et al., *Cancer Treat Res.*, 94:35-50, 1998.
Mayer et al., *Radiat. Oncol. Investig.*, 6(6):281-288, 1998.
McCart et al., *Gene Ther.*, 7(14):1217-23, 2000.
Mitchell et al., *Ann. NY Acad. Sci.*, 690:153-166, 1993.
Mitchell et al., *J. Clin. Oncol.*, 8(5):856-869, 1990.
Mori et al., *Cancer Res.*, 54(13):3396-3397, 1994.
Morton et al., *Arch. Surg.*, 127:392-399, 1992.
Moss, In: *Fields Virology.*, Fields (Ed.), Lippincott-Raven Publishers: Philadelphia, 2637-2672, 1996.
Mossman et al., *Virology*, 215(1):17-30, 1996.
Mougin et al., *Ann. Biol. Clin.*, (Paris) 56(1): 21-8, 1998.
Mumby and Walter, *Cell Regul.*, 2(8):589-98, 1991.
Natoli et al., *Biochem. Pharmacol.*, 56(8):915-20, 1998.
Nicolau and Sene Nobori et al., 1994
Nomoto et al., *Gene*, 236(2):259-271, 1999.
Ochi et al., *Am. J. Gastroenterol.*, 93(8):1366-1368, 1998.
Ohara, *Gan To Kagaku Ryoho*, 25(6): 823-828, 1998.
Okamoto et al., *Proc. Natl. Acad. Sci. USA*, 91(23):11045-11049, 1994.
Omirulleh et al., *Plant Mol. Biol.*, 21(3):415-428, 1993.
Orlow et al., *Cancer Res*, 54(11):2848-2851, 1994.
PCT Appln. WO 94/09699
PCT Appln. WO 95/06128
Pelletier and Sonenberg, *Nature*, 334(6180):320-325, 1988.
Pietras et al., *Oncogene*, 17(17):2235-2249, 1998.
Puhlmann et al., *Cancer Gene Ther.*, 7:66-73, 2000.
Qin et al., *Proc. Natl. Acad. Sci. USA*, 95(24):14411-14416, 1998.
Ravindranath and Morton, *Intern. Rev. Immunol.*, 7: 303-329, 1991.

Remington's Pharmaceutical Sciences" 15$^{th}$ Ed., 1035-1038 and 1570-1580, 1990.
Rippe, et al., *Mol. Cell Biol.*, 10:689-695, 1990.
Rosel et al., *J. Virol.*, 60(2):436-449, 1986.
Rosenberg et al., *Ann. Surg.* 210(4):474-548, 1989.
Rosenberg et al., *N. Engl. J. Med.*, 319:1676, 1988.
Sambrook et al., In: *Molecular cloning: a laboratory manual*, 2$^{nd}$ Ed., Cold Spring Harbor Laboratory Press, Cold Spring Harbor, N. Y., 1989.
Saraiva and Alcami, *J. Virology*, 75(1):226-33, 2001.
Serrano et al., *Nature*, 366:704-707, 1993.
Serrano et al., *Science*, 267(5195):249-252, 1995.
Sinkovics and Horvath, *J. Clin. Viro.*, 16:1-15, 2000.
Smith et al., *Immunol. Rev.*, 159:137-154, 1997.
Smith et al., *J. Clin. Oncol.*, 18:2046-2052, 2000.
Smith et al., *Neuron.*, 20:1093-1102, 1998.
Solyanik et al., *Cell. Prolif.*, 28(5):263-278, 1995.
Spriggs et al., *Cell.*, 71(1):145-52, 1992.
Stokke et al., *Cell. Prolif.*, 30(5):197-218, 1997.
Symons et al., *Cell*, 81:551-560, 1995.
Todo et al., *Cancer Res.*, 61:153-161, 2001.
Tsujimoto and Croce, *Proc. Natl. Acad. Sci. USA*, 83(14): 5214-5218, 1986.
Tsujimoto et al., *Nature*, 315:340-343, 1985.
Tsujimoto et al., *Science*, 228(4706):1440-1443, 1985.
Tsumaki et al., *J. Biol. Chem.*, 273(36):22861-22864, 1998.
Upton et al., *Science*, 258(5086):1369-1372, 1992.
Upton et al., *Virology*, 184(1):370-82, 1991.
Vanderplasschen et al., *Proc. Natl. Acad. Sci. USA*, 95(13): 7544-7549, 1998.
Vicari and Caus, *Cytokine Growth Factor Rev.*, 13:143-154, 2002.
Vogelstein and Kinzler, *Cell*, 70(4):523-6, 1992.
Wallach et al., *Annu. Rev. Immunol.*, 17:331-367, 1999.
Wold et al., *J. Virol.* 52:307-313, 1984.
Wold et al., *Trends Microbiol.*, 2:437-443, 1994.
Wong et al., *Gene*, 10:87-94, 1980.
Wu et al., *Biochem. Biophys. Res. Commun.*, 233(1):221-226, 1997.
Zhao-Emonet et al., *Biochim. Biophys. Acta*, 1442(2-3):109-119, 1998.

The invention claimed is:

1. A method of inducing oncolysis in a human subject having a tumor comprising intratumorally administering to said subject one or more single doses of a pharmaceutical composition comprising a pharmaceutically acceptable carrier and a purified TK-deficient, replication-competent vaccinia virus vector wherein said single dose comprises at least $1\times10^9$ pfu.

2. The method of claim 1, wherein said tumor is a brain cancer tumor, a head & neck cancer tumor, an esophageal cancer tumor, a skin cancer tumor, a lung cancer tumor, a thymic cancer tumor, a stomach cancer tumor, a colon cancer tumor, a liver cancer tumor, an ovarian cancer tumor, a uterine cancer tumor, a bladder cancer tumor, a testicular cancer tumor, a rectal cancer tumor, a breast cancer tumor, or a pancreatic cancer tumor.

3. The method of claim 2, wherein the tumor is a hepatocellular carcinoma or a melanoma.

4. The method of claim 1, wherein said vaccinia virus vector expresses an immunostimulatory cytokine.

5. The method of claim 4, wherein the immunostimulatory cytokine is selected from the group consisting of IL-2, IL-12, GM-CSF and TNF-α.

6. The method of claim 1, wherein said tumor is recurrent.

7. The method of claim 1, wherein said tumor is primary.

8. The method of claim 1, wherein said tumor is metastatic.

9. The method of claim 1, further comprising administering to said subject a second cancer therapy.

10. The method of claim 1, further comprising a second cancer therapy selected from chemotherapy, biological therapy, radiotherapy, immunotherapy, hormone therapy, anti-vascular therapy, cryotherapy, toxin therapy or surgery.

11. The method of claim 1, wherein said subject is immunocompromised.

12. The method of claim 1, wherein said tumor is non-resectable prior to treatment and resectable following treatment.

13. The method of claim 1, further comprising assessing tumor cell viability following treatment.

14. The method of claim 1, further comprising imaging said tumor prior administration.

15. The method of claim 1, wherein said vaccinia virus comprises one or more modified viral genes selected from the group consisting of:
  (a) an interferon-modulating polypeptide;
  (b) a complement control polypeptide;
  (c) a TNF or chemokine-modulating polypeptide;
  (d) a serine protease inhibitor;
  (e) a IL-1β modulating polypeptide;
  (f) a non-infectious EEV form polypeptide; and
  (g) a viral polypeptide that act to inhibit release of infectious virus from cells (anti-infectious virus form polypeptide).

16. The method of claim 1, wherein the subject is administered 2 or more doses.

17. The method of claim 16, wherein 2 or more doses are administered over a period of at least 7 days.

18. The method of claim 1, Wherein the composition is administered weekly or every other week.

19. The method of claim 1, wherein said single dose comprises $1\times10^9$ pfu to $1\times10^{10}$ pfu.

20. The method of claim 1, whereby oncolysis is induced in said tumor and in at least one tumor that is not injected with the virus.

* * * * *